(12) United States Patent
Pillow et al.

(10) Patent No.: US 11,547,762 B2
(45) Date of Patent: Jan. 10, 2023

(54) METHODS FOR PREPARING ANTIBODY DRUG CONJUGATES

(71) Applicant: Genentech, Inc., South San Francisco, CA (US)

(72) Inventors: Thomas Pillow, South San Francisco, CA (US); Peter Dragovich, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 950 days.

(21) Appl. No.: 16/354,905

(22) Filed: Mar. 15, 2019

(65) Prior Publication Data

US 2019/0201544 A1    Jul. 4, 2019

Related U.S. Application Data

(63) Continuation of application No. PCT/EP2017/075272, filed on Oct. 4, 2017.

(60) Provisional application No. 62/404,514, filed on Oct. 5, 2016.

(51) Int. Cl.
| | |
|---|---|
| *A61K 47/68* | (2017.01) |
| *C07K 16/28* | (2006.01) |
| *C07K 16/22* | (2006.01) |
| *A61K 47/65* | (2017.01) |

(52) U.S. Cl.
CPC .......... *A61K 47/6803* (2017.08); *A61K 47/65* (2017.08); *A61K 47/6889* (2017.08); *C07K 16/22* (2013.01); *C07K 16/2863* (2013.01)

(58) Field of Classification Search
None
See application file for complete search history.

(56) References Cited

U.S. PATENT DOCUMENTS

| | | | |
|---|---|---|---|
| 9,814,782 B2 | 11/2017 | Park et al. | |
| 2013/0266595 A1* | 10/2013 | Flygare | A61P 35/00 540/496 |
| 2014/0030279 A1* | 1/2014 | Polakis | A61P 35/00 435/375 |
| 2014/0134193 A1* | 5/2014 | Subramanyam | A61P 43/00 548/953 |

(Continued)

FOREIGN PATENT DOCUMENTS

| | | |
|---|---|---|
| WO | 2008144544 A1 | 11/2008 |
| WO | 2014191726 A1 | 12/2014 |

(Continued)

OTHER PUBLICATIONS

Kaneko et al., Bioconjugate Chemistry (1991), 2(3), 133-41 (Year: 1991).*

(Continued)

*Primary Examiner* — Karl J Puttlitz
(74) *Attorney, Agent, or Firm* — Viksnins Harris Padys Malen LLP

(57) ABSTRACT

The subject matter described herein is directed to methods of preparing certain antibody-drug conjugates (ADCs) wherein the antibody is linked to the drug through a linker, wherein the drug contains a heteroaryl group having a secondary nitrogen, and the linker is attached to the drug via the secondary nitrogen. The resulting conjugates are useful in treating various diseases and conditions.

10 Claims, 6 Drawing Sheets

Specification includes a Sequence Listing.

(56) References Cited

U.S. PATENT DOCUMENTS

| | | | | |
|---|---|---|---|---|
| 2014/0357661 | A1* | 12/2014 | Bradbury | A61K 31/519 546/85 |
| 2015/0165063 | A1* | 6/2015 | Flygare | A61K 47/6803 546/276.7 |
| 2016/0074527 | A1* | 3/2016 | Flygare | C07K 16/2803 540/496 |
| 2016/0074528 | A1* | 3/2016 | Flygare | A61K 31/704 530/391.9 |

FOREIGN PATENT DOCUMENTS

| | | |
|---|---|---|
| WO | 2016040724 A1 | 3/2016 |
| WO | 2016044560 A1 | 3/2016 |
| WO | 2016085967 A1 | 6/2016 |
| WO | 2017064675 A1 | 4/2017 |
| WO | 2018031662 A1 | 2/2018 |

OTHER PUBLICATIONS

De Savi et al., J. Med. Chem. 2015, 58, 8128-8140 (Year: 2015).*

De Savi, C , et al., "Optimization of a Novel Binding Motif to (E)-3-(3,5-Difluoro-4- ((1R,3R)-2-(2-fluoro-2-methylpropyl)-3-methyl-2,3,4,9-tetrahydro-1H-pyrido[3,4-b]indol-1-yl)phenyl)acrylic Acid (AZD9496), a Potent and Orally Bioavailable Selective Estrogen Receptor Downreg", J Med Chem 58, 8128-8140 (2015).

Dragovich, P , et al., "Conjugation of Indoles to Antibodies through a Novel Self-Immolating Linker", Chem Eur J 24, 4830-4834 (2018).

Flygare, J , et al., "Antibody-Drug Conjugates for the Treatment of Cancer", Chem Biol Drug Des 81, 113-121 (2013).

Kaushik, N , et al., "Biomedical Importance of Indoles", Molecules 18, 6620-6662 (2013).

Ohri, R , et al., "High-Throughput Cysteine Scanning To Identify Stable Antibody Conjugation Sites for Maleimide- and Disulfide-Based Linkers", Bioconjugate Chem 29, 473-485 (2018).

Patent Cooperation Treaty, International Searching Authority, Search Report and Written Opinion for PCT/EP2017/075272, 16 pages, dated Feb. 6, 2018.

Pei, Z , et al., "Exploration of Pyrrolobenzodiazepine (PBD)-Dimers Containing Disulfide-Based Prodrugs as Payloads for Antibody-Drug Conjugates", Mol Pharmaceutics 15, 3979-3996 (2018).

Pillow, T , et al., "Decoupling stability and release in disulfide bonds with antibody-small molecule conjugates", Chem Sci 8, 366-370 (2017).

Pillow, T , et al., "Modulating Therapeutic Activity and Toxicity of Pyrrolobenzodiazepine Antibody-Drug Conjugates with Self-Immolative Disulfide Linkers", Mol Cancer Ther 16(5), 871-878 (2017).

Sadowsky, J , et al., "Development of Efficient Chemistry to Generate Site-Specific Disulfide-Linked Protein- and Peptide-Payload Conjugates: Application to THIOMAB Antibody-Drug Conjugates", Bioconjugate CheM 28, 2086-2098 (2017).

Su, D , et al., "Modulating Antibody-Drug Conjugate Payload Metabolism by Conjugation Site and Linker Modification", Bioconjugate Chem 29, 1155-1167 (2018).

Weir, H , et al., "AZD9496: An Oral Estrogen Receptor Inhibitor That Blocks the Growth of ER-Positive and ESR1-Mutant Breast Tumors in Preclinical Models", Cancer Res 76 (11), 3307-3318 (2016).

Zhang, D , et al., "Chemical Structure and Concentration of Intratumor Catabolites Determine Efficacy of Antibody Drug Conjugates", Drug Metabolism and Disposition 44(9), 1517-1523 (2016).

Zhang, D , et al., "Intratumoral Payload Concentration Correlates with the Activity of Antibody-Drug Conjugates", Mol Cancer Ther 17 (3), 677-685 (2018).

Zhang, D , et al., "Linker Immolation Determines Cell Killing Activity of Disulfide-Linked Pyrrolobenzodiazepine Antibody-Drug Conjugates", ACS Med Chem Lett 7, 988-993 (2016).

Putey, A. , et al., "Synthesis and biological evaluation of tetrahydro[1,4]diazepino[1,2-a]indol-1-ones as cyclin-dependent kinase inhibitors", European Journal of Medicinal Chemistry 83, 617-629 (2014).

* cited by examiner

METHODS FOR PREPARING ANTIBODY DRUG CONJUGATES

CROSS-REFERENCE TO RELATED APPLICATIONS

This application is a continuation of International Application PCT/EP2017/075272, with international filing date of 4 Oct. 2017, which claims the benefit of priority to U.S. provisional Application No. 62/404,514 filed 5 Oct. 2016, and the contents of each application are hereby incorporated by reference in their entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Oct. 3, 2017, is named SEQLIST_ST25.txt and 75,169 bytes in size.

FIELD OF THE INVENTION

The subject matter described herein is directed to methods of preparing certain antibody-drug conjugates (ADCs) wherein the antibody is linked to the drug through a linker, wherein the drug contains a heteroaryl group having a secondary nitrogen, and the linker is attached to the drug via the secondary nitrogen.

BACKGROUND

The major treatment modalities used by oncologists to treat cancer are surgical resection, radiation therapy, and classical chemotherapeutic drugs. Unfortunately, surgical resection is not a viable option for many tumors or forms of cancers. Further, radiation therapy and chemotherapeutic drugs do not target only diseased cells, and therefore it is often the case that damage occurs to off-target healthy cells.

Therapeutics that more specifically target tumor cells are being developed by taking advantage of tumor-specific expression of antigens or inappropriate overexpression or activation of specific proteins within tumor cells. However, tumor cells are prone to mutation and can become resistant to drugs that specifically target tumor cells.

Antibody therapy can provide more targeted therapy with less off-target toxicity. The use of an antibody-drug conjugate (ADC) for the local delivery of cytotoxic or cytostatic agents can provide delivery of the drug moiety to tumors, and intracellular accumulation therein. Efforts to design ADCs have focused on the selectivity of monoclonal antibodies (mAbs) as well as drug mechanism of action, drug-linking, and drug/antibody ratio (loading).

Within the efforts described above, the design of the drug linker is of importance, because it impacts both the efficacy and safety of the ADCs. The linker needs to provide sufficient stability during systemic circulation but allow for the rapid and efficient intracellular release of the drug in an active form.

Currently, however, the chemical functionality which may be used in forming linkages between a linker and a drug are limited. This limits both the linkers and drugs that may be used in ADCs. Therefore, there exists a need for methodologies which allow for the use of drugs with varied chemical functionality in the production of ADCs.

BRIEF SUMMARY

In embodiments, the subject matter described herein is directed to methods of makings ADCs of Formula I.

In embodiments, the subject matter described herein is directed to ADCs of Formula I.

In embodiments, the subject matter described herein is directed to methods of makings compounds of Formula III.

In embodiments, the subject matter described herein is directed to compounds of Formula III.

Other embodiments are also described.

DETAILED DESCRIPTION

Figure 1:
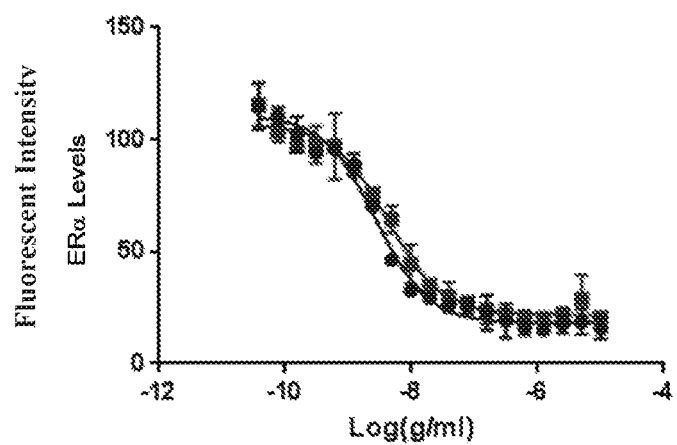
FIG. 1 is a graph showing the reduction of ERα levels in MCF7-neo/HER2 cells treated with either CNJ-1 (HER2, circles) or CM-2 (B7H4, squares).

Described herein are methods for conjugating antibodies to biologically active molecules through a linker that is covalently bound to a secondary nitrogen contained in the structure of the biologically active molecule. As set forth below, the methods provide compounds of Formulae II and III, which are amenable to conjugation with antibodies. The compounds of Formulae II and III contain a carbamate formed by a secondary nitrogen on a biologically active molecule and an oxycarbonyl on a linker moiety. The compounds of Formulae II and III can then be conjugated with a wide variety of antibodies, engineered antibodies, antibody fragments, etc., to prepare ADCs of Formula I.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

As used herein, the term "alkyl" refers to a straight-chained or branched hydrocarbon group containing 1 to 12 carbon atoms. Examples of alkyl groups include methyl, ethyl, n-propyl, isopropyl, tert-butyl, and n-pentyl. Alkyl groups may be optionally substituted with one or more substituents.

The term "substituent" refers to an atom or a group of atoms that replaces a hydrogen atom on a molecule. The term "substituted" denotes that a specified molecule bears one or more substituents. Examples of substituents include alkyl, cycloalkyl, aryl, heteroaryl, hydroxyl, nitrile, halo, alkoxy, haloalkoxy, arylalkoxy, acyloxy, alkylthio, sulfonate, amino, alkylamino, acylamino, carbamoyl, alkylcarbamoyl, or nitro.

The term "alkoxy" refers to an —O-alkyl radical. Alkoxy groups may be optionally substituted with one or more substituents.

The term "haloalkoxy" refers to an —O-alkyl group that is substituted by one or more halo substituents. Examples of haloalkoxy groups include trifluoromethoxy and 2,2,2-trifluoroethoxy.

The term "arylalkoxy" refers to an —O-alkyl group that is substituted by an aryl substituent. An examples of an arylalkoxy group is O-benzyl.

The term "alkylamino" refers to an amino substituent which is further substituted with one or two alkyl groups.

The term "alkylthio" refers to an —S-alkyl radical. Alkylthio groups may be optionally substituted with one or more substituents.

The term "acylamino" refers to an amino substituent which is further substituted with a —CO—R group. Examples of acylamino groups include acetamido and 2-phenylacetamido.

The term "a compound of the formula" or "a compound of formula" or "compounds of the formula" or "compounds of formula" refers to any compound selected from the genus of compounds as defined by Formula II, III, V, VI, VII, VIII, IX, X, and XI.

The term "benzyl" refers to a hydrocarbon with the formula of $C_6H_5CH_2$ where the point of attachment to the group in question is at the $CH_2$ position. The benzyl may be substituted on the aromatic ring. In one embodiment, 0, 1, 2, 3, 4, or 5 atoms of the aryl group may be substituted by a substituent.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl groups include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may have one, two, or more different tautomeric forms. Heteroaryl groups may be optionally substituted with one or more substituents. In one embodiment, 0, 1, 2, 3, or 4 atoms of each ring of a heteroaryl group may be substituted by a substituent. Non-limiting examples of such heteroaryl groups include imidazolyl, quinolyl, isoquinolyl, indolyl, indazolyl, pyridazyl, pyridyl, pyrrolyl, pyrazolyl, pyrazinyl, quinoxolyl, pyranyl, pyrimidinyl, furyl, thienyl, triazolyl, thiazolyl, carbolinyl, tetrazolyl, benzofuranyl, thiamorpholinyl sulfone, oxazolyl, benzoxazolyl, benzimidazolyl, benzthiazolyl, oxopiperidinyl, oxopyrrolidinyl, oxoazepinyl, azepinyl, isoxazolyl, isothiazolyl, furazanyl, thiadiazyl, oxathiolyl, acridinyl, phenanthridinyl, and benzocinnolinyl, and the like.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "heterocycloalkyl" refers to a ring or ring system containing at least one heteroatom selected from nitrogen, oxygen, and sulfur, wherein said heteroatom is in a non-aromatic ring. The heterocycloalkyl ring is optionally fused to or otherwise attached to other heterocycloalkyl rings and/or non-aromatic hydrocarbon rings and/or phenyl rings. Examples of heterocycloalkyl groups include, for example, piperazinyl, morpholinyl, 1,2,3,4-tetrahydroisoquinolinyl, piperidinyl, tetrahydrofuranyl, pyrrolidinyl, pyridinoyl, and pyrazolidinyl. The heterocycloalkyl groups may be substituted.

As used herein, unless defined otherwise in a claim, the term "optionally" means that the subsequently described event(s) may or may not occur, and includes both event(s) that occur and event(s) that do not occur.

As used herein, unless defined otherwise, the phrase "optionally substituted", "substituted" or variations thereof denote an optional substitution, including multiple degrees of substitution, with one or more substituent group, for example, one, two or three. The phrase should not be interpreted as duplicative of the substitutions herein described and depicted.

The term "chiral" refers to molecules which have the property of non-superimposability of the mirror image partner, while the term "achiral" refers to molecules which are superimposable on their mirror image partner. As used herein, chiral atoms use the "R" and "S" nomenclature to designate the absolute configuration at said chiral atom.

The term "diastereomers" refers to stereoisomers with two or more centers of dissymmetry and whose molecules are not minor images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

As used herein, a "leaving group" is the group that is displaced by a nucleophile in a conjugation reaction. Leaving groups can be anions or neutral molecules. Anionic leaving groups can be, for example, halides and sulfonate esters. The group displacing the leaving group can be, for example, a nucleophile. A "nucleophile" or "nucleophilic group" is a chemical species having unshared pair electrons (e.g., any Lewis base), and can be neutral or have a negative charge. A nucleophile donates an electron pair to form a chemical bond during a chemical reaction. Non-limiting examples of the nucleophilic group include an oxygen-containing group (e.g., hydroxyl, alkoxy, or acyloxy), a sulfur-containing group (e.g., mercapto, alkylthio, or sulfonate), a nitrogen-containing group (e.g., amino, alkylamino, acylamino, nitro, azido, or isocyanato), and halogen.

The term "protecting group" refers to chemical moieties that are used during the preparation of compounds or antibody-drug conjugates for protection of functionality (e.g., primary or secondary amines, carboxylic acids, or thiols). For a general description of protecting groups and their use, see T. W. Greene, Protective Groups in Organic Synthesis, John Wiley & Sons, New York, 1991.

Suitable amino-protecting groups include acetyl, trifluoroacetyl, t-butoxycarbonyl (Boc), benzyloxycarbonyl (CBz or CBZ) and 9-fluorenylmethyleneoxycarbonyl (Fmoc). Suitable thiol protecting groups are, for example, unsubstituted or substituted benzyl groups such as a benzyl group, a p-methoxybenzyl group, a 4-methylbenzyl group, a 3,4-dimethylbenzyl group, a p-hydroxybenzyl group, a p-acetoxybenzyl group and a p-nitrobenzyl group, a diphenylmethyl group, a trityl group, a t-butyl group, an acetyl group, a benzoyl group, and so on, with an acid labile protecting group being more preferable. Acid labile thiol protecting groups can be, for example, trityl, fluorenyl, dimethoxybenzyl, methoxybenzyl, 2,4,6-trimethyl benzyl, xanthenyl, ferrocenyl, methoxymethyl, isobutoxymethyl, and diphenylmethyl. Suitable carboxylic acid protecting groups can be, for example, branched and unbranched alkyl groups and silyl groups.

In general, the species of protecting group is not critical provided that it is stable to the conditions of any subsequent reaction(s) on other positions of the compound and can be removed at the appropriate point without adversely affecting the remainder of the molecule.

As used herein, the "contacting" refers to reagents in close proximity so that a reaction may occur.

As used herein, "ambient temperature" or "room temperature" refers to a temperature in the range of about 20 to 25° C.

The phrase "pharmaceutically acceptable" indicates that the substance or composition must be compatible chemically and/or toxicologically, with the other ingredients comprising a formulation, and/or the subject being treated therewith.

The phrase "pharmaceutically acceptable salt" as used herein, refers to pharmaceutically acceptable organic or inorganic salts of a compound of the subject matter described herein. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt, the salt can have multiple counter ions. Hence, a pharmaceutically acceptable salt can have one or more charged atoms and/or one or more counter ion.

Other salts, which are not pharmaceutically acceptable, may be useful in the preparation of compounds of described herein and these should be considered to form a further aspect of the subject matter. These salts, such as oxalic or trifluoroacetate, while not in themselves pharmaceutically acceptable, may be useful in the preparation of salts useful as intermediates in obtaining the compounds described herein and their pharmaceutically acceptable salts.

The components of the ADC can also be described in terms of a "residue," "moiety" or "group," which refers to the component being covalently bound to another component.

The term "covalently bound" or "covalently linked" refers to a chemical bond formed by sharing of one or more pairs of electrons.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

As used herein, a "reduced antibody" refers to an antibody wherein at least one cysteine has a free thiol group.

As used herein, the term "acidic conditions" refers to a milieu having a pH below 7.0, and specifically conditions that are amenable to cleavage of a leaving group or protecting group, e.g., a pH of less than 1.0, less than 2.0, less than 3.0, less than 4.0, less than 5.0, or less than 6.0.

As used herein, a "reducing agent" is a reagent that causes another substance to undergo reduction and that is oxidized in the process. In the presence of antibodies, reducing agents can be used to stabilize free cysteines and to reduce disulfide bonds. Non-limiting examples of reducing agents are 2-mercaptoethanol, 2-mercaptoethylamine, dithiothreitol, and tris (2-carboxyethyl)phosphine.

As used herein, an "oxidizing agent" is a substance that causes another substance to undergo oxidation and that is reduced in the process. A non-limiting example of an oxidizing agents is DHAA.

As used herein, a "buffer" is a solution that resists changes in pH when acid or base is added to it. Buffers typically involve a weak acid or bases together with one of its salts. Non-limiting examples of buffers are Tris, HEPES, PBS (phosphate buffered saline), triethylammonium acetate buffer, and triethylammonium bicarbonate buffer.

The term "antibody fragment(s)" as used herein comprises a portion of a full length antibody, generally the antigen binding or variable region thereof. Examples of antibody fragments include Fab, Fab', F(ab')$_2$, and Fv fragments; diabodies; linear antibodies; minibodies (Olafsen et al (2004) Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the subject matter described herein may be made by the hybridoma method first described by Kohler et al (1975) Nature, 256:495, or may be made by recombinant DNA methods (see for example: U.S. Pat. Nos. 4,816,567; 5,807,715). The monoclonal antibodies may also be isolated from phage antibody libraries using the techniques described in Clackson et al (1991) Nature, 352: 624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA. 81:6851-6855). Chimeric antibodies of interest herein include "primatized" antibodies comprising variable domain antigen-binding sequences derived from a non-human primate (e.g., Old World Monkey, Ape, etc.) and human constant region sequences.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\epsilon$, $\gamma$, and $\mu$, respectively.

The term "intact antibody" as used herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

The term "Fc region" as used herein means a C-terminal region of an immunoglobulin heavy chain that contains at least a portion of the constant region.

The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

The term "framework" or "FR" as used herein refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267: 7246-7256; US 2005/0048572; US 2004/0229310).

The term "human consensus framework" as used herein refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Inter-*

*est*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "variable region" or "variable domain" as used herein refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "epitope" refers to the particular site on an antigen molecule to which an antibody binds.

The "epitope 4D5" or "4D5 epitope" or "4D5" is the region in the extracellular domain of HER2 to which the antibody 4D5 (ATCC CRL 10463) and trastuzumab bind. This epitope is close to the transmembrane domain of HER2, and within domain IV of HER2. To screen for antibodies which bind to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 550 to about residue 610, inclusive, of HER2 (SEQ ID NO: 39).

The "epitope 2C4" or "2C4 epitope" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. The 2C4 antibody and pertuzumab bind to the extracellular domain of HER2 at the junction of domains I, II and III (Franklin et al. *Cancer Cell* 5:317-328 (2004)).

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

Specific illustrative and exemplary embodiments for measuring binding affinity are described in the following. In certain embodiments, an antibody as described herein has dissociation constant (Kd) of $\leq 1$ µM, $\leq 100$ nM, $\leq 10$ nM, $\leq 5$ nm, $\leq 4$ nM, $\leq 3$ nM, $\leq 2$ nM, $\leq 1$ nM, $\leq 0.1$ nM, $\leq 0.01$ nM, or $\leq 0.001$ nM (e.g., $10^{-8}$ M or less, e.g. from $10^{-8}$ M to $10^{-13}$ M, e.g., from $10^{-9}$ M to $10^{-13}$ M).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "free cysteine amino acid" as used herein refers to a cysteine amino acid residue which has been engineered into a parent antibody, has a thiol functional group (—SH), and is not paired as an intramolecular or intermolecular disulfide bridge.

The term "amino acid" as used herein means glycine, alanine, valine, leucine, isoleucine, phenylalanine, proline, serine, threonine, tyrosine, cysteine, methionine, lysine, arginine, histidine, tryptophan, aspartic acid, glutamic acid, asparagine, glutamine or citrulline.

The term "Linker", "Linker Unit", or "link" as used herein means a chemical moiety comprising a chain of atoms that covalently attaches a drug to an antibody. In various embodiments, a linker is a divalent radical, specified as L1.

As used herein, the term "plurality" refers to two or more conjugates. Each conjugate can be the same or different from any other conjugate in the plurality.

Other terms, definitions and abbreviations herein include: Wild-type ("WT"); Cysteine engineered mutant antibody ("thio"); light chain ("LC"); heavy chain ("HC"); 6-maleimidocaproyl ("MC"); maleimidopropanoyl ("MP"); valine-citrulline ("val-cit" or "vc"), alanine-phenylalanine ("ala-phe"), p-aminobenzyl ("PAB"), and p-aminobenzyloxycarbonyl ("PABC"); A118C (EU numbering)=A121C (Sequential numbering)=A114C (Kabat numbering) of heavy chain K149C (Kabat numbering) of light chain. Still additional definitions and abbreviations are provided elsewhere herein.

Additional definitions are also provided below.

II. Antibody-Drug-Conjugate (ADCs) and Methods of Preparation

The Antibody-Drug Conjugate (ADC) molecules described herein comprise an antibody conjugated via a linker (L1) to a drug. The general Formula I of an ADC is:

$$\text{Ab-(L1-D)}_p, \quad \text{I}$$

wherein, D is a biologically active molecule, e.g. a drug; L1 is a linker, covalently bound to Ab and to D; and p has a value from about 1 to about 10, or about 1 to about 9, or about 1 to about 8, or about 1 to about 7, or about 1 to about 6, or about 1 to about 5, or about 1 to about 4, or about 1 to about 3. In an embodiment, p is about 2.

The methods described herein are useful for preparing ADCs of Formula I as well as ADCs wherein more than one, i.e., an integer from 1 to 10, linker-biologically active molecules are conjugated to a single antibody as in Formula I.

In embodiments, a method for preparing an antibody-drug conjugate of Formula I:

$$\text{Ab-(L1-D)}_p \quad \text{I}$$

or a pharmaceutically acceptable salt thereof, wherein
Ab is an antibody;
L1 is a linking moiety;
D is a biologically active molecule comprising a secondary nitrogen containing heteroaryl, wherein L1 is covalently bonded to the secondary nitrogen; and
p is about 1, 2, 3, 4, 5, 6, 7, 8, 9, or 10, and preferably p is about 2;
the method comprising:
i. contacting a compound of Formula II $$\text{T-L1-D} \quad \text{II}$$

with an antibody, wherein,
L1 and D are as described above,
T is a leaving group having the structure $R^5$—S, wherein $R^5$ is an optionally substituted pyridine, wherein an antibody-drug conjugate of Formula I is prepared.

As in any embodiment above, a method wherein L1 has the structure

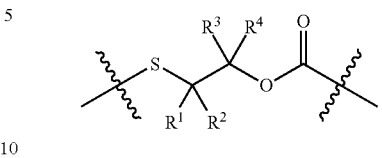

wherein,
$R^1$, $R^2$, $R^3$, and $R^4$ are independently selected from the group consisting of H, optionally substituted branched or linear $C_1$-$C_5$ alkyl, and optionally substituted $C_3$-$C_6$ cycloalkyl, or $R^3$ and $R^4$ taken together with the carbon atom to which they are bound form a $C_3$-$C_6$ cycloalkyl ring, wherein said optionally substituted alkyl or cycloalkyl may be substituted with alkyl, cycloalkyl, aryl, heteroaryl, hydroxyl, nitrile, halo, alkoxy, haloalkoxy, arylalkoxy, acyloxy, alkylthio, sulfonate, amino, alkylamino, acylamino, carbamoyl, alkylcarbamoyl, or nitro.

The method as in any embodiment above, wherein T-L1-D has the following formula:

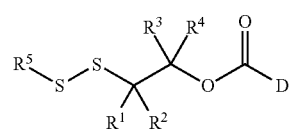

III wherein, $R^5$ is selected from the group consisting of optionally substituted pyridine and nitropyridine.

The method as in any embodiment above, wherein $R^5$ is 5-nitropyridine.

The method as in any embodiment above, wherein $R^1$, $R^2$, $R^3$, and $R^4$ are independently selected from the group consisting of H and optionally substituted branched or linear $C_1$-$C_5$ alkyl.

The method as in any embodiment above, wherein one of $R^1$, $R^2$, $R^3$, and $R^4$ is optionally substituted branched or linear $C_1$-$C_5$ alkyl and the others are H.

The method as in any embodiment above, wherein the optionally substituted branched or linear $C_1$-$C_5$ alkyl is methyl.

The method as in any embodiment above, wherein $R^1$ is methyl, and $R^2$, $R^3$, and $R^4$ are each H.

The method as in any embodiment above, wherein said antibody-drug conjugate of Formula I has the structure:

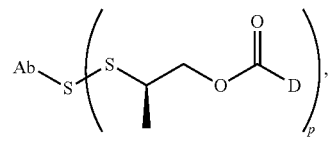

wherein p is 1, 2, 3, 4, 5, 6, 7, 8, 9, or 10, and preferably p is about 2.

The method as in any embodiment above, wherein said antibody-drug conjugate of Formula I has the structure:

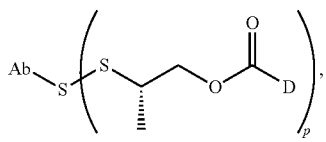

wherein p is 1, 2, 3, 4, 5, 6, 7, 8, 9, or 10, and preferably p is about 2.

The method as in any embodiment above, wherein said Ab is a cysteine engineered antibody or variants thereof.

The method as in any embodiment above, wherein the antibody binds to HER2 or B7-H4.

The method as in any embodiment above, wherein the antibody binds to HER2.

The method as in any embodiment above, wherein said contacting comprises:
  i. contacting said Ab with a suitable reducing agent to prepare a reduced Ab,
  ii. oxidizing said reduced Ab to prepare Ab', and
  iii. contacting said Ab' with T-L1-D in the presence of a suitable buffer.

The method as in any embodiment above, wherein said buffer has a pH of about 8.5.

The method as in any embodiment above, wherein said contacting comprises:
  i. contacting said Ab with a molar excess of DTT at ambient temperature to prepare a reduced Ab,
  ii. purifying said reduced Ab,
  iii. oxidizing said purified, reduced Ab with DHAA at ambient temperature to prepare Ab',
  iv. purifying said Ab',
  v. contacting said purified Ab' with T-L1-D in a buffer solution at a pH of about 8.5 to prepare Ab-L1-D, and
  vi. purifying said Ab-L1-D.

The method as in any embodiment above, wherein the carbonyl of L1 is covalently bound to said secondary nitrogen of the heteroaryl of D, wherein said heteroaryl is selected from the group consisting of:

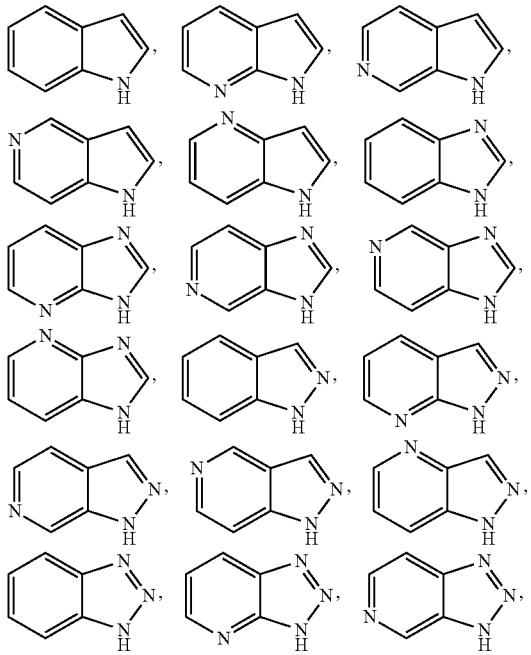

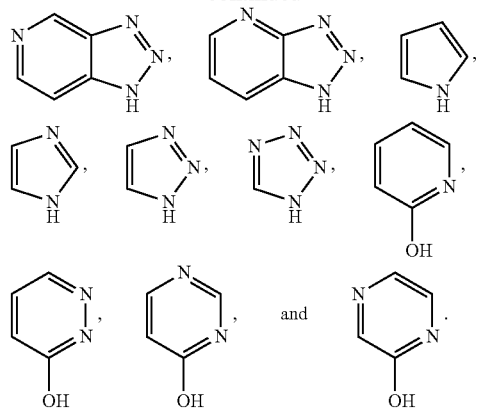

The method as in any embodiment above, wherein the heteroaryl is selected from the group consisting of:

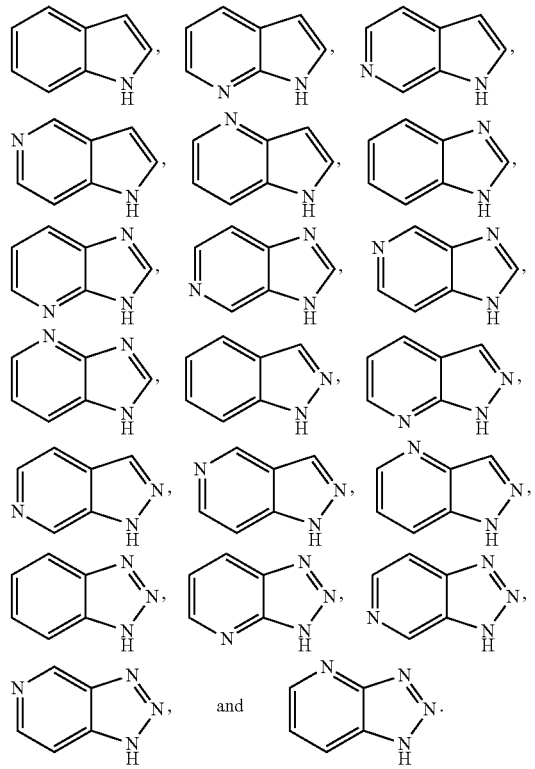

The method as in any embodiment above, wherein the heteroaryl is selected from the group consisting of:

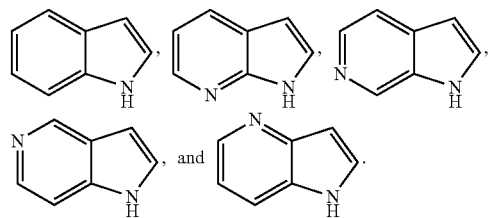

The method as in any embodiment above, wherein the heteroaryl is

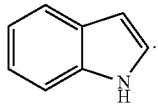

The method as in any embodiment above, wherein D is selected from the group consisting of

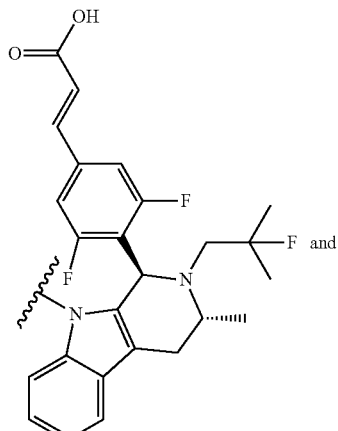

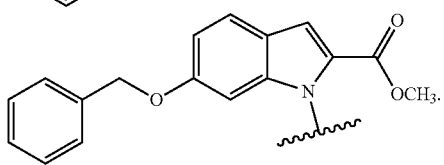

The method as in any embodiment above, wherein D is

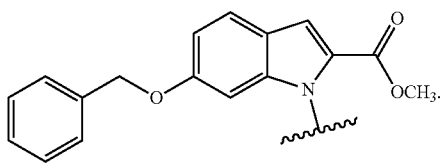 [SMILES: *n1c(C(=O)OC)cc2ccc(OCc3ccccc3)cc21]

The method as in any embodiment above, wherein D is

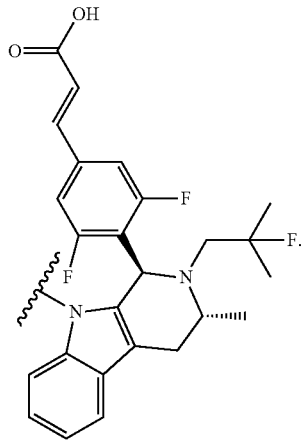 [SMILES: *n1c2c(c3ccccc31)C[C@@H](C)N(CC(C)(C)F)[C@@H]2c1c(F)cc(/C=C/C(=O)O)cc1F]

The method as in any embodiment above, wherein the antibody-drug conjugate of Formula I is selected from the group consisting of:

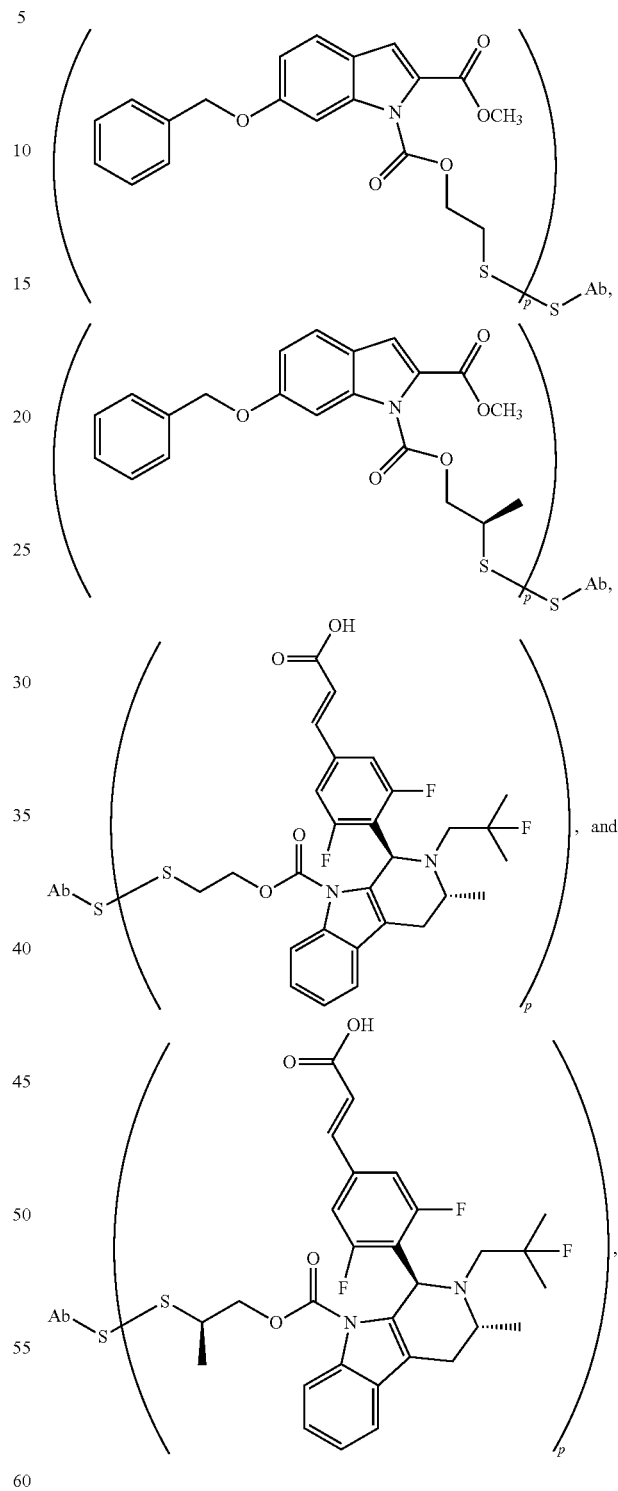

wherein p is 1, 2, 3, 4, 5, 6, 7, 8, 9, or 10, and preferably p is about 2.

The method as in any embodiment above, wherein said antibody is Anti-HER2 7C2 LC K149C or Anti-B7H4 1D11v1.9 varD LC K149C.]

In embodiments, the subject mater herein is directed to an antibody-drug conjugate of Formula IV:

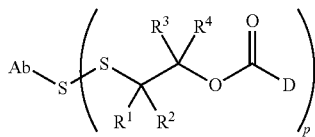

or a pharmaceutically acceptable salt thereof, wherein
Ab is an antibody;

$R^1$, $R^2$, $R^3$, and $R^4$ are independently selected from the group consisting of H, optionally substituted branched or linear $C_1$-$C_5$ alkyl, and optionally substituted $C_3$-$C_6$ cycloalkyl, or $R^3$ and $R^4$ taken together with the carbon atom to which they are bound form a $C_3$-$C_6$ cycloalkyl ring, wherein said optionally substituted alkyl or cycloalkyl may be substituted with alkyl, cycloalkyl, aryl, heteroaryl, hydroxyl, nitrile, halo, alkoxy, haloalkoxy, arylalkoxy, acyloxy, alkylthio, sulfonate, amino, alkylamino, acylamino, carbamoyl, alkylcarbamoyl, or nitro;

D is a biologically active molecule comprising a secondary nitrogen containing heteroaryl wherein the carbonyl in Formula IV is covalently bonded to the secondary nitrogen in D; and p is 1, 2, 3, 4, 5, 6, 7, 8, 9, or 10, and preferably p is about 2.

As in any embodiment above, the antibody-drug conjugate wherein $R^1$, $R^2$, $R^3$, and $R^4$ are independently selected from the group consisting of H and optionally substituted branched or linear $C_1$-$C_5$ alkyl.

As in any embodiment above, the antibody-drug conjugate wherein one of $R^1$, $R^2$, $R^3$, and $R^4$ is optionally substituted branched or linear $C_1$-$C_5$ alkyl and the others are H.

As in any embodiment above, the antibody-drug conjugate wherein said optionally substituted branched or linear $C_1$-$C_5$ alkyl is methyl.

As in any embodiment above, the antibody-drug conjugate wherein $R^1$ is methyl, and $R^2$, $R^3$, and $R^4$ are each H.

As in any embodiment above, the antibody-drug conjugate wherein said antibody-drug conjugate of Formula IV has the structure:

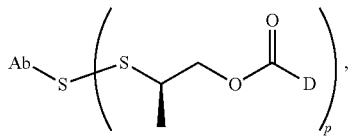

wherein p is 1, 2, 3, 4, 5, 6, 7, 8, 9, or 10, and preferably p is about 2.

As in any embodiment above, the antibody-drug conjugate, wherein said antibody-drug conjugate of Formula IV has the structure:

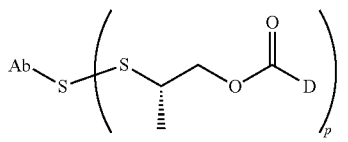

wherein p is 1, 2, 3, 4, 5, 6, 7, 8, 9, or 10, and preferably p is about 2.

As in any embodiment above, the antibody-drug conjugate wherein said Ab is a cysteine engineered antibody or variants thereof.

As in any embodiment above, the antibody-drug conjugate wherein the antibody binds to HER2 or B7-H4.

As in any embodiment above, the antibody-drug conjugate wherein the antibody binds to HER2.

As in any embodiment above, the antibody-drug conjugate wherein the carbonyl of Formula IV is covalently bound to the secondary nitrogen of the heteroaryl of D, wherein the heteroaryl is selected from the group consisting of:

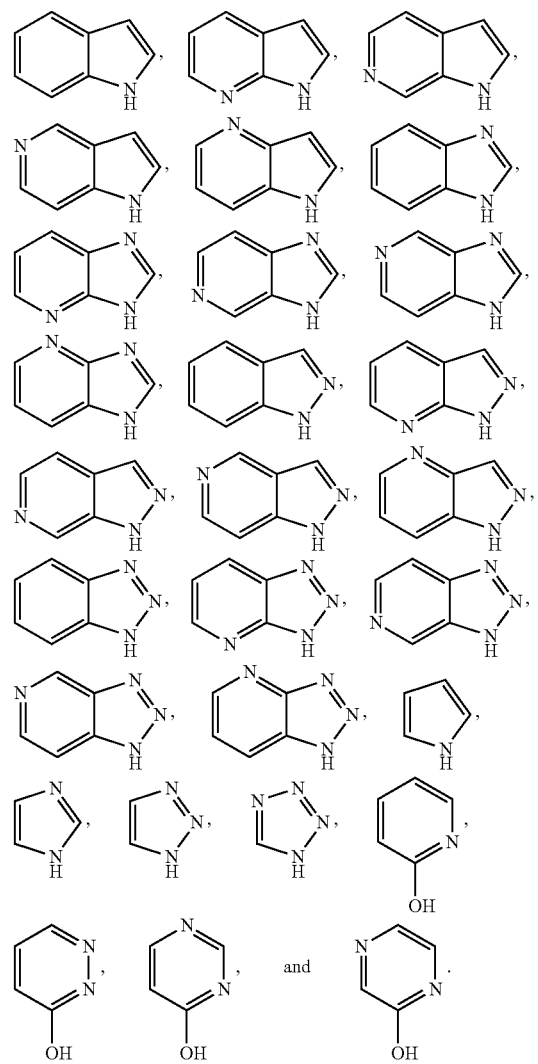

As in any embodiment above, the antibody-drug conjugate wherein the heteroaryl is selected from the group consisting of:

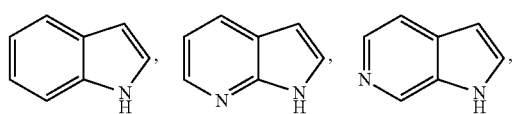

-continued

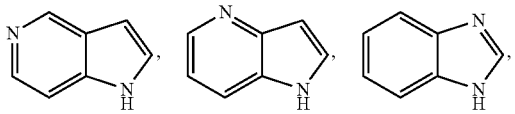

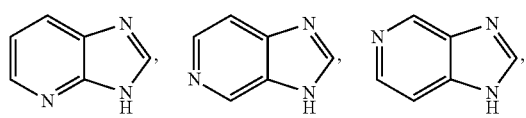

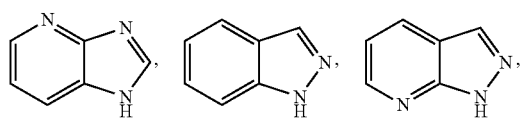

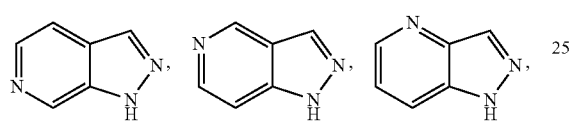

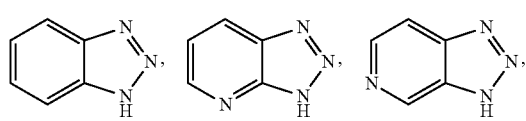

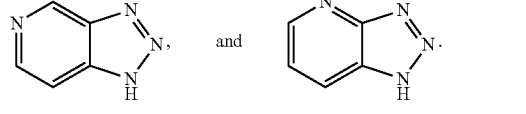

As in any embodiment above, the antibody-drug conjugate wherein the heteroaryl is selected from the group consisting of:

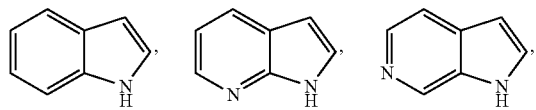

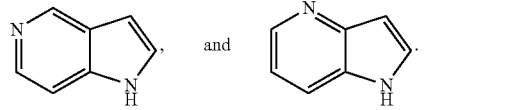

As in any embodiment above, the antibody-drug conjugate wherein the heteroaryl is

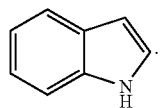

As in any embodiment above, the antibody-drug conjugate wherein D is selected from the group consisting of

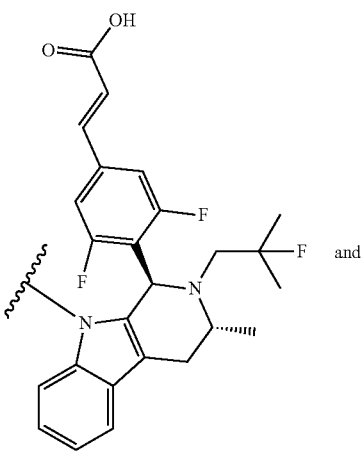 and

As in any embodiment above, the antibody-drug conjugate wherein D is

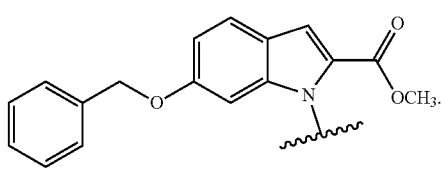 [SMILES: *n1c(C(=O)OC)cc2ccc(OCc3ccccc3)cc21]

As in any embodiment above, the antibody-drug conjugate wherein D is

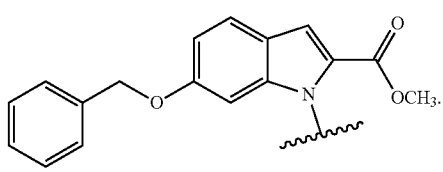

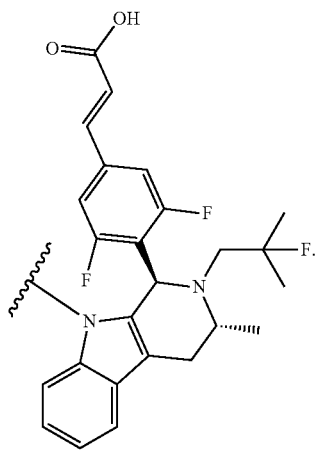 [SMILES: *n1c2c(c3ccccc31)C[C@@H](C)N(CC(C)(C)F)[C@@H]2c1c(F)cc(/C=C/C(=O)O)cc1F]

As in any embodiment above, the antibody-drug conjugate selected from the group consisting of:

wherein p is 1, 2, 3, 4, 5, 6, 7, 8, 9, or 10, and preferably p is about 2.

As in any embodiment above, the antibody-drug conjugate having the structure wherein the antibody is Anti-HER2 7C2 LC K149C and p is 1, 2, 3, 4, 5, 6, 7, 8, 9, or 10, and preferably p is about 2.

As in any embodiment above, the antibody-drug conjugate having the structure wherein the antibody is Anti-B7H4 1D11v1.9 varD LC K149C and p is 1, 2, 3, 4, 5, 6, 7, 8, 9, or 10, and preferably p is about 2.

In embodiments, a method for preparing a compound of Formula III:

III wherein, $R^1$, $R^2$, $R^3$, and $R^4$ are independently selected from the group consisting of H, optionally substituted branched or linear $C_1$-$C_5$ alkyl, and optionally substituted $C_3$-$C_6$ cycloalkyl, or $R^3$ and $R^4$ taken together with the carbon atom to which they are bound form a $C_3$-$C_6$ cycloalkyl ring, wherein said optionally substituted alkyl or cycloalkyl may be substituted with alkyl, cycloalkyl, aryl, heteroaryl, hydroxyl, nitrile, halo, alkoxy, haloalkoxy, arylalkoxy, acyloxy, alkylthio, sulfonate, amino, alkylamino, acylamino, carbamoyl, alkylcarbamoyl, or nitro; and D is a biologically active molecule comprising a secondary nitrogen containing heteroaryl wherein the carbonyl in Formula III is covalently bonded to the secondary nitrogen in D;

$R^5$ is selected from the group consisting of optionally substituted pyridine and nitropyridine;

the method comprising:

i. contacting a compound of Formula V:

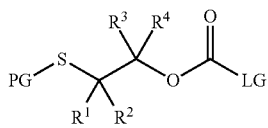

wherein LG is a leaving group and PG is a protecting group, with a compound, D, to prepare a compound of Formula VI:

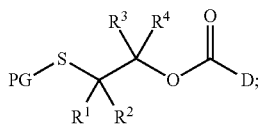

and, ii. deprotecting the compound of Formula VI under acidic conditions to prepare a compound of Formula III:

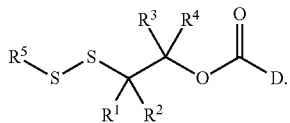

The method as in any embodiment above, wherein the protecting group, PG, is a protecting group suitable for thiol protection.

The method as in any embodiment above, wherein the protecting group, PG, is an acid labile protecting group.

The method as in any embodiment above, wherein the protecting group, PG, is selected from the group consisting of trityl, fluorenyl, dimethoxybenzyl, methoxybenzyl, 2, 4, 6-trimethyl benzyl, xanthenyl, ferrocenyl, methoxymethyl, isobutoxymethyl, and diphenylmethyl.

The method as in any embodiment above, wherein the protecting group, PG, is a trityl group.

The method as in any embodiment above, wherein the leaving group, LG, is a group suitable for displacement by a nucleophile.

The method as in any embodiment above, wherein the leaving group, LG, is a halogen.

The method as in any embodiment above, wherein the leaving group, LG, is a chlorine.

The method as in any embodiment above, wherein $R^5$ is a nitropyridine.

The method as in any embodiment above, wherein $R^5$ is 5-nitropyridine.

In embodiments, a compound of Formula III:

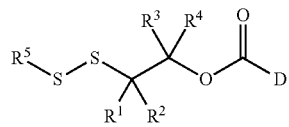

wherein, $R^1$, $R^2$, $R^3$, and $R^4$ are independently selected from the group consisting of H, optionally substituted branched or linear $C_1$-$C_5$ alkyl, and optionally substituted $C_3$-$C_6$ cycloalkyl, or $R^3$ and $R^4$ taken together with the carbon atom to which they are bound form a $C_3$-$C_6$ cycloalkyl ring, wherein said optionally substituted alkyl or cycloalkyl may be substituted with alkyl, cycloalkyl, aryl, heteroaryl, hydroxyl, nitrile, halo, alkoxy, haloalkoxy, arylalkoxy, acyloxy, alkylthio, sulfonate, amino, alkylamino, acylamino, carbamoyl, alkylcarbamoyl, or nitro;

$R^5$ is selected from the group consisting of optionally substituted pyridine and nitropyridine; and D is a biologically active molecule comprising a secondary nitrogen containing heteroaryl wherein the carbonyl in Formula III is covalently bonded to the secondary nitrogen in D.

As in any embodiment above, the compound wherein $R^5$ is 5-nitropyridine.

As in any embodiment above, the compound wherein $R^1$ is methyl and $R^2$, $R^3$, and $R^4$ are each H.

As in any embodiment above, the compound wherein $R^1$ is methyl and has R stereochemistry.

As in any embodiment above, wherein the compound of Formula III is selected from the group consisting of

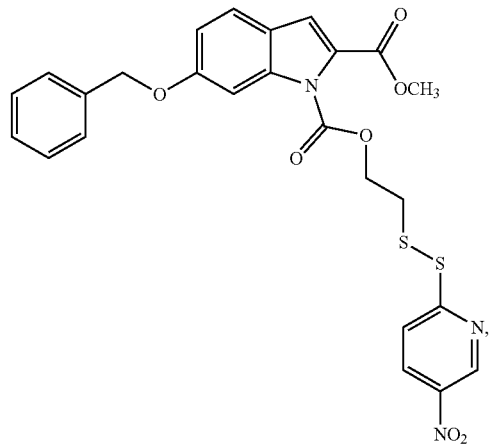

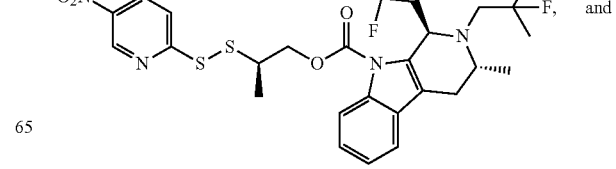

-continued

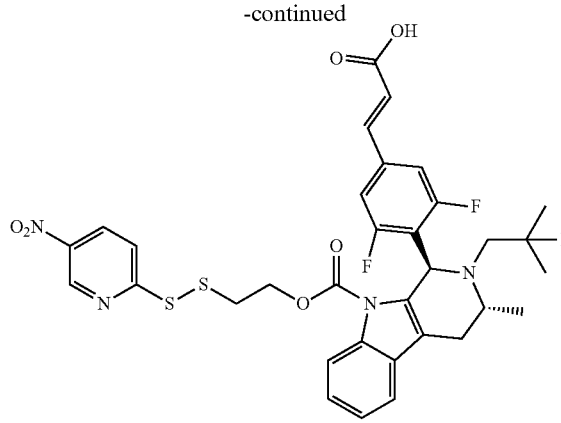

In embodiments, a method for preparing an antibody-drug conjugate of Formula IV:

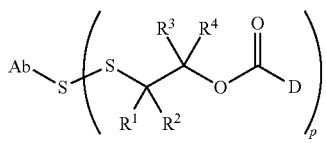

or a pharmaceutically acceptable salt thereof, wherein

Ab is an antibody;

$R^1$, $R^2$, $R^3$, and $R^4$ are independently selected from the group consisting of H, optionally substituted branched or linear $C_1$-$C_5$ alkyl, and optionally substituted $C_3$-$C_6$ cycloalkyl, or $R^3$ and $R^4$ taken together with the carbon atom to which they are bound form a $C_3$-$C_6$ cycloalkyl ring, wherein said optionally substituted alkyl or cycloalkyl may be substituted with alkyl, cycloalkyl, aryl, heteroaryl, hydroxyl, nitrile, halo, alkoxy, haloalkoxy, arylalkoxy, acyloxy, alkylthio, sulfonate, amino, alkylamino, acylamino, carbamoyl, alkylcarbamoyl, or nitro;

D is a biologically active molecule comprising a secondary nitrogen containing heteroaryl wherein the carbonyl in Formula IV is covalently bonded to the secondary nitrogen in D; and p is 1, 2, 3, 4, 5, 6, 7, 8, 9, or 10, and preferably 2;

the method comprising:

i. contacting a compound of Formula V:

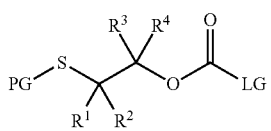

with a compound D, wherein LG is a leaving group and PG is a protecting group, to prepare a compound of Formula VI:

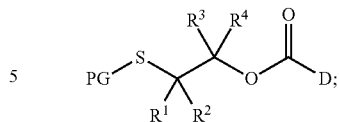

ii. contacting the compound of Formula VI with a disulfide $R^5$—S—S—$R^5$ under acidic conditions to prepare a compound of Formula III:

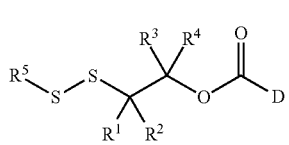

wherein $R^5$ is an optionally substituted pyridine; and iii. contacting a compound of Formula III with an antibody to prepare an antibody-drug conjugate of Formula IV.

In embodiments, a method for preparing a compound of Formula VII:

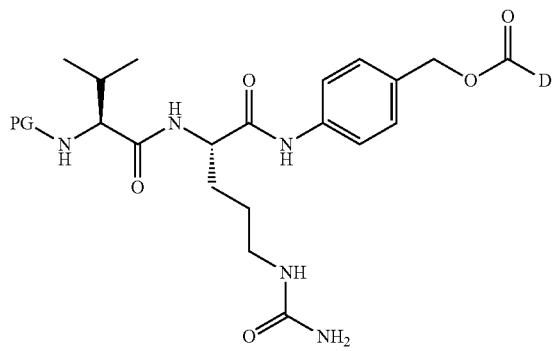

wherein

PG is a protecting group; and

D is a biologically active molecule comprising a secondary nitrogen containing heteroaryl wherein the ester carbonyl in Formula VII forms a carbamate with the secondary nitrogen in D;

the method comprising:

i. contacting a compound of Formula VIII

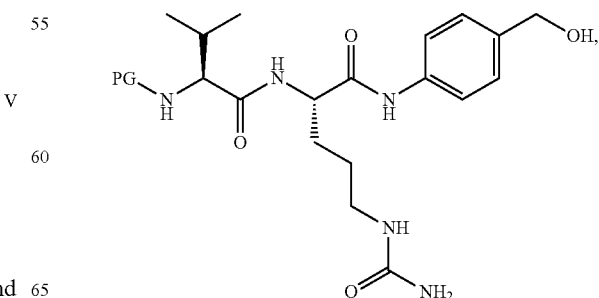

with a compound of Formula IX

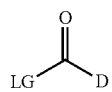

IX wherein LG is a leaving group, to prepare a compound of Formula VII.

The method as in any embodiment above, wherein the compound of Formula VII is

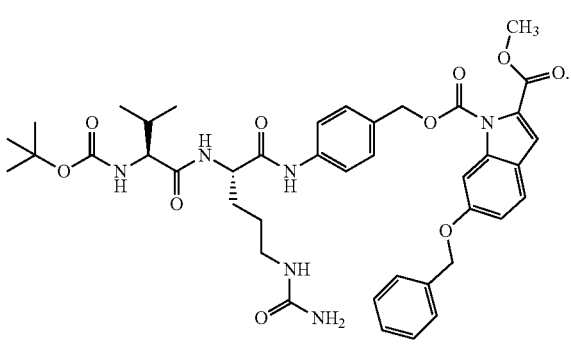 [SMILES: COC(=O)c1cc2ccc(OCc3ccccc3)cc2n1C(=O)OCc1ccc(NC(=O)[C@H](CCCNC(N)=O)NC(=O)[C@@H](NC(=O)OC(C)(C)C)C(C)C)cc1]

In an embodiment, the antibody-drug conjugate prepared by the method as in any embodiment above.

In an embodiment, a compound of Formula III prepared by the method as in any embodiment above.

The method as in any embodiment above, wherein said heteroaryl is selected from the group consisting of indole, indazole, benzimidazole, benzotriazole, pyrrole, pyrrolopyridine, imidazole, triazole, and tetrazoles.

The method as in any embodiment above, wherein said D is selected from the group consisting of cytotoxic agents; growth inhibitory agents; antibiotics; toxins; antitumor or anticancer agents; alkylating agents; alkyl sulfonates; aziridines; ethylenimines and methylamelamines; acetogenins; topoisomerase 1 inhibitors; proteosome inhibitors; EGFR inhibitors; tyrosine kinase inhibitors; serine-threonine kinase inhibitors; farnesyltransferase inhibitors; anti-hormonal agents; selective estrogen receptor modulators (SERMs); anti-estrogens; aromatase inhibitors; lutenizing hormone-releaseing hormone agonists; sex steroids; estrogens; and androgens/retinoids; estrogen receptor downregulators (ERDs); anti-androgens; immunosuppressive agents; non-steroidal anti-inflammatory drugs (NSAIDs); anti-inflammatory agents; cyclooxygenase inhibitors, leukotriene receptor antagonists, purine antagonists; steroids; dihydrofolate reductase inhibitors; and anti-malarial agents.

The method as in any embodiment above, wherein said D is selected from the group consisting of amanitin, vinblastine, vincristine, duocarmycin A, duocarmycin SA, CC-1065, adozelesin, U-76074, U-73073, carzelesin (U-80244), KW-2189, diazonamide A, esomeprazole, aripiprazole, valsartan, lansoprazole, rabeprazole, pometrexed, olmesartan, tadalafil, pantoprazole, candosartan, omeprazole, sunitinib, pemetrexed, alectinib, dacarbazine, semaxanib, dacinostat, dovitinib, mebendazole, and pimobendan.

Compounds can be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database). DTT refers to dithiothreitol. DHAA refers to dehydroascorbic acid.

Synthetic chemistry transformations and protecting group methodologies (protection and deprotection) useful in synthesizing compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$Ed., John Wiley and Sons (1999); and L. Paquette, ed., Encyclopedia of Reagents for Organic Synthesis, John Wiley and Sons (1995) and subsequent editions thereof.

Compounds may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus, according to a further aspect, there is provided a compound library comprising at least 2 compounds, or pharmaceutically acceptable salts thereof.

Methodologies for purifying antibodies are well-known in the art. Any known method can be used to purify antibodies, reduced antibodies and the like as described herein.

The General Procedures and Examples provide exemplary methods for preparing compounds. Those skilled in the art will appreciate that other synthetic routes may be used to synthesize the compounds. Although specific starting materials and reagents are depicted and discussed in the Schemes, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In general, the present subject matter describes a method for making an ADC in a manner such as General Scheme A:

SCHEME A

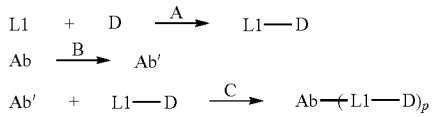

Reaction conditions:
A: A suitable base in a suitable solvent.
B: Reaction conditions providing free cysteine thiol(s) for reacting with the linker. In one embodiment, step B can comprise i) contacting Ab with a reducing agent, ii) purification of the reduced antibody, iii) contacting the purified antibody with an oxidizing agent to form Ab', and iv) purification of Ab'.
C: A suitable base in a suitable solvent.

Scheme 1 depicts a synthetic route for preparing a drug disulfide-linker molecule as described herein.
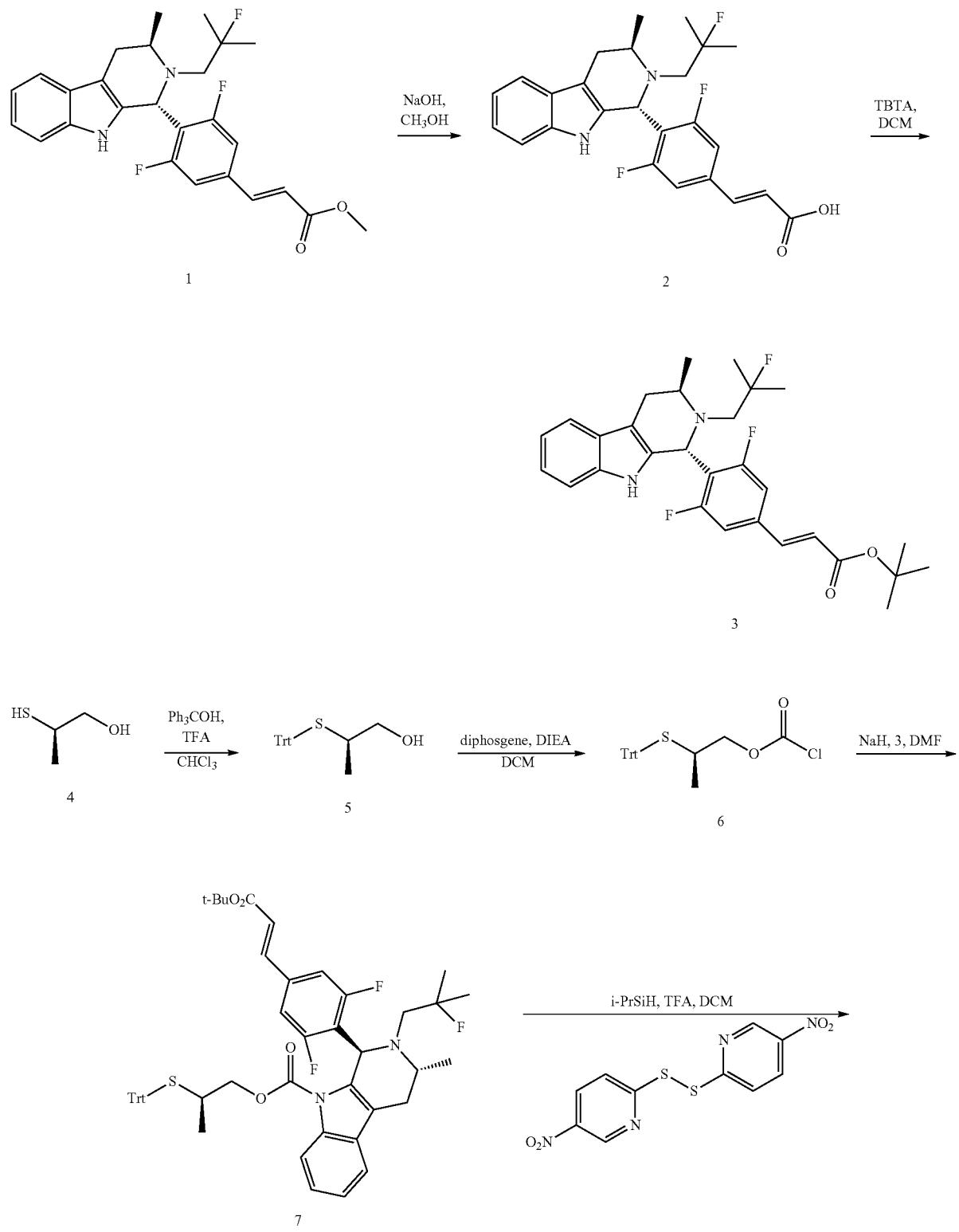

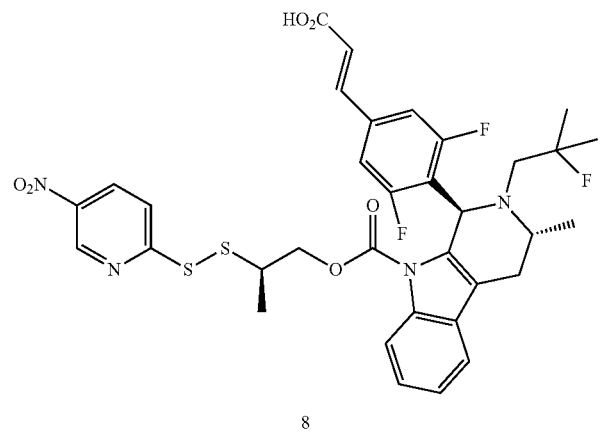
8
Scheme 2 depicts a synthetic route for preparing a drug disulfide-linker molecule as described herein.
SCHEME 2
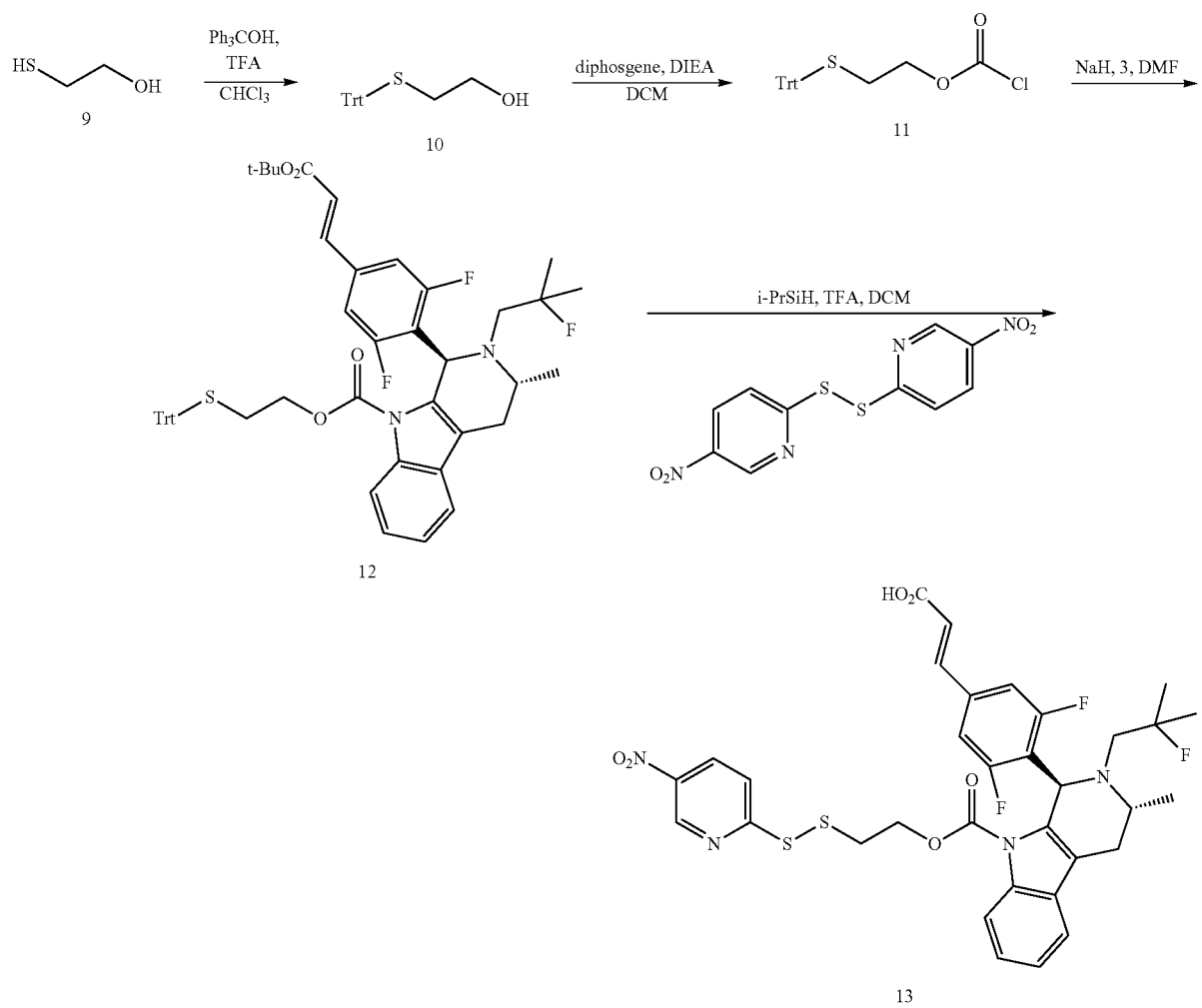

Scheme 3 depicts a synthetic route for preparing a drug-protected peptide linker molecule as described herein.
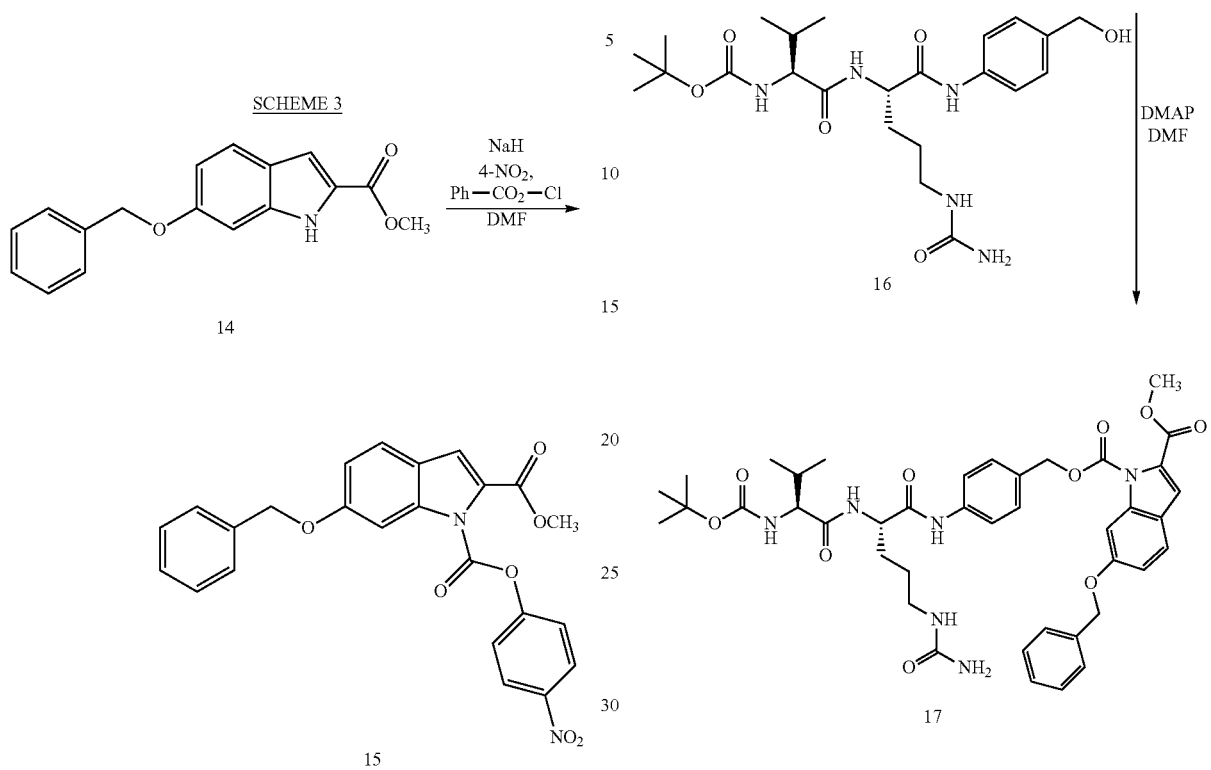
Scheme 4 depicts a synthetic route for preparing a drug-peptide linker.
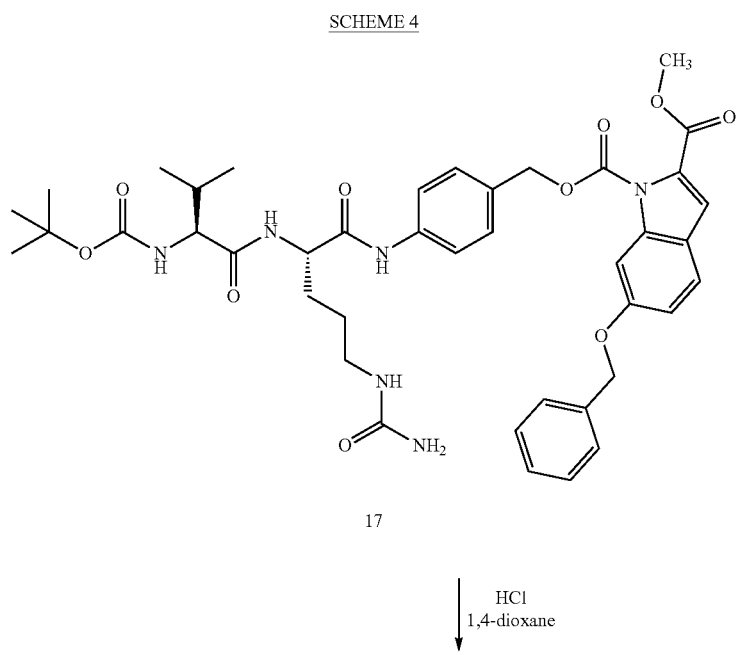

-continued

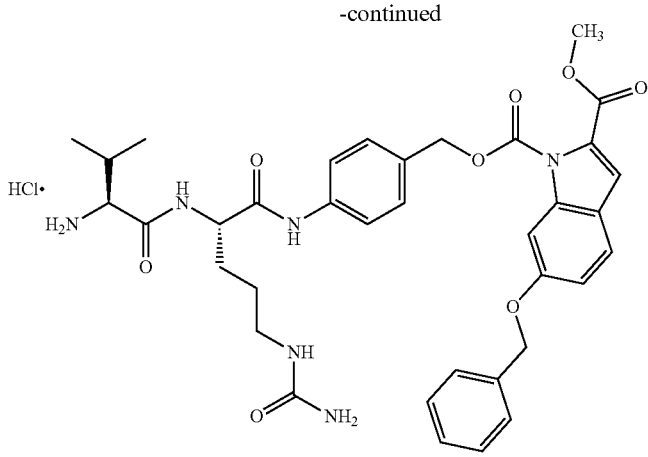

19

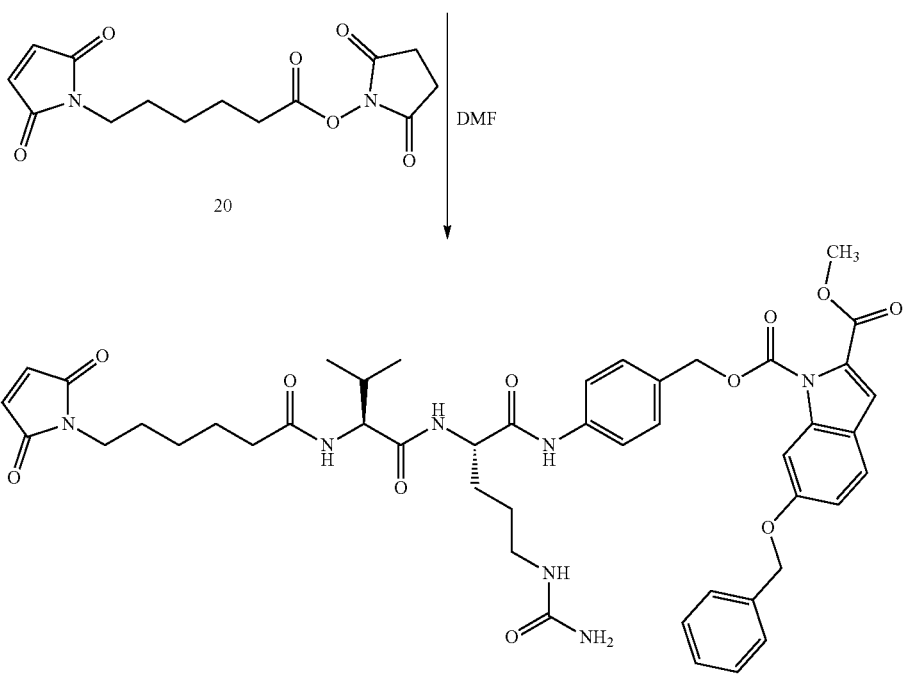

20

21

The ADCs described herein are composed of the following components:

1. Antibody (Ab)

As described herein, antibodies, e.g., a monoclonal antibodies (mABs) are used to deliver a drug to target cells, e.g., cells that express the specific protein that is targeted by the drug.

a. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See. e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991)). Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

b. Library-Derived Antibodies

Antibodies for use in an ADC may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

c. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer*, 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

d. Multispecific Antibodies

In certain embodiments, an antibody provided herein is a multispecific antibody, e.g. a bispecific antibody. The term "multispecific antibody" as used herein refers to an antibody comprising an antigen-binding domain that has polyepitopic specificity (i.e., is capable of binding to two, or more, different epitopes on one molecule or is capable of binding to epitopes on two, or more, different molecules).

In some embodiments, multispecific antibodies are monoclonal antibodies that have binding specificities for at least two different antigen binding sites (such as a bispecific antibody). In some embodiments, the first antigen-binding domain and the second antigen-binding domain of the multispecific antibody may bind the two epitopes within one and the same molecule (intramolecular binding). For example, the first antigen-binding domain and the second antigen-binding domain of the multispecific antibody may bind to two different epitopes on the same protein molecule. In certain embodiments, the two different epitopes that a multispecific antibody binds are epitopes that are not normally bound at the same time by one monospecific antibody, such as e.g. a conventional antibody or one immunoglobulin single variable domain. In some embodiments, the first antigen-binding domain and the second antigen-binding domain of the multispecific antibody may bind epitopes located within two distinct molecules (intermolecular binding). For example, the first antigen-binding domain of the multispecific antibody may bind to one epitope on one protein molecule, whereas the second antigen-binding domain of the multispecific antibody may bind to another epitope on a different protein molecule, thereby crosslinking the two molecules.

In some embodiments, the antigen-binding domain of a multispecific antibody (such as a bispecific antibody) comprises two VH/VL units, wherein a first VH/VL unit binds to a first epitope and a second VH/VL unit binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, and antibody fragments (such as Fab, Fv, dsFv, scFv, diabodies, bispecific diabodies and triabodies, antibody fragments that have been linked covalently or non-covalently). A VH/VL unit that further comprises at least a portion of a heavy chain variable region and/or at least a portion of a light chain variable region may also be referred to as an "arm" or "hemimer" or "half antibody." In some embodiments, a hemimer comprises a sufficient portion of a heavy chain variable region to allow intramolecular disulfide bonds to be formed with a second hemimer. In some embodiments, a hemimer comprises a knob mutation or a hole mutation, for example, to allow heterodimerization with a second hemimer or half antibody that comprises a complementary hole mutation or knob mutation. Knob mutations and hole mutations are discussed further below.

In certain embodiments, a multispecific antibody provided herein may be a bispecific antibody. The term "bispecific antibody" as used herein refers to a multispecific antibody comprising an antigen-binding domain that is capable of binding to two different epitopes on one molecule or is capable of binding to epitopes on two different molecules. A bispecific antibody may also be referred to herein as having "dual specificity" or as being "dual specific." Exemplary bispecific antibodies may bind both protein and any other antigen. In certain embodiments, one of the binding specificities is for protein and the other is for CD3. See, e.g., U.S. Pat. No. 5,821,337. In certain embodiments, bispecific antibodies may bind to two different epitopes of the same protein molecule. In certain embodiments, bispecific antibodies may bind to two different epitopes on two different protein molecules. Bispecific antibodies may also be used to localize cytotoxic agents to cells which express protein. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983), WO 93/08829, and Traunecker et al., *EMBO J.* 10: 3655 (1991)), and "knob-in-hole" engineering (see, e.g., U.S. Pat. No. 5,731,168, WO2009/089004, US2009/0182127, US2011/0287009, Marvin and Zhu, Acta Pharmacol. Sin. (2005) 26(6):649-658, and Kontermann (2005) Acta Pharmacol. Sin., 26:1-9). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see. e.g., US 2011/0287009, US2007/0178552, WO 96/027011, WO 98/050431, Zhu et al., 1997, *Protein Science* 6:781-788, and WO2012/106587). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

The term "hole mutation" as used herein refers to a mutation that introduces a cavity (hole) into a polypeptide at an interface in which the polypeptide interacts with another polypeptide. In some embodiments, the other polypeptide has a knob mutation.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W (EU numbering). In some embodiments, a hole mutation in an IgG1 constant region comprises one or more mutations selected from T366S, L368A and Y407V (EU numbering). In some embodiments, a hole mutation in an IgG1 constant region comprises T366S, L368A and Y407V (EU numbering).

In some embodiments, a knob mutation in an IgG4 constant region is T366W (EU numbering). In some embodiments, a hole mutation in an IgG4 constant region comprises one or more mutations selected from T366S, L368A, and Y407V (EU numbering). In some embodiments, a hole mutation in an IgG4 constant region comprises T366S, L368A, and Y407V (EU numbering).

Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies" or "dual-variable domain immunoglobulins" (DVDs) are also included herein (see, e.g., US 2006/0025576A1, and Wu et al. Nature Biotechnology (2007)).). The antibody or fragment herein also includes a "Dual Acting FAb" or "DAF" comprising an antigen binding site that binds to a target protein as well as another, different antigen (see, US 2008/0069820, for example).

e. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Pluckthin, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

f. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

i. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

Amino acid substitutions.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, lie;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hot-spots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

ii. Cysteine Engineered Antibody Variants

In certain embodiments, it may be desirable to create cysteine engineered antibodies, e.g., "THIOMAB™ antibody," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drugs or a Linker L1-drug intermediates, to create an ADC, as described further herein. In certain embodiments, any one or more of the following residues may be substituted with cysteine: V205 (Kabat numbering) of the light chain; A140 (EU numbering) of the heavy chain; L174 (EU numbering) of the heavy chain; Y373 (EU numbering) of the heavy chain; K149 (Kabat numbering) of the light chain; A118 (EU numbering) of the heavy chain; and S400 (EU numbering) of the heavy chain Fc region. In specific embodiments, the antibodies described herein comprise the HC-A140C (EU numbering) cysteine substitution. In specific embodiments, the antibodies described herein comprise the LC-K149C (Kabat numbering) cysteine substitution. In specific embodiments, the antibodies described herein comprise the HC-A118C (EU numbering) cysteine substitution.

Cysteine engineered antibodies may be generated as described, e.g., in U.S. Pat. No. 7,521,541.

In certain embodiments, the antibody comprises one of the following heavy chain cysteine substitutions:

TABLE 2

HC Cysteine Substitutions.

| Chain (HC/LC) | Residue | EU Mutation Site # | Kabat Mutation Site # |
|---|---|---|---|
| HC | T | 114 | 110 |
| HC | A | 140 | 136 |
| HC | L | 174 | 170 |
| HC | L | 179 | 175 |
| HC | T | 187 | 183 |
| HC | T | 209 | 205 |
| HC | V | 262 | 258 |
| HC | G | 371 | 367 |
| HC | Y | 373 | 369 |
| HC | E | 382 | 378 |
| HC | S | 424 | 420 |
| HC | N | 434 | 430 |
| HC | Q | 438 | 434 |

In certain embodiments, the antibody comprises one of the following light chain cysteine substitutions:

TABLE 3

LC Cysteine Substitutions.

| Chain (HC/LC) | Residue | EU Mutation Site # | Kabat Mutation Site # |
|---|---|---|---|
| LC | I | 106 | 106 |
| LC | R | 108 | 108 |
| LC | R | 142 | 142 |
| LC | K | 149 | 149 |
| LC | V | 205 | 205 |

A nonlimiting exemplary hu7C2.v2.2.LA light chain (LC) K149C THIOMAB™ antibody has the heavy chain and light chain amino acid sequences of SEQ ID NOs: 26 and 30, respectively. A nonlimiting exemplary hu7C2.v2.2.LA heavy chain (HC) A118C THIOMAB™ antibody has the heavy chain and light chain amino acid sequences of SEQ ID NOs: 31 and 25, respectively.

ADCs include cysteine engineered antibodies where one or more amino acids of a wild-type or parent antibody are replaced with a cysteine amino acid. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies for use in an ADC are in the ranges of 0.6 to 1.0; 0.7 to 1.0; or 0.8 to 1.0.

To prepare a cysteine engineered antibody by mutagenesis, DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249, Shen et al (2012) Nature Biotech., 30(2): 184-191; Junutula et al (2008) Jour of Immun. Methods 332:41-52). The engineered cysteine thiols may react with linker reagents or the Linker-Drug intermediates described herein, which have thiol-reactive, electrophilic groups such as maleimide or alpha-halo amides to form an ADC with cysteine engineered antibodies (ThioMabs) and the drug residue. The location of the drug moiety can thus be designed, controlled, and known. Drug/antibody ratio ("PAR") can be controlled since the engineered cysteine thiol groups typically react with thiol-reactive linker reagents or linker-drug intermediates in high yield. Engineering an antibody to introduce a cysteine amino acid by substitution at a single site on the heavy or light chain gives two new cysteines on the symmetrical antibody. A PAR of about 2 can be achieved and near homogeneity of the conjugation product.

Cysteine engineered antibodies preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signaling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

Cysteine engineered antibodies are prepared for conjugation with linker or linker-drug intermediates by reduction and reoxidation of intrachain disulfide groups.

iii. Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

iv. Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the subject matter described herein is directed to an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166: 1351-1361 (1987)).

Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci.* USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

In some embodiments, one or more amino acid modifications may be introduced into the Fc portion of the antibody provided herein in order to increase IgG binding to the neonatal Fc receptor. In certain embodiments, the antibody comprises the following three mutations according to EU numbering: M252Y, S254T, and T256E (the "YTE mutation") (U.S. Pat. No. 8,697,650; see also Dall'Acqua et al., Journal of Biological Chemistry 281(33):23514-23524 (2006). In certain embodiments, the YTE mutation does not affect the ability of the antibody to bind to its cognate antigen. In certain embodiments, the YTE mutation increases the antibody's serum half-life compared to the native (i.e., non-YTE mutant) antibody. In some embodiments, the YTE mutation increases the serum half-life of the antibody by 3-fold compared to the native (i.e., non-YTE mutant) antibody. In some embodiments, the YTE mutation increases the serum half-life of the antibody by 2-fold compared to the native (i.e., non-YTE mutant) antibody. In some embodiments, the YTE mutation increases the serum half-life of the antibody by 4-fold compared to the native (i.e., non-YTE mutant) antibody. In some embodiments, the YTE mutation increases the serum half-life of the antibody by at least 5-fold compared to the native (i.e., non-YTE mutant) antibody. In some embodiments, the YTE mutation increases the serum half-life of the antibody by at least 10-fold compared to the native (i.e., non-YTE mutant) antibody. See, e.g., U.S. Pat. No. 8,697,650; see also Dall'Acqua et al., Journal of Biological Chemistry 281(33): 23514-23524 (2006).

In certain embodiments, the YTE mutant provides a means to modulate antibody-dependent cell-mediated cytotoxicity (ADCC) activity of the antibody. In certain embodiments, the YTEO mutant provides a means to modulate ADCC activity of a humanized IgG antibody directed against a human antigen. See, e.g., U.S. Pat. No. 8,697,650; see also Dall'Acqua et al., Journal of Biological Chemistry 281(33):23514-23524 (2006).

In certain embodiments, the YTE mutant allows the simultaneous modulation of serum half-life, tissue distribution, and antibody activity (e.g., the ADCC activity of an IgG antibody). See, e.g., U.S. Pat. No. 8,697,650; see also Dall'Acqua et al., Journal of Biological Chemistry 281(33): 23514-23524 (2006).

Antibodies with reduced effector function include those with substitution of one or more of Fc region residues 238, 265, 269, 270, 297, 327 and 329 according to EU numbering (U.S. Pat. No. 6,737,056). Such Fc mutants include Fc mutants with substitutions at two or more of amino acid positions 265, 269, 270, 297 and 327 according to EU numbering, including the so-called "DANA" Fc mutant with substitution of residues 265 and 297 to alanine according to EU numbering (i.e., D265A and N297A according to EU numbering) (U.S. Pat. No. 7,332,581). In certain embodiments the Fc mutant comprises the following two amino acid substitutions: D265A and N297A. In certain embodiments the Fc mutant consists of the following two amino acid substitutions: D265A and N297A.

In certain embodiments, the proline at position 329 (EU numbering) (P329) of a wild-type human Fc region is substituted with glycine or arginine or an amino acid residue large enough to destroy the proline sandwich within the Fc/Fcγ receptor interface, that is formed between the P329 of the Fc and tryptophane residues W87 and W110 of FcgRIII (Sondermann et al.: Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region, all according to EU numbering (U.S. Pat. No. 8,969,526 which is incorporated by reference in its entirety).

In certain embodiments, a polypeptide comprises the Fc variant of a wild-type human IgG Fc region wherein the polypeptide has P329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU numbering (U.S. Pat. No. 8,969,526 which is incorporated by reference in its entirety). In certain embodiments, the polypeptide comprising the P329G, L234A and L235A (EU numbering) substitutions exhibit a reduced affinity to the human FcγRIIIA and FcγRIIA, for down-modulation of ADCC to at least 20% of the ADCC induced by the polypeptide comprising the wild-type human IgG Fc region, and/or for down-modulation of ADCP (U.S. Pat. No. 8,969,526 which is incorporated by reference in its entirety).

In a specific embodiment the polypeptide comprising an Fc variant of a wild-type human Fc polypeptide comprises a triple mutation: an amino acid substitution at position Pro329, a L234A and a L235A mutation according to EU numbering (P329/LALA) (U.S. Pat. No. 8,969,526 which is incorporated by reference in its entirety). In specific embodiments, the polypeptide comprises the following amino acid substitutions: P329G, L234A, and L235A according to EU numbering.

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826) according to EU numbering. See also Duncan & Winter, Nature 322:738-40 (1988); U.S. Pat. Nos. 5,648,260; 5,624,821; and WO 94/29351 concerning other examples of Fc region variants.

g. Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)

polyethylene glycol, propylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

h. Tumor-Associated Antigens

Antibodies, including but not limited to cysteine engineered antibodies, which may be useful in the ADCs described herein in the treatment of cancer include, but are not limited to, antibodies against cell surface receptors and tumor-associated antigens (TAA). Certain tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to more specifically target cancer cells for destruction via antibody-based therapies.

Examples of tumor-associated antigens TAA include, but are not limited to, those listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA listed below are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, and/or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

i. Recombinant Methods and Compositions

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977); baby hamster kidney cells (BHK); mouse sertoli cells (TM4 cells as described, e.g., in *Mather, Biol. Reprod.* 23:243-251 (1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Figure 4:
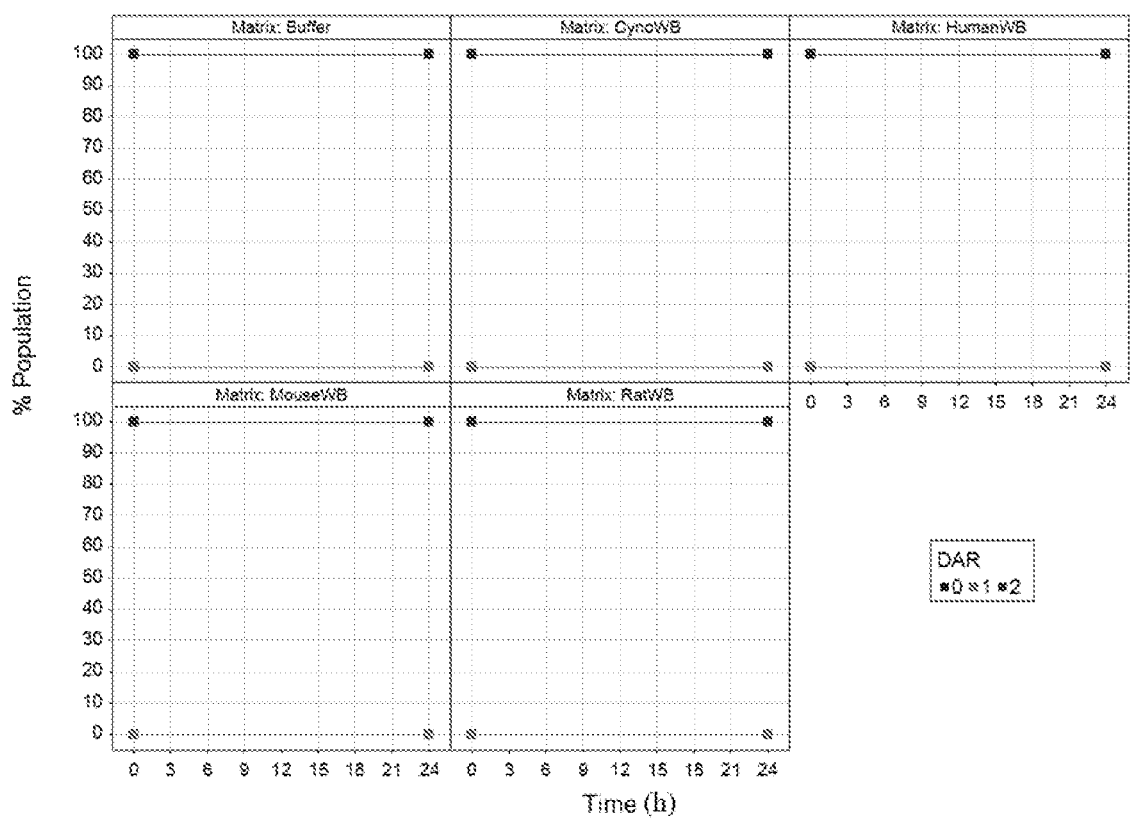
FIG. 4 is a set of graphs showing the stability of CNJ-3 measured over 24 h in buffer and in whole blood from various species. DAR=antibody-drug conjugate with indicated drug antibody ratio.

Referring now to antibody affinity, in embodiments, the antibody binds to one or more tumor-associated antigens or cell-surface receptors selected from (1)-(53):

(1) BMPR1B (bone morphogenetic protein receptor-type IB, Genbank accession no. NM_001203)
ten Dijke, P., et al Science 264 (5155):101-104 (1994), Oncogene 14 (11):1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377 (Page 349-350); WO200230268 (Claim 27; Page 376); WO200148204 (Example; FIG. 4);
NP_001194 bone morphogenetic protein receptor, type IB/pid=NP_001194.1 Cross-references: MIM:603248; NP_001194.1; AY065994

Figure 3:
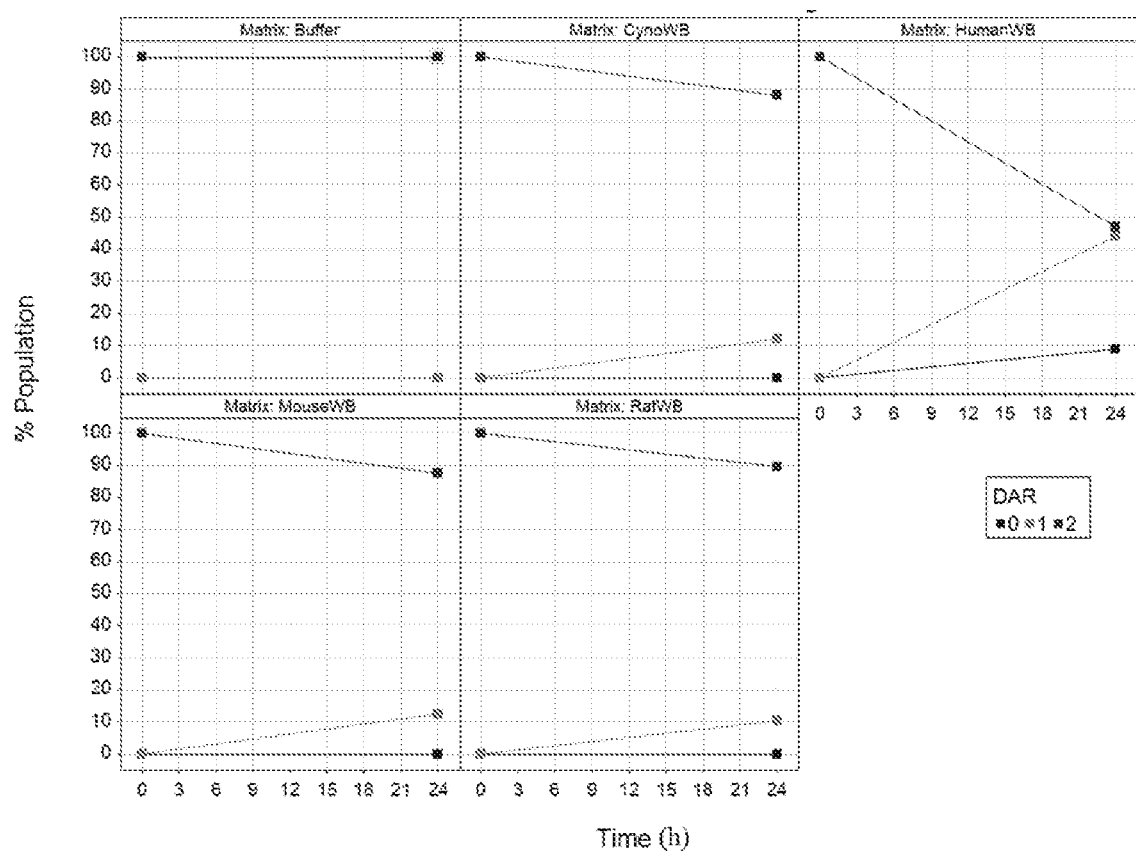
FIG. 3 is a set of graphs showing the stability of CNJ-1 measured over 24 h in buffer and in whole blood from various species. DAR=antibody-drug conjugate with indicated drug antibody ratio.

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150);
NP_003477 solute carrier family 7 (cationic amino acid transporter, y+system), member 5/pid=NP_003477.3—*Homo sapiens*
Cross-references: MIM:600182; NP_003477.3; NM_015923; NM_003486_1

Figure 2:
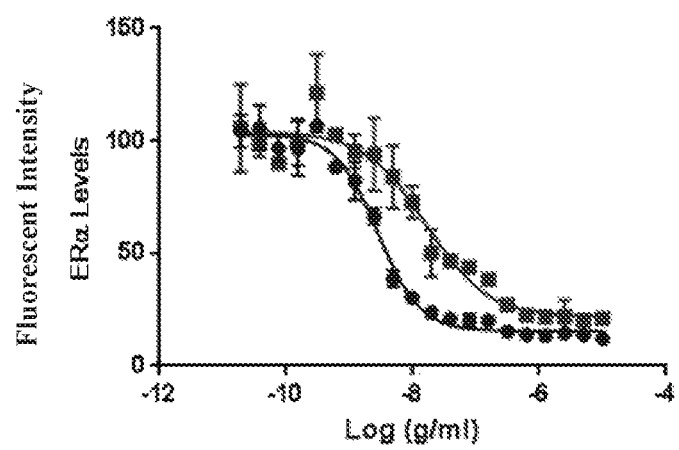
FIG. 2 is a graph showing the reduction of ERα levels in MCF7-neo/HER2 cells treated with either CNJ-3 (HER2, circles) or CNJ-4 (B7H4, squares).

(3) STEAP1 (six transmembrane epithelial antigen of prostate, Genbank accession no. NM_012449)
Cancer Res. 61 (15), 5857-5860 (2001), Hubert, R. S., et al (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A);
NP_036581 six transmembrane epithelial antigen of the prostate
Cross-references: MIM:604415; NP_036581.1; NM_012449_1

(4) 0772P (CA125, MUC16, Genbank accession no. AF361486) J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); U.S. Pat. No. 798,959.
Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1

(6) Napi2b (Napi3b, NAPI-3B, NPTIIb, SLC34A2, solute carrier family 34 (sodium phosphate), member 2, type II sodium-dependent phosphate transporter 3b, Genbank accession no. NM_006424)
J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140); Cross-references: MIM:604217; NP 006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878)
Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC: 10737;

(8) PSCA hlg (2700050C12Rik, C530008O16Rik, RIKEN cDNA 2700050C12, RIKEN cDNA 2700050C12 gene, Genbank accession no. AY358628); Ross et al (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20);
Cross-references: GI:37182378; AAQ88991.1; AY358628_1

(9) ETBR (Endothelin type B receptor, Genbank accession no. AY275463);
Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-

Figure 6:
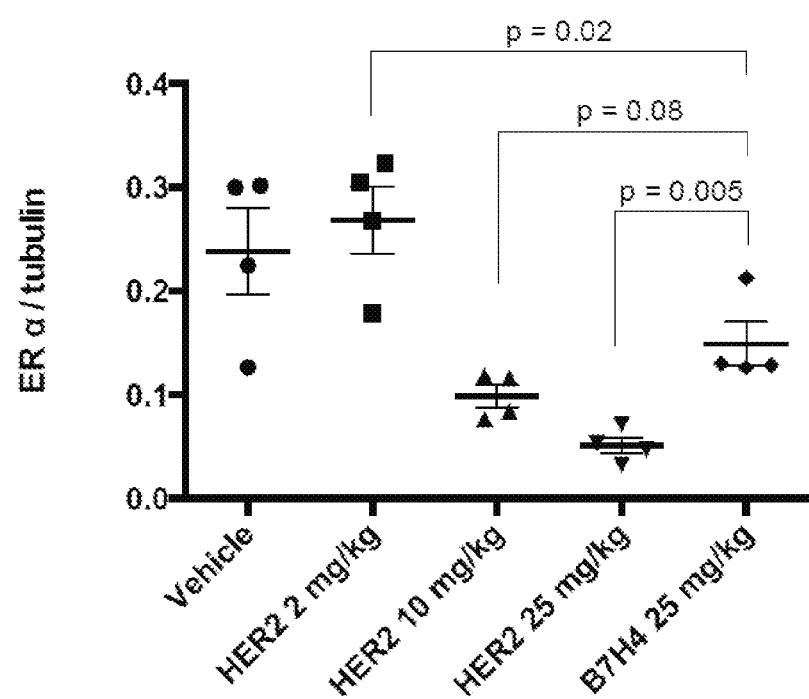
FIG. 6 is a graph showing the reduction of ERα levels in MCF7-neo/HER2 tumors in mice following single IV treatment with either CNJ-3 (HER2) or CNJ-4 (B7H4); alternate statistical analysis. Timepoint=day 4. Error bars=standard error of the mean.

3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004;

(10) MSG783 (RNF124, hypothetical protein FLJ20315, Genbank accession no. NM_017763);

WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6); Cross-references: LocusID:54894: NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138)

Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10); Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636)

Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212)

Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2);

Cross-references: MIM: 187395; NP 003203.1; NM_003212_1

(14) CD21 (CR2 (Complement receptor 2) or C3DR (C3d/Epstein Barr virus receptor) or Hs.73792 Genbank accession no. M26004)

Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIGS. 9.1-9.9); WO2004020595 (Claim 1); Accession: P20023; Q13866; Q14212; EMBL; M26004; AAA35786.1.

(15) CD79b (CD79B, CD7913, IGb (immunoglobulin-associated beta), B29, Genbank accession no. NM_000626 or 11038674)

Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146);

Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130)

Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25);

Cross-references: MIM:606509; NP_110391.2; NM_030764_1

(17) HER2 (ErbB2, Genbank accession no. M11730)

Figure 5:
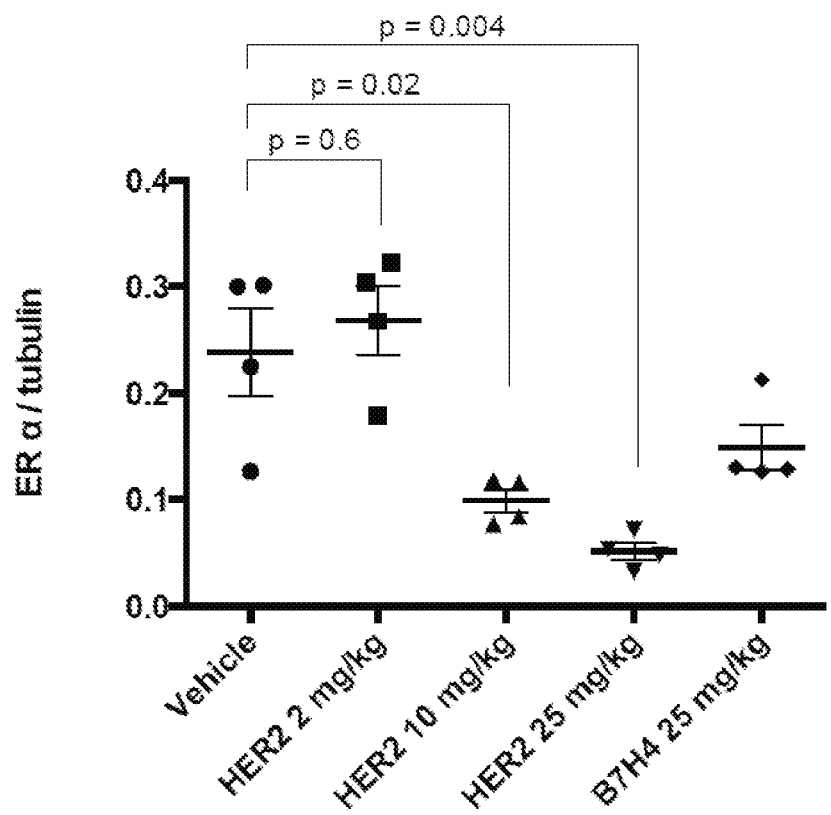
FIG. 5 is a graph showing the reduction of ERα levels in MCF7-neo/HER2 tumors in mice following single IV treatment with either CNJ-3 (HER2) or CNJ-4 (B7H4). Timepoint=day 4. Error bars=standard error of the mean.

Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4);

Accession: P04626; EMBL; M11767; AAA35808.1. EMBL; M11761; AAA35808.1.

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427), WO200260317 (Claim 2);
Accession: P40199; Q14920; EMBL; M29541; AAA59915.1. EMBL; M18728;

(19) MDP (DPEP1, Genbank accession no. BC017023) Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9);
Cross-references: MIM: 179780; AAH17023.1; BC017023_1

(20) IL20Rα (IL20Ra, ZCYTOR7, Genbank accession no. AF184971);
Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF184971; AAF01320.1.

(21) Brevican (BCAN, BEHAB, Genbank accession no. AF229053)
Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);

(22) EphB2R (DRT, ERK, Hek5, EPHT3, Tyro5, Genbank accession no. NM_004442)
Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42);
Cross-references: MIM:600997; NP_004433.2; NM_004442_1

(23) ASLG659 (B7h, Genbank accession no. AX092328) US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;

(24) PSCA (Prostate stem cell antigen precursor, Genbank accession no. AJ297436)
Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B);
Accession: 043653; EMBL; AF043498; AAC39607.1.

(25) GEDA (Genbank accession No. AY260763); AAP14954 lipoma HMGIC fusion-partner-like protein/ pid=AAP14954.1—*Homo sapiens*
Species: *Homo sapiens* (human); WO2003054152 (Claim 20); WO2003000842 (Claim 1); WO2003023013 (Example 3, Claim 20); US2003194704 (Claim 45);
Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP_443177.1—*Homo sapiens*
Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3); Cross-references: MIM:606269; NP_443177.1; NM_052945_1; AF132600 (27) CD22 (B-cell receptor CD22-B isoform, BL-CAM, Lyb-8, Lyb8, SIGLEC-2, FLJ22814, Genbank accession No. AK026467); Wilson et al (1991) J. Exp. Med. 173:137-146; WO2003072036 (Claim 1, FIG. 1);
Cross-references: MIM:107266; NP 001762.1; NM_001771_1

(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10)
WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464; (29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1)
WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+ T lymphocytes); 273 aa, pI: 6.56 MW: 30820 TM: 1 [P] Gene Chromosome: 6p21.3, Genbank accession No. NP_002111.1)

Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2)

Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession No. NP_001773.1) WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1)

US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1)

WO2003077836; WO200138490 (claim 6, FIG. 18E-1-18-E-2); Davis et al (2001) Proc. Natl. Acad. Sci USA 98(17): 9772-9777; WO2003089624 (claim 8); EP1347046 (claim 1); WO2003089624 (claim 7);

(35) FCRH5 (IRTA2, Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085; Mouse:AK089756, AY158090, AY506558; NP 112571.1 WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436 WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2): 178-84;

(37) PMEL17 (silver homolog; SILV; D12S53E; PMEL17; SI; SIL); ME20; gp100) BC001414; BT007202; M32295; M77348; NM_006928; McGlinchey, R. P. et al (2009) Proc. Natl. Acad. Sci. U.S.A. 106 (33), 13731-13736; Kummer, M. P. et al (2009) J. Biol. Chem. 284 (4), 2296-2306;

(38) TMEFF1 (transmembrane protein with EGF-like and two follistatin-like domains 1; Tomoregulin-1); H7365; C9orf2; C9ORF2; U19878; X83961; NM_080655; NM_003692; Harms, P. W. (2003) Genes Dev. 17 (21), 2624-2629; Gery, S. et al (2003) Oncogene 22 (18):2723-2727;

(39) GDNF-Ra1 (GDNF family receptor alpha 1; GFRA1; GDNFR; GDNFRA; RETL1; TRNR1; RET1L; GDNFR-alpha1; GFR-ALPHA-1); U95847; BC014962; NM_145793 NM_005264; Kim, M. H. et al (2009) Mol. Cell. Biol. 29 (8), 2264-2277; Treanor, J. J. et al (1996) Nature 382 (6586):80-83;

(40) Ly6E (lymphocyte antigen 6 complex, locus E, Ly67, RIG-E, SCA-2, TSA-1); NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952; WO 2013/17705;

(41) TMEM46 (shisa homolog 2 (*Xenopus laevis*); SHISA2); NP_001007539.1; NM_001007538.1; Furushima, K. et al (2007) Dev. Biol. 306 (2), 480-492; Clark, H. F. et al (2003) Genome Res. 13 (10):2265-2270;

(42) Ly6G6D (lymphocyte antigen 6 complex, locus G6D; Ly6-D, MEGT1); NP_067079.2; NM_021246.2; Mallya, M. et al (2002) Genomics 80 (1):113-123; Ribas, G. et al (1999) J. Immunol. 163 (1):278-287;

(43) LGR5 (leucine-rich repeat-containing G protein-coupled receptor 5; GPR49, GPR67); NP_003658.1; NM_003667.2; Salanti, G. et al (2009) Am. J. Epidemiol. 170 (5):537-545; Yamamoto, Y. et al (2003) Hepatology 37 (3):528-533;

(44) RET (ret proto-oncogene; MEN2A; HSCR1; MEN2B; MTC1; PTC; CDHF12; Hs. 168114; RET51; RET-ELE1); NP_066124.1; NM_020975.4; Tsukamoto, H. et al (2009)

Cancer Sci. 100 (10):1895-1901; Narita, N. et al (2009) Oncogene 28 (34):3058-3068;

(45) LY6K (lymphocyte antigen 6 complex, locus K; LY6K; HSJ001348; FLJ35226); NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;

(46) GPR19 (G protein-coupled receptor 19; Mm.4787); NP_006134.1; NM_006143.2; Montpetit, A. and Sinnett, D. (1999) Hum. Genet. 105 (1-2):162-164; O'Dowd, B. F. et al (1996) FEBS Lett. 394 (3):325-329;

(47) GPR54 (KISS1 receptor; KISS1R; GPR54; HOT7T175; AXOR12); NP_115940.2; NM_032551.4; Navenot, J. M. et al (2009) Mol. Pharmacol. 75 (6):1300-1306; Hata, K. et al (2009) Anticancer Res. 29 (2):617-623;

(48) ASPHD1 (aspartate beta-hydroxylase domain containing 1; LOC253982); NP_859069.2; NM_181718.3; Gerhard, D. S. et al (2004) Genome Res. 14 (10B):2121-2127;

(49) Tyrosinase (TYR; OCAIA; OCA1A; tyrosinase; SHEP3); NP_000363.1; NM_000372.4; Bishop, D. T. et al (2009) Nat. Genet. 41 (8):920-925; Nan, H. et al (2009) Int. J. Cancer 125 (4):909-917;

(50) TMEM118 (ring finger protein, transmembrane 2; RNFT2; FLJ14627); NP_001103373.1; NM_001109903.1; Clark, H. F. et al (2003) Genome Res. 13 (10):2265-2270; Scherer, S. E. et al (2006) Nature 440 (7082):346-351

(51) GPR172A (G protein-coupled receptor 172A; GPCR41; FLJ11856; D15Ertd747e); NP_078807.1; NM_024531.3; Ericsson, T. A. et al (2003) Proc. Natl. Acad. Sci. U.S.A. 100 (11):6759-6764; Takeda, S. et al (2002) FEBS Lett. 520 (1-3):97-101.

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) *J. Clin. Invest.* 75:756-56; Andrews et al., (1986) *Blood* 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signalling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al., (2007) Blood 110 (7):2659-66; Chen C H, et al. (2006) Blood 107 (4):1459-67; Marshall A S, et al. (2006) Eur. J. Immunol. 36 (8):2159-69; Bakker A B, et al (2005) Cancer Res. 64 (22):8443-50; Marshall A S, et al (2004) J. Biol. Chem. 279 (15):14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

As described herein, an ADC comprises an antibody, e.g., an antibody selected from:

Anti-Ly6E Antibodies

In certain embodiments, an ADC can comprise anti-Ly6E antibodies. Lymphocyte antigen 6 complex, locus E (Ly6E), also known as retinoic acid induced gene E (RIG-E) and stem cell antigen 2 (SCA-2). It is a GPI linked, 131 amino acid length, ~8.4 kDa protein of unknown function with no known binding partners. It was initially identified as a transcript expressed in immature thymocyte, thymic medullary epithelial cells in mice (Mao, et al. (1996) *Proc. Natl. Acad. Sci. U.S.A.* 93:5910-5914). In some embodiments, the subject matter described herein provides an ADC comprising an anti-Ly6E antibody described in PCT Publication No. WO 2013/177055.

In some embodiments, the subject matter described herein provides an ADC comprising an anti-Ly6E antibody comprising at least one, two, three, four, five, or six HVRs selected from (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In one aspect, the subject matter described herein provides an ADC comprising an antibody that comprises at least one, at least two, or all three VH HVR sequences selected from (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14. In a further embodiment, the antibody comprises (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14.

In another aspect, the subject matter described herein provides an ADC comprising an antibody that comprises at least one, at least two, or all three VL HVR sequences selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In one embodiment, the antibody comprises (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, an ADC comprises an antibody comprising (a) a VH domain comprising at least one, at least two, or all three VH HVR sequences selected from (i) HVR-H1 comprising the amino acid sequence of SEQ ID NO: 12, (ii) HVR-H2 comprising the amino acid sequence of SEQ ID NO: 13, and (iii) HVR-H3 comprising an amino acid sequence selected from SEQ ID NO: 14; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 11.

In another aspect, the subject matter described herein provides an ADC comprising an antibody that comprises (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In any of the above embodiments, an anti-Ly6E antibody of an ADC is humanized. In one embodiment, an anti-Ly6E antibody comprises HVRs as in any of the above embodiments, and further comprises a human acceptor framework, e.g. a human immunoglobulin framework or a human consensus framework.

In another aspect, an anti-Ly6E antibody of an ADC comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 8. In certain embodiments, a VH sequence having at least 90%, 91%, 92%, 93%, 94%, 95%, 96%, 97%, 98%, or 99% identity to the amino acid sequence of SEQ ID NO:8 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 8. In certain embodiments, a total of 1 to 5 amino acids have been substituted, inserted and/or deleted in SEQ ID NO: 8. In certain embodiments, substitutions, insertions, or deletions occur in regions outside the HVRs (i.e., in the FRs). Optionally, the anti-Ly6E antibody comprises the VH sequence of SEQ ID NO: 8, including post-translational modifications of that sequence. In a particular embodiment, the VH comprises one, two or three HVRs selected from: (a) HVR-H1 comprising the amino acid sequence of SEQ ID NO: 12, (b) HVR-H2 comprising the amino acid sequence of SEQ ID NO: 13, and (c) HVR-H3 comprising the amino acid sequence of SEQ ID NO: 14.

In another aspect, an anti-Ly6E antibody of an ADC is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 7. In certain embodiments, a VL sequence having at least 90%, 91%, 92%, 93%, 94%, 95%, 96%, 97%, 98%, or 99% identity to the amino acid sequence of SEQ ID NO:7 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 7. In certain embodiments, a total of 1 to 5 amino acids have been substituted, inserted and/or deleted in SEQ ID NO: 7. In certain embodiments, the substitutions, insertions, or deletions occur in regions outside the HVRs (i.e., in the FRs). Optionally, the anti-Ly6E antibody comprises the VL sequence of SEQ ID NO: 7, including post-translational modifications of that sequence. In a particular embodiment, the VL comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, an ADC comprising an anti-Ly6E antibody is provided, wherein the antibody comprises a VH as in any of the embodiments provided above, and a VL as in any of the embodiments provided above.

In one embodiment, an ADC is provided, wherein the antibody comprises the VH and VL sequences in SEQ ID NO: 8 and SEQ ID NO: 7, respectively, including post-translational modifications of those sequences.

In a further aspect, provided herein are ADCs comprising antibodies that bind to the same epitope as an anti-Ly6E antibody provided herein. For example, in certain embodiments, an ADC is provided comprising an antibody that binds to the same epitope as an anti-Ly6E antibody comprising a VH sequence of SEQ ID NO: 8 and a VL sequence of SEQ ID NO: 7, respectively.

In a further aspect, an anti-Ly6E antibody of an ADC according to any of the above embodiments is a monoclonal antibody, including a human antibody. In one embodiment, an anti-Ly6E antibody of an ADC is an antibody fragment, e.g., a Fv, Fab, Fab', scFv, diabody, or F(ab')₂ fragment. In another embodiment, the antibody is a substantially full length antibody, e.g., an IgG1 antibody, IgG2a antibody or other antibody class or isotype as defined herein. In some embodiments, an ADC comprises an anti-Ly6E antibody comprising a heavy chain and a light chain comprising the amino acid sequences of SEQ ID NO: 16 and 15, respectively.

TABLE 4

Ly6E Antibody Sequences.

| SEQ ID NO | Description | Sequence |
|---|---|---|
| 7 | anti-Ly6E antibody hu9B12 v12 light chain variable region | DIQMTQSPSS LSASVGDRVT ITCSASQGIS NYLNWYQQKP GKTVKLLIYY TSNLHSGVPS RFSGSGSGTD YTLTISSLQP EDFATYYCQQ YSELPWTFGQ GTKVEIK |
| 8 | anti-Ly6E antibody hu9B12 v12 heavy chain variable region | EVQLVESGPA LVKPTQTLTL TCTVSGFSLT GYSVNWIRQPGKAL EWLGMIWGDG STDYNSALKS RLTISKDTSK NQVVLTMTNM DPVDTATYYC ARDYYFNYAS WFAYWGQGTL VTVSS |
| 9 | anti-Ly6E antibody hu9B12 v12 HVR-L1 | SASQGISNYLN |

TABLE 4-continued

Ly6E Antibody Sequences.

| SEQ ID NO | Description | Sequence |
|---|---|---|
| 10 | anti-Ly6E antibody hu9B12 v12 HVR-L2 | YTSNLHS |
| 11 | anti-Ly6E antibody hu9B12 v12 HVR-L3 | QQYSELPWT |
| 12 | anti-Ly6E antibody hu9B12 V12 HVR-H1 | GFSLTGYSVN |
| 13 | anti-Ly6E antibody hu9B12 v12 HVR-H2 | MIWGDGSTDY NSALKS |
| 14 | anti-Ly6E antibody hu9B12 v12 HVR-H3 | DYYVNYASWEAY |
| 15 | anti-Ly6E antibody hu9B12 v12 K149C kappa light chain | DIQMTQSPSS LSASVGDRVT ITCSASQGIS NYLNWYQQKP GKTVKLLIYY TSNLHSGVPS RFSGSGSGTD YTLTISSLQP EDFATYYCQQ YSELPWTFGQ GTKVEIK RTVAAPSVFIF PPSDEQLKSG TASVVCLLNN FYPREAKVQW CVDNALQSGN SQESVTEQDS KDSTYSLSST LTLSKADYEK HKVYACEVTH QGLSSPVTKS FNRGEC |
| 16 | anti-Ly6E antibody hu9B12 v12 IgG1 heavy chain | EVQLVESGPA LVKPTQTLTL TCTVSGFSLT GYSVNWIRQP PGKALEWLGM IWGDGSTDYN SALKSRLTIS KDTSKNQVVL TMTNMDPVDT ATYYCARDYY FNYASWFAYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |

Anti-HER2 Antibodies

In certain embodiments, ADCs comprise anti-HER2 antibodies. In one embodiment, an anti-HER2 antibody of an ADC comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337, which is specifically incorporated by reference herein. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN®. In another embodiment, an anti-HER2 antibody of an ADC comprises a humanized anti-HER2 antibody, e.g., humanized 2C4, as described in U.S. Pat. No. 7,862,817. An exemplary humanized 2C4 antibody is pertuzumab, commercially available under the tradename PERJETA®.

In another embodiment, an anti-HER2 antibody of an ADC comprises a humanized 7C2 anti-HER2 antibody. A humanized 7C2 antibody is an anti-HER2 antibody.

In some embodiments, described herein are ADCs comprising an anti-HER2 antibody comprising at least one, two, three, four, five, or six HVRs selected from (a) HVR-H1 comprising the amino acid sequence of SEQ ID NO: 22; (b) HVR-H2 comprising the amino acid sequence of SEQ ID NO: 23, 27, or 28; (c) HVR-H3 comprising the amino acid sequence of SEQ ID NO: 24 or 29; (d) HVR-L1 comprising the amino acid sequence of SEQ ID NO: 19: (e) HVR-L2 comprising the amino acid sequence of SEQ ID NO: 20; and (f) HVR-L3 comprising the amino acid sequence of SEQ ID NO: 21. In some embodiments, described herein are ADCs comprising an anti-HER2 antibody comprising at least one, two, three, four, five, or six HVRs selected from (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In one aspect, described herein are ADCs comprising an antibody that comprises at least one, at least two, or all three VH HVR sequences selected from (a) HVR-H1 comprising the amino acid sequence of SEQ ID NO: 22; (b) HVR-H2 comprising the amino acid sequence of SEQ ID NO: 23, 27, or 28; and (c) HVR-H3 comprising the amino acid sequence of SEQ ID NO: 24 or 29. In one aspect, described herein are ADCs comprising an antibody that comprises at least one, at least two, or all three VH HVR sequences selected from (a) HVR-H1 comprising the amino acid sequence of SEQ ID NO: 22; (b) HVR-H2 comprising the amino acid sequence of SEQ ID NO: 23; and (c) HVR-H3 comprising the amino acid sequence of SEQ ID NO: 24. In a further embodiment, the antibody comprises (a) HVR-H1 comprising the amino acid sequence of SEQ ID NO: 68, (b) HVR-H2 comprising the amino acid sequence of SEQ ID NO: 23, 27, or 28; and (c) HVR-H3 comprising the amino acid sequence of SEQ ID NO: 24 or 29. In a further embodiment, the antibody comprises (a) HVR-H1 comprising the amino acid sequence of SEQ ID NO: 22; (b) HVR-H2 comprising the amino acid sequence of SEQ ID NO: 23; and (c) HVR-H3 comprising the amino acid sequence of SEQ ID NO: 24.

In another aspect, described herein are ADCs comprising an antibody that comprises at least one, at least two, or all three VL HVR sequences selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21. In one embodiment, the antibody comprises (a) HVR-L1 comprising the amino acid sequence of SEQ ID NO: 19: (b) HVR-L2 comprising the amino acid sequence of SEQ ID NO: 20; and (c) HVR-L3 comprising the amino acid sequence of SEQ ID NO: 21.

In another aspect, an ADC comprises an antibody comprising (a) a VH domain comprising at least one, at least two, or all three VH HVR sequences selected from (i) HVR-H1 comprising the amino acid sequence of SEQ ID NO: 22, (ii) HVR-H2 comprising the amino acid sequence of SEQ ID NO: 23, 27, or 28, and (iii) HVR-H3 comprising an amino acid sequence selected from SEQ ID NO: 24 or 29; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21. In another aspect, an ADC comprises an antibody comprising (a) a VH domain comprising at least one, at least two, or all three VH HVR sequences selected from (i) HVR-H1 comprising the amino acid sequence of SEQ ID NO: 22, (ii) HVR-H2 comprising the amino acid sequence of SEQ ID NO: 23, and (iii) HVR-H3 comprising an amino acid sequence selected from SEQ ID NO: 24; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21.

In another aspect, described herein are ADCs comprising an antibody that comprises (a) HVR-H1 comprising the amino acid sequence of SEQ ID NO: 22; (b) HVR-H2 comprising the amino acid sequence of SEQ ID NO: 23, 27, or 28; (c) HVR-H3 comprising the amino acid sequence of SEQ ID NO: 24 or 29; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21. In another aspect, described herein are ADCs comprising an antibody that comprises (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In any of the above embodiments, an anti-HER2 antibody of an ADC is humanized. In one embodiment, an anti-HER2 antibody of an ADC comprises HVRs as in any of the above embodiments, and further comprises a human acceptor framework, e.g. a human immunoglobulin framework or a human consensus framework.

In another aspect, an anti-HER2 antibody of an ADC comprises a heavy chain variable domain (VH) sequence having at least 90%, 91%, 92%, 93%, 94%, 95%, 96%, 97%, 98°/%, 99%, or 100% sequence identity to the amino acid sequence of SEQ ID NO: 18. In certain embodiments, a VH sequence having at least 90%, 91%, 92%, 93%, 94%, 95%, 96%, 97%, 98%, or 99% identity to the amino acid sequence of SEQ ID NO: 18 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 18. In certain embodiments, a total of 1 to 5 amino acids have been substituted, inserted and/or deleted in SEQ ID NO: 18. In certain embodiments, substitutions, insertions, or deletions occur in regions outside the HVRs (i.e., in the FRs). Optionally, the anti-HER2 antibody comprises the VH sequence of SEQ ID NO: 18, including post-translational modifications of that sequence. In a particular embodiment, the VH comprises one, two or three HVRs selected from: (a) HVR-H1 comprising the amino acid sequence of SEQ ID NO: 22, (b) HVR-H2 comprising the amino acid sequence of SEQ ID NO: 23, and (c) HVR-H3 comprising the amino acid sequence of SEQ ID NO: 24.

In another aspect, an anti-HER2 antibody of an ADC is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 17. In certain embodiments, a VL sequence having at least 900/%, 91°%, 92%, 93%, 94%, 95%, 96%, 97%, 98%, or 99% identity to the amino acid sequence of SEQ ID NO: 17 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 17. In certain embodiments, a total of 1 to 5 amino acids have been substituted, inserted and/or deleted in SEQ ID NO: 17. In certain embodiments, the substitutions, insertions, or deletions occur in regions outside the HVRs (i.e., in the FRs). Optionally, the anti-HER2 antibody comprises the VL sequence of SEQ ID NO: 17, including post-translational modifications of that sequence. In a particular embodiment, the VL comprises one, two or three HVRs selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21.

In another aspect, an ADC comprising an anti-HER2 antibody is provided, wherein the antibody comprises a VH as in any of the embodiments provided above, and a VL as in any of the embodiments provided above.

In one embodiment, an ADC comprising an antibody is provided, wherein the antibody comprises the VH and VL sequences in SEQ ID NO: 18 and SEQ ID NO: 17, respectively, including post-translational modifications of those sequences.

In one embodiment, an ADC comprising an antibody is provided, wherein the antibody comprises the humanized 7C2.v2.2.LA (hu7C2) K149C kappa light chain sequence of SEQ ID NO: 30.

In one embodiment, an ADC comprising an antibody is provided, wherein the antibody comprises the Hu7C2 A118C IgG1 heavy chain sequence of SEQ ID NO: 31.

In a further aspect, provided herein are ADCs comprising antibodies that bind to the same epitope as an anti-HER2 antibody provided herein. For example, in certain embodiments, an ADC is provided, comprising an antibody that binds to the same epitope as an anti-HER2 antibody comprising a VH sequence of SEQ ID NO: 18 and a VL sequence of SEQ ID NO: 17, respectively.

In a further aspect, an anti-HER2 antibody of an ADC according to any of the above embodiments is a monoclonal antibody, including a human antibody. In one embodiment, an anti-HER2 antibody of an ADC is an antibody fragment, e.g., a Fv, Fab, Fab', scFv, diabody, or F(ab')₂ fragment. In another embodiment, an ADC comprises an antibody that is a substantially full length antibody, e.g., an IgG1 antibody, IgG2a antibody or other antibody class or isotype as defined herein.

TABLE 5

Humanized 7C2 anti-HER2 antibody sequences.

| SEQ. ID NO. | Description | Sequence |
|---|---|---|
| 17 | Humanized 7C2.v2.2.LA ("hu7C2") light chain variable region | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IK |
| 18 | Hu7C2 heavy chain variable region | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSS |
| 19 | Hu7C2 HVR-L1 | RASQSVSGSRFTYMH |
| 20 | Hu7C2 HVR-L2 | YASILES |
| 21 | Hu7C2 HVR-L3 | QHSWEIPPWT |
| 22 | Hu7C2 HVR-H1 | GYWMN |
| 23 | Hu7C2 HVR-H2 (Hu7C2.v2.1.S53L, S55A HVR-H2) | MIHPLDAEIRANQKFRD |
| 24 | Hu7C2 HVR-H3 | GTYDGGFEY |
| 25 | Humanized 7C2.v2.2.LA. (hu7C2) kappa light chain | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 26 | Hu7C2 IgG1 heavy chain | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APTEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 27 | Hu7C2.v2.1.S53M HVR-H2 | MIHPMDSEIRANQKFRD |

TABLE 5-continued

Humanized 7C2 anti-HER2 antibody sequences.

| SEQ. ID NO. | Description | Sequence |
|---|---|---|
| 28 | Hu7C2.v2.1.S53L HVR-H2 | MIHPLDSEIRANQKFRD |
| 29 | Hu7C2.v2.1.E101K HVR-H3 | GTYDGGFKY |
| 30 | Humanized 7C2.v2.2.LA.(Hu7C2) K149C kappa light chain | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IKRTVAAPSV FIFPPSDEQL KSGTASVVCL LNNFYPREAK VQWCVDNALQ SGNSQESVTE QDSKDSTYSL SSTLTLSKAD YEKHKVYACE VTHQGLSSPV TKSFNRGEC |
| 31 | Hu7C2 A118C IgG1 heavy chain | EVQLVQSGAE VKKPGASVKV SCKASGYSFT GYWMNWVRQA PGQGLEWIGM IHPDAEIRA NQKFRDRVTI TVDTSTSTAY LELSSLRSED TAVYYCARGT YDGGFEYWGQ GTLVTVSSCS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 98 | exemplary human HER2 precursor protein, with signal sequence | MELAALCRWG LLLALLPPGA ASTQVCTGTD MKLRLPASPE THLDMLRHLY QGCQVVQGNL ELTYLPTNAS LSFLQDIQEV QGYVLIAHNQ VRQVPLQRLR IVRGTQLFED NYALAVLDNG DPLNNTTPVT GASPGGLREL QLRSLTEILK GGVLIQRNPQ LCYQDTILWK DIFHKNNQLA LTLIDTNRSR ACHPCSPMCK GSRCWGESSE DCQSLTRTVC AGGCARCKGP LPTDCCHEQC AAGCTGPKHS DCLACLHFNH SGICELHCPA LVTYNTDTFE SMPNPEGRYT FGASCVTACP YNYLSTDVGS CTLVCPLHNQ EVTAEDGTQR CEKCSKPCAR VCYGLGMEHL REVRAVTSAN IQEFAGCKKI FGSLAFLPES FDGDPASNTA PLQPEQLQVF ETLEEITGYL YISAWPDSLP DLSVFQNLQV IRGRILHNGA YSLTLQGLGI SWLGLRSLRE LGSGLALIHH NTHLCFVHTV PWDQLFRNPH QALLHTANRP EDECVGEGLA CHQLCARGHC WGPGPTQCVN CSQFLRGQEC VEECRVLQGL PREYVNARHC LPCHPECQPQ NGSVTCFGPE ADQCVACAHY KDPPFCVARC PSGVKPDLSY MPIWKFPDEE GACQPCPINC THSCVDLDDK GCPAEQRASP LTSIISAVVG ILLVVVLGVV FGILIKRRQQ KIRKYTMRRL LQETELVEPL TPSGAMPNQA QMRILKETEL RKVKVLGSGA FGTVYKGIWI PDGENVKIPV AIKVLRENTS PKANKEILDE AYVMAGVGSP YVSRLLGICL TSTVQLVTQL MPYGCLLDHV RENRGRLGSQ DLLNWCMQIA KGMSYLEDVR LVHRDLAARN VLVKSPNHVK ITDFGLARLL DIDETEYHAD GGKVPIKWMA LESILRRRFT HQSDVWSYGV TVWELMTFGA KPYDGIPARE IPDLLEKGER LPQPPICTID VYMIMVKCWM IDSECRPRFR ELVSEFSRMA RDPQRFVVIQ NEDLGPASPL DSTFYRSLLE DDDMGDLVDA EEYLVTQQGF FCPDPAPGAG GMVHHRHRSS STRSGGGDLT LGLEPSEEEA PRSPLAPSEG AGSDVFDGDL GMGAKKGLQS LPTHDPSPLQ RYSEDPTVPL PSETDGYVAP LTCSPQPEYV NQPDVRPQPP SPREGPLPAA RPAGATLERP KTLSPGKNGV VKDVFAFGGA VENPEYLTPQ GGAAPQPHPP PAFSPAFDNL YYWDQDPPER GAPPSTFKGT PTAENPEYLG LDVPV |

Anti-MUC16 Antibodies

In certain embodiments, ADCs comprise anti-MUC16 antibodies.

In some embodiments, described herein are ADCs comprising an anti-MUC16 antibody comprising at least one, two, three, four, five, or six HVRs selected from (a) HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37; (d) HVR-L1 comprising the amino acid sequence of SEQ ID NO: 32; (e) HVR-L2 comprising the amino acid sequence of SEQ ID NO: 33 and (f) HVR-L3 comprising the amino acid sequence of SEQ ID NO: 34.

In one aspect, described herein are ADCs comprising an antibody that comprises at least one, at least two, or all three VH HVR sequences selected from (a) HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37. In a further embodiment, the antibody comprises (a)

HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37.

In another aspect, described herein are ADCs comprising an antibody that comprises at least one, at least two, or all three VL HVR sequences selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34. In one embodiment, the antibody comprises (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, an ADC comprises an antibody comprising (a) a VH domain comprising at least one, at least two, or all three VH HVR sequences selected from (i) HVR-H1 comprising the amino acid sequence of SEQ ID NO: 35, (ii) HVR-H2 comprising the amino acid sequence of SEQ ID NO: 36, and (iii) HVR-H3 comprising an amino acid sequence selected from SEQ ID NO: 37; and (b) a VL domain comprising at least one, at least two, or all three VL HVR sequences selected from (i) HVR-L1 comprising the amino acid sequence of SEQ ID NO: 32, (ii) HVR-L2 comprising the amino acid sequence of SEQ ID NO: 33, and (c) HVR-L3 comprising the amino acid sequence of SEQ ID NO: 34.

In another aspect, described herein are ADCs comprising an antibody that comprises (a) HVR-H1 comprising the amino acid sequence of SEQ ID NO: 35 (b) HVR-H2 comprising the amino acid sequence of SEQ ID NO: 36; (c) HVR-H3 comprising the amino acid sequence of SEQ ID NO: 37; (d) HVR-L1 comprising the amino acid sequence of SEQ ID NO: 32; (e) HVR-L2 comprising the amino acid sequence of SEQ ID NO: 33; and (f) HVR-L3 comprising the amino acid sequence of SEQ ID NO: 34.

In any of the above embodiments, an anti-MUC16 antibody of an ADC is humanized. In one embodiment, an anti-MUC16 antibody comprises HVRs as in any of the above embodiments, and further comprises a human acceptor framework, e.g. a human immunoglobulin framework or a human consensus framework.

In another aspect, an anti-MUC16 antibody of an ADC comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 39. In certain embodiments, a VH sequence having at least 90%, 91%, 92%, 93%, 94%, 95%, 96%, 97%, 98%, or 99% identity to the amino acid sequence of SEQ ID NO: 39 contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 39. In certain embodiments, a total of 1 to 5 amino acids have been substituted, inserted and/or deleted in SEQ ID NO: 39. In certain embodiments, substitutions, insertions, or deletions occur in regions outside the HVRs (i.e., in the FRs). Optionally, the anti-MUC16 antibody comprises the VH sequence of SEQ ID NO: 39, including post-translational modifications of that sequence. In a particular embodiment, the VH comprises one, two or three HVRs selected from: (a) HVR-H1 comprising the amino acid sequence of SEQ ID NO: 35, (b) HVR-H2 comprising the amino acid sequence of SEQ ID NO: 36, and (c) HVR-H3 comprising the amino acid sequence of SEQ ID NO: 37.

In another aspect, an anti-MUC16 antibody of an ADC is provided, wherein the antibody comprises a light chain variable domain (VL) having at least 90%, 91%, 920/%, 93%, 94%, 95%, 96%, 97%, 98%, 99%, or 100% sequence identity to the amino acid sequence of SEQ ID NO: 38. In certain embodiments, a VL sequence having at least 90%, 91%, 92%, 93%, 94%, 95%, 96%, 97%, 98%, or 99% identity to the amino acid sequence of SEQ ID NO:38 contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 38. In certain embodiments, a total of 1 to 5 amino acids have been substituted, inserted and/or deleted in SEQ ID NO: 38. In certain embodiments, the substitutions, insertions, or deletions occur in regions outside the HVRs (i.e., in the FRs). Optionally, the anti-MUC16 antibody comprises the VL sequence of SEQ ID NO: 38, including post-translational modifications of that sequence. In a particular embodiment, the VL comprises one, two or three HVRs selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, an ADC comprising an anti-MUC16 antibody is provided, wherein the antibody comprises a VH as in any of the embodiments provided above, and a VL as in any of the embodiments provided above.

In one embodiment, an ADC is provided, wherein the antibody comprises the VH and VL sequences in SEQ ID NO: 39 and SEQ ID NO: 38, respectively, including post-translational modifications of those sequences.

In a further aspect, provided herein are ADCs comprising antibodies that bind to the same epitope as an anti-MUC16 antibody provided herein. For example, in certain embodiments, an ADC is provided comprising an antibody that binds to the same epitope as an anti-MUC16 antibody comprising a VH sequence of SEQ ID NO: 39 and a VL sequence of SEQ ID NO: 38, respectively.

In a further aspect, an anti-MUC16 antibody of an ADC according to any of the above embodiments is a monoclonal antibody, including a human antibody. In one embodiment, an anti-MUC16 antibody of an ADC is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

TABLE 6

MUC16 Antibody Sequences.

| SEQ ID NO: | Description | Sequence |
|---|---|---|
| 32 | Anti-Muc16 antibody HVR-L1 | KASDLIHNWL A |
| 33 | Anti-Muc16 antibody HVR-L2 | YGATSLET |
| 34 | Anti-Muc16 antibody HVR-L3 | QQYWTTPFT |
| 35 | Anti-Muc16 antibody HVR-H1 | GYSITNDYAW N |
| 36 | Anti-Muc16 antibody HVR-H2 | GYISYSGYTT YNPSLKS |
| 37 | Anti-Muc16 antibody HVR-H3 | ARWASGLDY |
| 38 | Anti-Muc16 antibody light chain variable region | DIQMTQSPSS LSASVGDRVT ITCKASDLIH NWLAWYQQKP GKAPKLLIYG ATSLETGVPS RFSGSGSGTD FTLTISSLQP EDFATYYCQQ YWTTPFTFGQ GTKVEIKR |
| 39 | Anti-Muc16 antibody heavy chain variable region | EVQLVESGGG LVQPGGSLRL SCAASGYSIT NDYAWNWVRQ ARGKGLEWVG YISYSGYTTY NPSLKSRFTI SRDTSKNTLY LQMNSLRAED TAVYYCARWA SGLDYWGQGT LVTVSS |

Anti-STEAP-1 Antibodies

In certain embodiments, ADCs comprise anti-STEAP-1 antibodies.

In some embodiments, described herein are ADCs comprising an anti-STEAP-1 antibody comprising at least one, two, three, four, five, or six HVRs selected from (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42; (d) HVR-L1 comprising the amino acid sequence of SEQ ID NO: 43; (e) HVR-L2 comprising the amino acid sequence of SEQ ID NO: 44 and (f) HVR-L3 comprising the amino acid sequence of SEQ ID NO: 45.

In one aspect, described herein are ADCs comprising an antibody that comprises at least one, at least two, or all three VH HVR sequences selected from (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42. In a further embodiment, the antibody comprises (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42.

In another aspect, described herein are ADCs comprising an antibody that comprises at least one, at least two, or all three VL HVR sequences selected from (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45. In one embodiment, the antibody comprises (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45.

In another aspect, an ADC comprises an antibody comprising (a) a VH domain comprising at least one, at least two, or all three VH HVR sequences selected from (i) HVR-H1 comprising the amino acid sequence of SEQ ID NO: 40, (ii) HVR-H2 comprising the amino acid sequence of SEQ ID NO: 41, and (iii) HVR-H3 comprising an amino acid sequence selected from SEQ ID NO: 42; and (b) a VL domain comprising at least one, at least two, or all three VL HVR sequences selected from (i) HVR-L1 comprising the amino acid sequence of SEQ ID NO: 43, (ii) HVR-L2 comprising the amino acid sequence of SEQ ID NO: 44, and (c) HVR-L3 comprising the amino acid sequence of SEQ ID NO: 45.

In another aspect, described herein are ADCs comprising an antibody that comprises (a) HVR-H1 comprising the amino acid sequence of SEQ ID NO: 40 (b) HVR-H2 comprising the amino acid sequence of SEQ ID NO: 41; (c) HVR-H3 comprising the amino acid sequence of SEQ ID NO: 42; (d) HVR-L1 comprising the amino acid sequence of SEQ ID NO: 43; (e) HVR-L2 comprising the amino acid sequence of SEQ ID NO: 44; and (f) HVR-L3 comprising the amino acid sequence of SEQ ID NO: 45.

In any of the above embodiments, an anti-STEAP-1 antibody of an ADC is humanized. In one embodiment, an anti-STEAP-1 antibody comprises HVRs as in any of the above embodiments, and further comprises a human acceptor framework, e.g. a human immunoglobulin framework or a human consensus framework.

In another aspect, an anti-STEAP-1 antibody of an ADC comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 46. In certain embodiments, a VH sequence having at least 90%, 91%, 92%, 93%, 94%, 95%, 96%, 97%, 98%, or 99% identity to the amino acid sequence of SEQ ID NO: 46 contains substitutions (e.g., conservative substitutions), insertions, or deletions relative to the reference sequence, but an anti-STEAP-1 antibody comprising that sequence retains the ability to bind to STEAP-1. In certain embodiments, a total of 1 to 10 amino acids have been substituted, inserted and/or deleted in SEQ ID NO: 46. In certain embodiments, a total of 1 to 5 amino acids have been substituted, inserted and/or deleted in SEQ ID NO: 46. In certain embodiments, substitutions, insertions, or deletions occur in regions outside the HVRs (i.e., in the FRs). Optionally, the anti-STEAP-1 antibody comprises the VH sequence of SEQ ID NO: 46, including post-translational modifications of that sequence. In a particular embodiment, the VH comprises one, two or three HVRs selected from: (a) HVR-H1 comprising the amino acid sequence of SEQ ID NO: 40, (b) HVR-H2 comprising the amino acid sequence of SEQ ID NO: 41, and (c) HVR-H3 comprising the amino acid sequence of SEQ ID NO: 42.

In another aspect, an anti-STEAP-1 antibody of an ADC is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 47. In certain embodiments, a VL sequence having at least 90%, 91%, 92%, 93%, 94%, 95%, 96%, 97%, 98%, or 99% identity to the amino acid sequence of SEQ ID NO: 47 contains substitutions (e.g., conservative substitutions), insertions, or deletions relative to the reference sequence, but an anti-STEAP-1 antibody comprising that sequence retains the ability to bind to STEAP-1. In certain embodiments, a total of 1 to 10 amino acids have been substituted, inserted and/or deleted in SEQ ID NO: 47 In certain embodiments, a total of 1 to 5 amino acids have been substituted, inserted and/or deleted in SEQ ID NO: 47. In certain embodiments, the substitutions, insertions, or deletions occur in regions outside the HVRs (i.e., in the FRs). Optionally, the anti-STEAP-1 antibody comprises the VL sequence of SEQ ID NO: 47, including post-translational modifications of that sequence. In a particular embodiment, the VL comprises one, two or three HVRs selected from (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45.

In another aspect, an ADC comprising an anti-STEAP-1 antibody is provided, wherein the antibody comprises a VH as in any of the embodiments provided above, and a VL as in any of the embodiments provided above.

In one embodiment, an ADC is provided, wherein the antibody comprises the VH and VL sequences in SEQ ID NO: 46 and SEQ ID NO: 47, respectively, including post-translational modifications of those sequences.

In a further aspect, provided herein are ADCs comprising antibodies that bind to the same epitope as an anti-STEAP-1 antibody provided herein. For example, in certain embodiments, an ADC is provided comprising an antibody that binds to the same epitope as an anti-STEAP-1 antibody comprising a VH sequence of SEQ ID NO: 46 and a VL sequence of SEQ ID NO: 47, respectively.

In a further aspect, an anti-STEAP-1 antibody of an ADC according to any of the above embodiments is a monoclonal antibody, including a human antibody. In one embodiment, an anti-STEAP-1 antibody of an ADC is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

TABLE 7

STEAP Antibody Sequences.

| SEQ ID NO: | Description | Sequence |
|---|---|---|
| 40 | Anti-STEAP-1 HVR-H1 | GYSITSDYAW N |
| 41 | Anti-STEAP-1 HVR-H2 | GYISNSGSTS YNPSLKS |
| 42 | Anti-STEAP-1 HVR-H3 | ERNYDYDDYY YAMDY |
| 43 | Anti-STEAP-1 HVR-L1 | KSSQSLLYRS NQKNYLA |
| 44 | Anti-STEAP-1 HVR-L2 | WASTRES |
| 45 | Anti-STEAP1 HVR-L3 | QQYYNYPRT |
| 46 | Anti-STEAP1 heavy chain variable region | EVQLVESGGG LVQPGGSLRL SCAVSGYSIT SDYAWNWVRQ APGKGLEWVG YISNSGSTSY NPSLKSRFTI SRDTSKNTLY LQMNSLRAED TAVYYCARER NYDYDDYYA MDYWGQGTLV TVSS |
| 47 | Anti-STEAP1 light chain variable region | DIQMTQSPSS LSASVGDRVT ITCKSSQSLL YRSNQKNYLA WYQQKPGKAP LKKIYWASTR ESGVPSRFSG SGSGTDFTLT ISSLQPEDFA TYYCQQYYNY PRTFGQGTKV EIK |

Anti-NaPi2b Antibodies

In certain embodiments, an ADC comprises anti-NaPi2b antibodies.

In some embodiments, described herein are ADCs comprising an anti-NaPi2b antibody comprising at least one, two, three, four, five, or six HVRs selected from (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 51; (e) HVR-L2 comprising the amino acid sequence of SEQ ID NO: 52 and (f) HVR-L3 comprising the amino acid sequence of SEQ ID NO: 53.

In one aspect, described herein are ADCs comprising an antibody that comprises at least one, at least two, or all three VH HVR sequences selected from (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50. In a further embodiment, the antibody comprises (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50.

In another aspect, described herein are ADCs comprising an antibody that comprises at least one, at least two, or all three VL HVR sequences selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53. In one embodiment, the antibody comprises (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53.

In another aspect, an ADC comprises an antibody comprising (a) a VH domain comprising at least one, at least two, or all three VH HVR sequences selected from (i) HVR-H1 comprising the amino acid sequence of SEQ ID NO: 48, (ii) HVR-H2 comprising the amino acid sequence of SEQ ID NO: 49, and (iii) HVR-H3 comprising an amino acid sequence selected from SEQ ID NO: 50; and (b) a VL domain comprising at least one, at least two, or all three VL HVR sequences selected from (i) HVR-L1 comprising the amino acid sequence of SEQ ID NO: 51, (ii) HVR-L2 comprising the amino acid sequence of SEQ ID NO: 52, and (c) HVR-L3 comprising the amino acid sequence of SEQ ID NO: 53.

In another aspect, described herein are ADCs comprising an antibody that comprises (a) HVR-H1 comprising the amino acid sequence of SEQ ID NO: 48 (b) HVR-H2 comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 51; (e) HVR-L2 comprising the amino acid sequence of SEQ ID NO: 52; and (f) HVR-L3 comprising the amino acid sequence of SEQ ID NO: 53.

In any of the above embodiments, an anti-NaPi2b antibody of an ADC is humanized. In one embodiment, an anti-NaPi2b antibody comprises HVRs as in any of the above embodiments, and further comprises a human acceptor framework, e.g. a human immunoglobulin framework or a human consensus framework.

In another aspect, an anti-NaPi2b antibody of an ADC comprises a heavy chain variable domain (VH) sequence having at least 90%, 91%, 92%, 93%, 94%, 95%, 96%, 97%, 98%, 990%, or 100% sequence identity to the amino acid sequence of SEQ ID NO: 54. In certain embodiments, a VH sequence having at least 90%, 91%, 92%, 93%, 94%, 95%, 96%, 97%, 98%, or 99% identity to the amino acid sequence of SEQ ID NO: 54 contains substitutions (e.g., conservative substitutions), insertions, or deletions relative to the reference sequence, but an anti-NaPi2b antibody comprising that sequence retains the ability to bind to NaPi2b. In certain embodiments, a total of 1 to 10 amino acids have been substituted, inserted and/or deleted in SEQ ID NO: 54. In certain embodiments, a total of 1 to 5 amino acids have been substituted, inserted and/or deleted in SEQ ID NO: 54. In certain embodiments, substitutions, insertions, or deletions occur in regions outside the HVRs (i.e., in the FRs). Optionally, the anti-NaPi2b antibody comprises the VH sequence of SEQ ID NO: 54, including post-translational modifications of that sequence. In a particular embodiment, the VH comprises one, two or three HVRs selected from: (a) HVR-H1 comprising the amino acid sequence of SEQ ID NO: 48, (b) HVR-H2 comprising the amino acid sequence of SEQ ID NO: 49, and (c) HVR-H3 comprising the amino acid sequence of SEQ ID NO: 50.

In another aspect, an anti-NaPi2b antibody of an ADC is provided, wherein the antibody comprises a light chain variable domain (VL) having at least 90%, 91%, 92%, 930%, 94%, 95%, 96%, 97%, 98%, 99%, or 100% sequence identity to the amino acid sequence of SEQ ID NO: 55. In certain embodiments, a VL sequence having at least 90%, 91%, 92%, 93%, 94%, 95%, 96%, 97%, 98%, or 99% identity to the amino acid sequence of SEQ ID NO: 55 contains substitutions (e.g., conservative substitutions), insertions, or deletions relative to the reference sequence, but an anti-NaPi2b antibody comprising that sequence retains the ability to bind to anti-NaPi2b. In certain embodiments, a total of 1 to 10 amino acids have been substituted, inserted and/or deleted in SEQ ID NO: 55. In certain embodiments, a total of 1 to 5 amino acids have been substituted, inserted and/or deleted in SEQ ID NO: 55. In certain embodiments, the substitutions, insertions, or deletions occur in regions outside the HVRs (i.e., in the FRs). Optionally, the anti-NaPi2b antibody comprises the VL sequence of SEQ ID NO: 55, including post-translational modifications of that sequence. In a particular embodiment, the VL comprises one, two or three HVRs selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53.

In another aspect, an ADC comprising an anti-NaPi2b antibody is provided, wherein the antibody comprises a VH as in any of the embodiments provided above, and a VL as in any of the embodiments provided above.

In one embodiment, an ADC is provided, wherein the antibody comprises the VH and VL sequences in SEQ ID NO: 54 and SEQ ID NO: 55, respectively, including post-translational modifications of those sequences.

In a further aspect, provided herein are ADCs comprising antibodies that bind to the same epitope as an anti-NaPi2b antibody provided herein. For example, in certain embodiments, an ADC is provided comprising an antibody that binds to the same epitope as an anti-NaPi2b antibody comprising a VH sequence of SEQ ID NO: 54 and a VL sequence of SEQ ID NO: 55, respectively.

In a further aspect, an anti-NaPi2b antibody of an ADC according to any of the above embodiments is a monoclonal antibody, including a human antibody. In one embodiment, an anti-NaPi2b antibody of an ADC is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

TABLE 8

NaPi2B Antibody Sequences.

| SEQ ID NO: | Description | Sequence |
|---|---|---|
| 48 | Anti-NaPi2b HVR-H1 10H1.11.4B | GFSGSDFAMS |
| 49 | Anti-NaPi2b HVR-H2 10H1.11.4B | ATIGRVAFHTYYPDSMKG |
| 50 | Anti-NaPi2b HVR-H3 10H1.11.4B | ARHRGFDVGHFDF |
| 51 | Anti-NaPi2b HVR-L1 10H1.11.4B | RSSETLVHSSGNTYLE |
| 52 | Anti-NaPi2b HVR-L2 | RVSNRFS |
| 53 | Anti-NaPi2b HVR-L3 10H1.11.4B | FQGSFNPLT |
| 54 | Anti-NaPi2b heavy chain variable region 10H1.11.4B $V_H$ | EVQLVESGGGLVQPGGSLRLSCAASGFSFSDFAMSWVRQ APGKGLEWVATIGRVAFHTYYPDSMKGRFTISRDNSKNT LYLQMNSLRAEDTAVYYCARHRGFDVGHFDFWGQGTLVT VSS |
| 55 | Anti-NaPi2b light chain variable region 10H1.11.4B $V_L$ | DIQMTQSPSSLSASVGDRVTITCRSSETLVHSSGNTYLE WYQQKPGKAPKLLIYRVSNRFSGVPSRFSGSGSGTDFTL TISSLQPEDFATYYCFQGSFNPLTFGQGTKVEIKR |
| 64 | 10H1.114B Light Chain | DIQMTQSPSSLSASVGDRVTITCRSSETLVHSSGNTYLE WYQQKPGKAPKLLIYRVSNRFSGVPSRFSGSGSGTDFTL TISSLQPEDFATYYCFQGSFNPLTFGQGTKVEIKRTVAA PSVFIFPPSDEQLKSGTASVVCLLNNFYPREAKVQWKVD NALQSGNSQESVTEQDSKDSTYSLSSTLTLSKADYEKHK VYACEVTHQGLSSPVTKSFNRGEC |
| 65 | 10H1.114B Heavy Chain | EVQLVESGGGLVQPGGSLRLSCAASGFSFSDFAMSWVRQ APGKGLEWVATIGRVAFHTYYPDSMKGRFTISRDNSKNT LYLQMNSLRAEDTAVYYCARHRGFDVGHFDFWGQGTLVT VSSCSTKGPSVFPLAPSSKSTSGGTAALGCLVKDYFPEP VTVSWNSGALTSGVHTFPAVLQSSGLYSLSSVVTVPSSS LGTQTYICNVNHKPSKTKVDKKVEPKSCDKTHTCPPCPA PELLGGPSVFLFPPKPKDTLMISRTPEVTCVVVDVSHED PEVKFNWYVDGVEVHNAKTKPREEQYNSTYRVVSVLTVL HQDWLNGKEYKCKVSNKALPAPIEKTISKAKGQPREPQV YTLPFSREEMTKNQVSLTCLVKGFYPSDIAVEWESNGQP ENNYKTTPPVLDSDGSFFLYSKLTVDKSRWQQGNVFSCS VMHEALHNHYTQKSLSLSPGK |

Anti-CD79b Antibodies

In certain embodiments, ADCs comprise anti-CD79b antibodies.

In some embodiments, described herein are ADCs comprising an anti-CD79b antibody comprising at least one, two, three, four, five, or six HVRs selected from (a) HVR-H1 comprising the amino acid sequence of SEQ ID NO: 58; (b) HVR-H2 comprising the amino acid sequence of SEQ ID NO: 59; (c) HVR-H3 comprising the amino acid sequence of SEQ ID NO: 60; (d) HVR-L1 comprising the amino acid sequence of SEQ ID NO: 61; (e) HVR-L2 comprising the amino acid sequence of SEQ ID NO: 62; and (f) HVR-L3 comprising the amino acid sequence of SEQ ID NO: 63.

In one aspect, described herein are ADCs comprising an antibody that comprises at least one, at least two, or all three VH HVR sequences selected from (a) HVR-H1 comprising the amino acid sequence of SEQ ID NO: 58; (b) HVR-H2 comprising the amino acid sequence of SEQ ID NO: 59; and (c) HVR-H3 comprising the amino acid sequence of SEQ ID NO: 60. In a further embodiment, the antibody comprises (a) HVR-H1 comprising the amino acid sequence of SEQ ID NO: 58; (b) HVR-H2 comprising the amino acid sequence of SEQ ID NO: 59, and (c) HVR-H3 comprising the amino acid sequence of SEQ ID NO: 60.

In another aspect, described herein are ADCs comprising an antibody that comprises at least one, at least two, or all three VL HVR sequences selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63. In one embodiment, the antibody comprises (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, an ADC comprises an antibody comprising (a) a VH domain comprising at least one, at least two, or all three VH HVR sequences selected from (i) HVR-H1 comprising the amino acid sequence of SEQ ID NO: 58, (ii) HVR-H2 comprising the amino acid sequence of SEQ ID NO: 59, and (iii) HVR-H3 comprising an amino acid sequence selected from SEQ ID NO: 60; and (b) a VL domain comprising at least one, at least two, or all three VL HVR sequences selected from (i) HVR-L1 comprising the amino acid sequence of SEQ ID NO: 61, (ii) HVR-L2 comprising the amino acid sequence of SEQ ID NO: 62, and (c) HVR-L3 comprising the amino acid sequence of SEQ ID NO: 63.

In another aspect, described herein are ADCs comprising an antibody that comprises (a) HVR-H1 comprising the amino acid sequence of SEQ ID NO: 58; (b) HVR-H2 comprising the amino acid sequence of SEQ ID NO: 59; (c) HVR-H3 comprising the amino acid sequence of SEQ ID NO: 60; (d) HVR-L1 comprising the amino acid sequence of SEQ ID NO: 61; (e) HVR-L2 comprising the amino acid sequence of SEQ ID NO: 62; and (f) HVR-L3 comprising the amino acid sequence of SEQ ID NO: 63.

In any of the above embodiments, an anti-CD79b antibody of an ADC is humanized. In one embodiment, an anti-CD79b antibody comprises HVRs as in any of the above embodiments, and further comprises a human acceptor framework, e.g. a human immunoglobulin framework or a human consensus framework.

In another aspect, an anti-CD79b antibody of an ADC comprises a heavy chain variable domain (VH) sequence having at least 90%, 91%, 92%, 93%, 94%, 95%, 96%, 97%, 98%, 990%, or 100% sequence identity to the amino acid sequence of SEQ ID NO: 56. In certain embodiments, a VH sequence having at least 90%, 91%, 92%, 93%, 94%, 95%, 96%, 97%, 98%, or 99% identity to the amino acid sequence of SEQ ID NO: 56 contains substitutions (e.g., conservative substitutions), insertions, or deletions relative to the reference sequence, but an anti-CD79b antibody comprising that sequence retains the ability to bind to CD79b. In certain embodiments, a total of 1 to 10 amino acids have been substituted, inserted and/or deleted in SEQ ID NO: 56. In certain embodiments, a total of 1 to 5 amino acids have been substituted, inserted and/or deleted in SEQ ID NO: 56. In certain embodiments, substitutions, insertions, or deletions occur in regions outside the HVRs (i.e., in the FRs). Optionally, the anti-CD79b antibody comprises the VH sequence of SEQ ID NO: 8, including post-translational modifications of that sequence. In a particular embodiment, the VH comprises one, two or three HVRs selected from: (a) HVR-H1 comprising the amino acid sequence of SEQ ID NO: 58, (b) HVR-H2 comprising the amino acid sequence of SEQ ID NO: 59, and (c) HVR-H3 comprising the amino acid sequence of SEQ ID NO: 60.

In another aspect, an anti-CD79b antibody of an ADC is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 57. In certain embodiments, a VL sequence having at least 90%, 91%, 92%, 93%, 94%, 95%, 96%, 97%, 98%, or 99% identity to the amino acid sequence of SEQ ID NO: 57 contains substitutions (e.g., conservative substitutions), insertions, or deletions relative to the reference sequence, but an anti-Ly6E antibody comprising that sequence retains the ability to bind to CD79b. In certain embodiments, a total of 1 to 10 amino acids have been substituted, inserted and/or deleted in SEQ ID NO: 57. In certain embodiments, a total of 1 to 5 amino acids have been substituted, inserted and/or deleted in SEQ ID NO: 57. In certain embodiments, the substitutions, insertions, or deletions occur in regions outside the HVRs (i.e., in the FRs). Optionally, the anti-CD79b antibody comprises the VL sequence of SEQ ID NO: 57, including post-translational modifications of that sequence. In a particular embodiment, the VL comprises one, two or three HVRs selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, described herein are ADCs comprising an anti-CD79b antibody is provided, wherein the antibody comprises a VH as in any of the embodiments provided above, and a VL as in any of the embodiments provided above.

In one embodiment, an ADC is provided, wherein the antibody comprises the VH and VL sequences in SEQ ID NO: 56 and SEQ ID NO: 57, respectively, including post-translational modifications of those sequences.

In a further aspect, provided herein are ADCs comprising antibodies that bind to the same epitope as an anti-CD79b antibody provided herein. For example, in certain embodiments, an ADC is provided comprising an antibody that binds to the same epitope as an anti-CD79b antibody comprising a VH sequence of SEQ ID NO: 56 and a VL sequence of SEQ ID NO: 57, respectively.

In a further aspect, an anti-CD79b antibody of an ADC according to any of the above embodiments is a monoclonal antibody, including a human antibody. In one embodiment, an anti-CD79b antibody of an ADC is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

TABLE 9

CD79b Antibody Sequences.

| SEQ ID NO: | Description | Sequence | | |
|---|---|---|---|---|
| 56 | anti-CD79b huMA79bv28 heavy chain variable region | EVQLVESGGG SYWIEWVRQA NEIFKGRATF TAVYYCTRRV | LVQPGGSLRL PGKGLEWIGE SADTSKNTAY PIRLDYWGQG | SCAASGYTFS ILPGGGDTNY LQMNSLRAED TLVTVSS |

TABLE 9-continued

CD79b Antibody Sequences.

| SEQ ID NO: | Description | Sequence |
|---|---|---|
| 57 | anti-CD79b huMA79bv28 light chain variable region | DIQLTQSPSS LSASVGDRVT ITCKASQSVD YEGDSFLNWY QQKPGKAPKL LIYAASNLES GVPSRFSGSG SGTDFTLTIS SLQPEDFATY YCQQSNEDPL TFGQGTKVEI KR |
| 58 | anti-CD79b huMA79bv28 HVR H1 | GYTFSSYWIE |
| 59 | anti-CD79b huMA79bv28 HVR H2 | GEILPGGGDTNYNEIFKG |
| 60 | anti-CD79b huMA79bv28 HVR H3 | TRRVPIRLDY |
| 61 | anti-CD79b huMA79bv28 HVR L1 | KASQSVDYEGDSFLN |
| 62 | anti-CD79b huMA79bv28 HVR L2 | AASNLES |
| 63 | anti-CD79b huMA79bv28 HVR L3 | QQSNEDPLT |

Anti-CD22 Antibodies

In certain embodiments, an ADC can comprise anti-CD22 antibodies, which comprise three light chain hypervariable regions (HVR-L1, HVR-L2 and HVR-L3) and three heavy chain hypervariable regions (HVR-H1, HVR-H2 and HVR-H3). In one embodiment, the anti-CD22 antibody of an ADC comprises three light chain hypervariable regions and three heavy chain hypervariable regions (SEQ ID NO: 66-71), the sequences of which are shown below. In one embodiment, the anti-CD22 antibody of an ADC comprises the variable light chain sequence of SEQ ID NO: 72 and the variable heavy chain sequence of SEQ ID NO: 73. In one embodiment, the anti-CD22 antibody of ADCs of the present subject matter described herein comprises the light chain sequence of SEQ ID NO: 74 and the heavy chain sequence of SEQ ID NO: 75:

TABLE 10

Anti-CD22 Antibodies,

| h10F4.V3.K149C HVR-L1 | RSSQSIVHSVGNTFLE | Seq ID No: 66 |
|---|---|---|
| h10F4.V3.K149C HVR-L2 | KVSNRFS | Seq ID No: 67 |
| h10F4.V3.K149C HVR-L3 | FQGSQFPYT | Seq ID No: 68 |
| h10F4.V3.K149C HVR-H1 | GYEFSRSWMN | Seq ID No: 69 |
| h10F4.V3.K149C HVR-H2 | RIYPGDGDTNYSGKFKG | Seq ID No: 70 |
| h10F4.V3.K149C HVR-H3 | DGSSWDWYFDV | Seq ID No: 71 |
| h10F4.V3.K149C $V_L$ | DIQMTQSPSSLSASVGDRVTITCRSSQSIVHSVG NTFLEWYQQKPGKAPKLLIYKVSNRFSGVPSRFS GSGSGTDFTLTISSLQPEDFATYYCFQGSQFPYT FGQGTKVEIKR | Seq ID No: 72 |
| h10F4.V3.K149C $V_H$ | EVQLVESGGGLVQPGGSLRLSCAASGYEFSRSWM NWVRQAPGKGLEWVGRIYPGDGDTNYSGKFKGRF TISADTSKKTAYLQMNSLRAEDTAVYYCARDGSS WDWYFDVWGQGTLVTVSS | Seq ID No: 73 |

TABLE 10-continued

Anti-CD22 Antibodies,

| | | |
|---|---|---|
| h10F4.V3.K149C Light Chain | DIQMTQSPSSLSASVGDRVTITCRSSQSIVHSVG NTFLEWYQQKP GKAPKLLIYKVSNRFSGVPSRFSGSGSGTDFTLT ISSLQPEDFATYYCFQGSQFPYTFGQGTKVEIKR TVAAPSVFIFPPSDEQLKSGTASVVCLLNNFYPR EAKVQWCVDNALQSGNSQESVTEQDSKDSTYSLS STLTLSKADYEKHKVYACEVTHQGLSSPVTKSFN RGEC | Seq ID No: 74 |
| h10F4.V3.K149C Heavy Chain | EVQLVESGGGLVQPGGSLRLSCAASGYEFSRSWM NWVRQAPGKGLEWVGRIYPGDGDTNYSGKFKGRF TISADTSKNTAYLQMNSLRAEDTAVYYCARDGSS WDWYFDVWGQGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPELL GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFF LYSKLTVDKSRW QQGNVFSCSVMHEALHNHYTQKSLSLSPGK | Seq ID No: 75 |

Anti-CD33 Antibodies

In certain embodiments, an ADC can comprise anti-CD33 antibodies, which comprise three light chain hypervariable regions and three heavy chain hypervariable regions, the sequences (SEQ ID NO:76-81) of which are shown below. In one embodiment, the anti-CD33 antibody of an ADC comprises the variable light chain sequence of SEQ ID NO: 82 and the variable heavy chain sequence of SEQ ID NO: 83.

TABLE 11

| | | |
|---|---|---|
| 15G15.33-HVR L1 | RSSQSLLHSNGYNYLD | SEQ ID NO: 76 |
| 15G15.33-HVR L2 | LGVNSVS | SEQ ID NO: 77 |
| 15G15.33-HVR L3 | MQALQTPWT | SEQ ID NO: 78 |
| 15G15.33-HVR H1 | NHAIS | SEQ ID NO: 79 |
| 15G-15.33-HVR H2 | GIIPIFGTANYAQKFQG | SEQ ID NO: 80 |
| 15G15.33-HVR H3 | EWADVFDI | SEQ ID NO: 81 |
| 15G15.33 V$_L$ | EIVLTQSPLSLPVTPGEPASISCRSSQSLLHSNGYNYLDW YLQKPGQSPQLLIYLGVNSVSGVPDRFSGSGSGTDFTLKI SRVEAEDVGVYYCMQALQTPWTFGQGTKVEIK | SEQ ID NO: 82 |
| 15G15.33 V$_H$ | QVQLVQSGAEVKKPGSSVKVSCKASGGIFSNHAISWVRQA PGQGLEWMGGIIPIFGTANYAQKFQGRVTITADESTSTAF MELSSLRSEDTAVYYCAREWADVFDIWGQGTMVTVSS | SEQ ID NO: 83 |

In one embodiment, the anti-CD33 antibody of an ADC comprises the light chain sequence of SEQ ID NO: 84 and the heavy chain sequence of SEQ ID NO: 85. In one embodiment, the anti-CD33 antibody of an ADC comprises three light chain hypervariable regions and three heavy chain hypervariable regions, the sequences (Seq ID NO: 84-89) of which are shown below. In one embodiment, the anti-CD33 antibody of an ADC comprises the variable light chain sequence of SEQ ID NO: 90 and the variable heavy chain sequence of SEQ ID NO: 91. In one embodiment, the anti-CD33 antibody of ADC comprises the variable light chain sequence of SEQ ID NO: 92 and the variable heavy chain sequence of SEQ ID NO: 93. In one embodiment, the anti-CD33 antibody of ADCs of the present subject matter described herein comprises the variable light chain sequence of SEQ ID NO: 94 and the variable heavy chain sequence of SEQ ID NO: 95. In one embodiment, the anti-CD33 antibody of ADCs of the present subject matter described herein comprises the variable light chain sequence of SEQ ID NO: 96 and the variable heavy chain sequence of SEQ ID NO: 97.

TABLE 12

| | | |
|---|---|---|
| 9C3-HVR L1 | RASQGIRNDLG | Seq ID NO: 84 |
| 9C3-HVR L2 | AASSLQS | Seq ID NO: 85 |
| 9C3-HVR L3 | LQHNSYPWT | Seq ID NO: 86 |
| 9C3-HVR H1 | GNYMS | Seq ID NO: 87 |
| 9C3-HVR H2 | LIYSGDSTYYADSVKG | Seq ID NO: 88 |
| 9C3-HVR H3 | DGYYVSDMVV | Seq ID NO: 89 |
| 9C3 $V_L$ | DIQMTQSPSSLSASVGDRVTITCRASQGIRNDLGWYQ QKPGKAPKRLIYAASSLQSGVPSRFSGSGSGTEFTLT ISSLQPEDFATYYCLQHNSYPWTFGQGTKLEIK | Seq ID NO: 90 |
| 9C3 $V_H$ | EVQLVESGGALIQPGGSLRLSCVASGFTISGNYMSWV RQAPGKGLEWVSLIYSGDSTYYADSVKGRFNISRDIS KNTVYLQMNSLRVEDTAVYYCVRDGYYVSDMVVWGKG TTVTVSS | Seq ID NO: 91 |
| 9C3.2 $V_L$ | DIQMTQSPSSLSASVGDRVTITCRASQGIRNDLGWYQ QKPGKAPKRLIYAASSLQSGVPSRFSGSGSGTEFTLT ISSLQPEDFATYYCLQHNSYPWTFGQGTKLEIK | Seq ID NO: 92 |
| 9C3.2 $V_H$ | EVQLVESGGALIQPGGSLRLSCVASGFTISGNYMSWV RQAPGKGLEWVSLIYSGDSTYYADSVKGRFTISRDIS KNTVYLQMNSLRVEDTAVYYCVRDGYYVSDMVVWGKG TTVTVSS | Seq ID NO: 93 |
| 9C3.3 $V_L$ | DIQMTQSPSSLSASVGDRVTITCRASQGIRNDLGWYQ QKPGKAPKRLIYAASSLQSGVPSRFSGSGSGTEFTLT ISSLQPEDFATYYCLQHNSYPWTFGQGTKLEIK | Seq ID NO: 94 |
| 9C3.3 $V_H$ | EVQLVESGGALIQPGGSLRLSCVASGFTISGNYMSWV RQAPGKGLEWVSLIYSGDSTYYADSVKGRFSISRDIS KNTVYLQMNSLRVEDTAVYYCVRDGYYVSDMVVWGKG TTVTVSS | Seq ID NO: 95 |
| 9C3.4 $V_L$ | DIQMTQSPSSLSASVGDRVTITCRASQGIRNDLGWYQ QKPGKAPKRLIYAASSLQSGVPSRFSGSGSGTEFTLT ISSLQPEDFATYYCLQHNSYPWTFGQGTKLEIK | Seq ID NO: 96 |
| 9C3.4 $V_H$ | EVQLVESGGALIQPGGSLRLSCVASGFTISGNYMSWV RQAPGKGLEWVSLIYSGDSTYYADSVKGRFAISRDIS KNTVYLQMNSLRVEDTAVYYCVRDGYYVSDMVVWGKG TTVTVSS | Seq ID NO: 97 |

Antibody Affinity

In certain embodiments, an antibody provided herein has a dissociation constant (Kd) of ≤1 µM, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M. e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20®; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-

2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Linkers (L1)

As described herein, a "linker" (L1) is a bifunctional or multifunctional moiety that can be used to link one or more drug moieties (D) to an antibody (Ab) to form an ADC. In some embodiments, ADCs can be prepared using a L1 having reactive functionalities for covalently attaching to the drug and to the antibody. For example, in some embodiments, a cysteine thiol of an antibody (Ab) can form a bond with a reactive functional group of a linker or a linker L1-drug intermediate to make an ADC. Particularly, the chemical structure of the linker can have significant impact on both the efficacy and the safety of an ADC (Ducry & Stump, Bioconjugate Chem, 2010, 21, 5-13). Choosing the right linker influences proper drug delivery to the intended cellular compartment of target cells.

Linkers can be generally divided into two categories: cleavable (such as peptide, hydrazone, or disulfide) or non-cleavable (such as thioether). Peptide linkers, such as Valine-Citrulline (Val-Cit) that can be hydrolyzed by lysosomal enzymes (such as Cathepsin B) have been used to connect the drug with the antibody (U.S. Pat. No. 6,214,345). They have been particularly useful, due in part to their relative stability in systemic circulation and the ability to efficiently release the drug in tumor. However, the chemical space represented by natural peptides is limited; therefore, it is desirable to have a variety of non-peptide linkers which act like peptides and can be effectively cleaved by lysosomal proteases. The greater diversity of non-peptide structures may yield novel, beneficial properties that are not afforded by the peptide linkers. Provided herein are different types of non-peptide linkers for linker L1 that can be cleaved by lysosomal enzymes.

a. Peptidomimetic Linkers

Provided herein are different types of non-peptide, peptidomimetic linkers for ADC's that are cleavable by lysosomal enzymes. For example, the amide bond in the middle of a dipeptide (e.g. Val-Cit) was replaced with an amide mimic; and/or entire amino acid (e.g., valine amino acid in Val-Cit dipeptide) was replaced with a non-amino acid moiety (e.g., cycloalkyl dicarbonyl structures (for example, ring size=4 or 5)).

When L1 is a peptidomimetic linker, it is represented by the following formula

-Str-(PM)-Sp-, wherein:
Str is a stretcher unit covalently attached to Ab;
Sp is a bond or spacer unit covalently attached to a biologically active moiety;
PM is a non-peptide chemical moiety selected from the group consisting of:

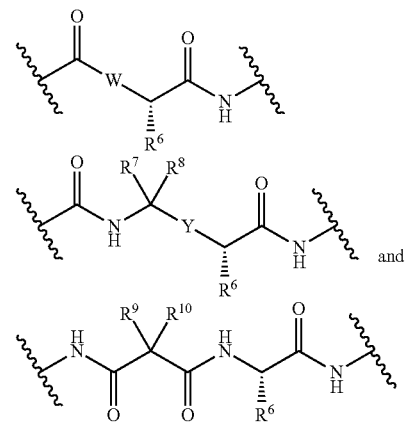

W is —NH-heterocycloalkyl- or heterocycloalkyl;
Y is heteroaryl, aryl, —C(O)$C_1$-$C_6$ alkylene, $C_1$-$C_6$ alkylene-$NH_2$, $C_1$-$C_6$ alkylene-NH—$CH_3$, $C_1$-$C_6$ alkylene-N—$(CH_3)_2$, $C_1$-$C_6$ alkenyl or $C_1$-$C_6$ alkylenyl;
each $R^6$ is independently $C_1$-$C_{10}$ alkyl, $C_1$-$C_{10}$ alkenyl, ($C_1$-$C_{10}$ alkyl)NHC(NH)$NH_2$ or ($C_1$-$C_{10}$ alkyl)NHC(O)$NH_2$;
$R^7$ and $R^8$ are each independently H, $C_1$-$C_{10}$ alkyl, $C_1$-$C_{10}$ alkenyl, arylalkyl or heteroaryl, or $R^7$ and $R^8$ together may form a $C_3$-$C_7$ cycloalkyl;
$R^9$ and $R^{10}$ are each independently $C_1$-$C_{10}$ alkyl, $C_1$-$C_{10}$ alkenyl, arylalkyl, heteroaryl, ($C_1$-$C_{10}$ alkyl)$OCH_2$—, or $R^9$ and $R^0$ may form a $C_3$-$C_7$ cycloalkyl ring;
p has a value from about 1 to about 10;
In embodiments, Y is heteroaryl; $R^9$ and $R^{10}$ together form a cyclobutyl ring.
In embodiments, Y is a moiety selected from the group consisting of:

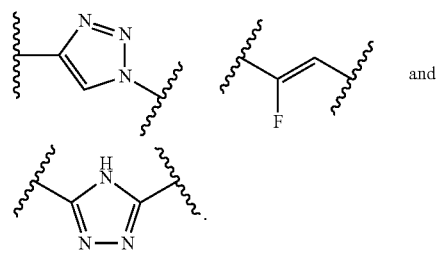

In embodiments, Str is a chemical moiety represented by the following formula:

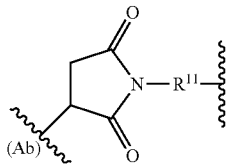

wherein $R^{11}$ is selected from the group consisting of $C_1$-$C_{10}$ alkylene, $C_1$-$C_{10}$ alkenyl, $C_3$-$C_8$ cycloalkyl, ($C_1$-$C_8$ alkylene)O—, and $C_1$-$C_{10}$ alkylene-C(O)N($R^a$)—$C_2$-$C_6$ alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$ cycloalkyl, $C_4$-$C_7$ heterocycloalkyl, aryl, arylalkyl, and heteroaryl each $R^a$ is independently H or $C_1$-$C_6$ alkyl; Sp is —Ar—$R^b$—, wherein Ar is aryl or heteroaryl, $R^b$ is ($C_1$-$C_{10}$ alkylene)O—.

In embodiments, Str has the formula:

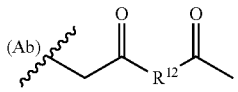

wherein $R^{12}$ is selected from $C_1$-$C_{10}$ alkylene, $C_1$-$C_{10}$ alkenyl, ($C_1$-$C_{10}$ alkylene)O—, N($R^c$)—($C_2$-$C_6$ alkylene)-N($R^c$) and N($R^c$)—($C_2$-$C_6$ alkylene); where each $R^C$ is independently H or $C_1$-$C_6$ alkyl; Sp is —Ar—$R^b$—, wherein Ar is aryl or heteroaryl, $R^b$ is ($C_1$-$C_{10}$ alkylene)O— or Sp-$C_1$-$C_6$ alkylene-C(O)NH—.

In embodiments, L is a non-peptide chemical moiety represented by the following formula

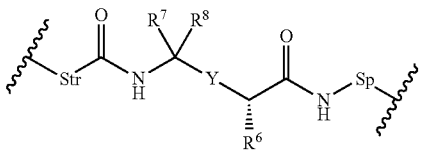

$R^6$ is $C_1$-$C_6$ alkyl, $C_1$-$C_6$ alkenyl, ($C_1$-$C_6$ alkyl)NHC(NH)NH$_2$ or ($C_1$-$C_6$ alkyl)NHC(O)NH$_2$;

$R^7$ and $R^8$ are each independently H or $C_1$-$C_{10}$ alkyl.

In embodiments, L is non-peptide chemical moiety represented by the following formula

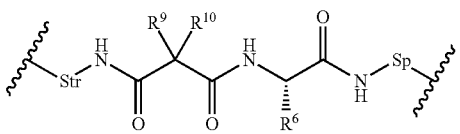

$R^6$ is $C_1$-$C_6$ alkyl, ($C_1$-$C_6$ alkyl)NHC(NH)NH$_2$ or ($C_1$-$C_6$ alkyl)NHC(O)NH$_2$;

$R^9$ and $R^{10}$ together form a $C_3$-$C_7$ cycloalkyl ring.

In embodiments, L is non-peptide chemical moiety represented by the following formula

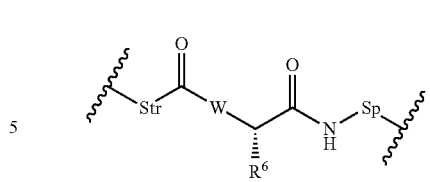

$R^6$ is $C_1$-$C_6$ alkyl, ($C_1$-$C_6$ alkyl)NHC(NH)NH$_2$ or ($C_1$-$C_6$ alkyl)NHC(O)NH$_2$.

In some embodiments, the linker may be a peptidomimetic linker such as those described in WO2015/095227, WO2015/095124 or WO2015/095223, which documents are hereby incorporated by reference in their entirety.

b. Non-Peptidomimetic Linkers

In an aspect, a Linker L1 forms a disulfide bond with the antibody, and the linker has the structure:

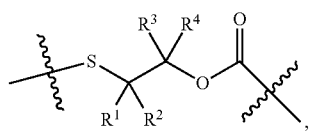

wherein $R^1$, $R^2$, $R^3$, and $R^4$ are independently selected from the group consisting of H, optionally substituted branched or linear $C_1$-$C_5$ alkyl, and optionally substituted $C_3$-$C_6$ cycloalkyl, or $R^3$ and $R^4$ taken together with the carbon atom to which they are bound form a $C_3$-$C_6$ cycloalkyl ring. The linker is covalently bound to an antibody and a drug as follows:

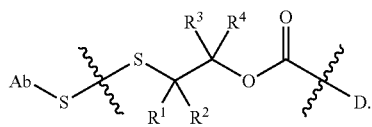

In another aspect, a linker L1 has a functionality that is capable of reacting with an antibody having a cysteine with a free thiol present to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula:

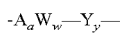

wherein A is a "stretcher unit", and a is an integer from 0 to 1; W is an "amino acid unit", and w is an integer from 0 to 12; Y is a "spacer unit", and y is 0, 1, or 2. Exemplary embodiments of such linkers are described in U.S. Pat. No. 7,498,298, which is expressly incorporated herein by reference.

In some embodiments, a linker component comprises a "stretcher unit" that links an antibody to another linker component or to a biologically active moiety. Nonlimiting exemplary stretcher units are shown below (wherein the wavy line indicates sites of covalent attachment to an antibody, biologically active, or additional linker components):

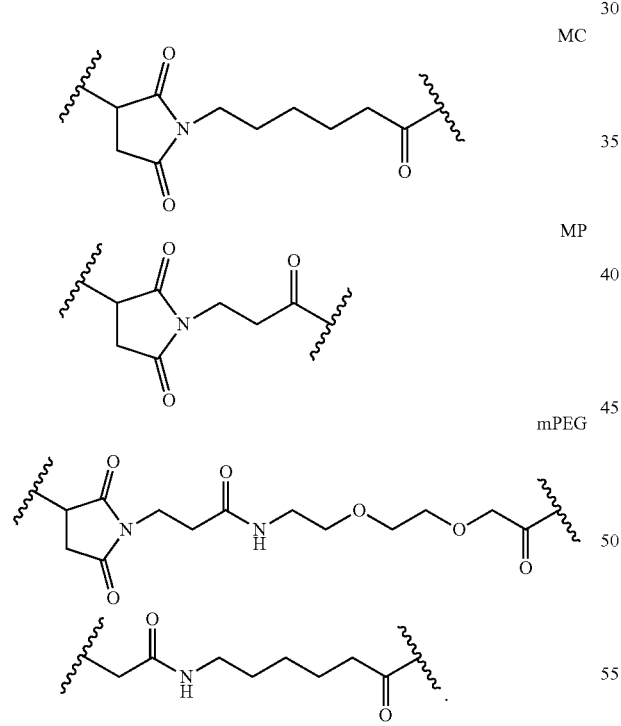

3. Drug (D)

As used herein, the term "drug" refers to a biologically active molecule comprising a secondary nitrogen-containing heteroaryl. The term "secondary nitrogen" refers to a nitrogen that is available for covalent functionalization. That is, the drug has a secondary nitrogen-containing heteroaryl group wherein said nitrogen is capable of forming a covalent bond to a linker (L1) as further defined herein. The secondary nitrogen can be present in the drug within any portion of the drug molecule, whether part of a core functionality that has been highly substituted or a pendant piece, which may or may not be substituted. For example, drugs may contain heteroaryl groups such as indoles, indazoles, benzimidazoles, benzotriazoles, pyrroles, pyrrolopyridines, imidazoles, triazoles, tetrazoles, and the like. Specific examples include, but are not limited to the following heteroaryl structures:

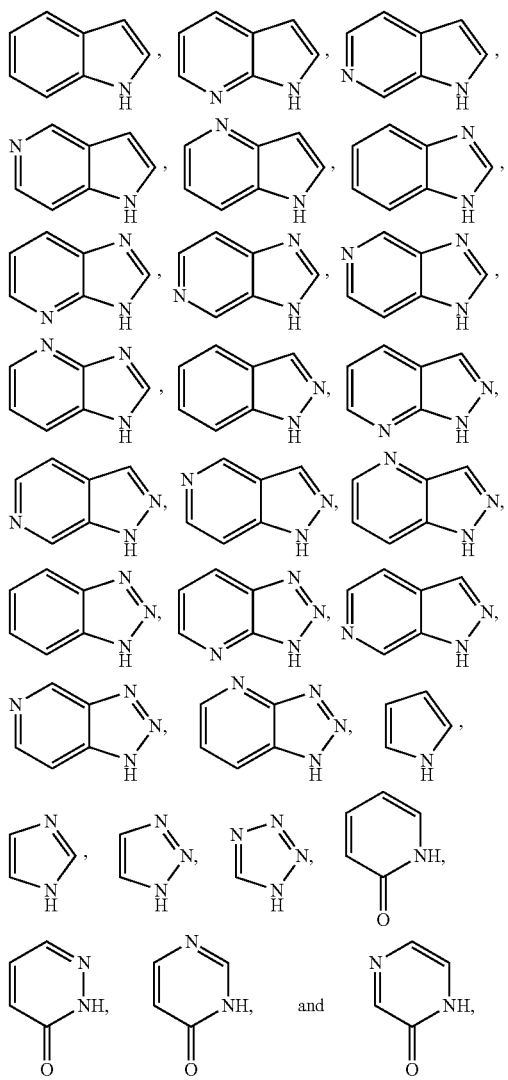

The heteroaryl groups may also exist in alternate tautomeric forms, as can be seen in such non-limiting examples as:

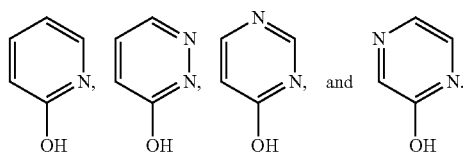

The aforementioned heteroaryl groups may be substituted in many forms, such as, for example, additional functionalization or fused rings. The secondary nitrogen can be represented in a structure as N—H. It is to be understood that this means that in the ADC, the N—H refers to the point of attachment of the drug:

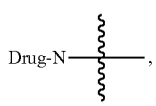

in the ADC.

As used herein, the term "biologically active molecule" refers to a small molecule capable of performing a function or an action or stimulating or responding to a function in a biological context, e.g., an organism, a cell, an in vitro model, or in vivo systems. In particular, a small molecule capable of treating a disease or condition in a subject. The function may be related to a receptor, enzyme, ion channel, target, or the like.

Useful drugs can include cytotoxic agents that inhibit or prevent a cellular function and/or causes cell death or destruction; growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; antitumor or anticancer agents, such as alkylating agents; alkyl sulfonates; aziridines; ethylenimines and methylamelamines; acetogenins (especially bullatacin and bullatacinone); antisense oligonucleotides, particularly those that inhibit expression of genes in signaling pathways implicated in aberrant cell proliferation; topoisomerase 1 inhibitors; proteosome inhibitors; EGFR inhibitors; tyrosine kinase inhibitors; serine-threonine kinase inhibitors; farnesyltransferase inhibitors; and pharmaceutically acceptable salts, acids or derivatives of any of the above.

Additional drugs include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile; selective estrogen receptor modulators (SERMs); pure anti-estrogens without agonist properties; aromatase inhibitors, including steroidal aromatase inhibitors and nonsteroidal aromatase inhibitors; lutenizing hormone-releaseing hormone agonists; sex steroids; estrogens; and androgens/retinoids; estrogen receptor down-regulators (ERDs); anti-androgens; and pharmaceutically acceptable salts, acids or derivatives of any of the above.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens; non-steroidal anti-inflammatory drugs (NSAIDs); anti-inflammatory agents; cyclooxygenase inhibitors, leukotriene receptor antagonists; purine antagonists; steroids; dihydrofolate reductase inhibitors; anti-malarial agents Non-limiting examples of drugs comprising a secondary nitrogen containing heteroaryl are amanitin, vinblastine, vincristine, duocarmycin A, duocarmycin SA, CC-1065, adozelesin, U-76074, U-73073, carzelesin (U-80244), KW-2189, diazonamide A, esomeprazole, aripiprazole, valsartan, lansoprazole, rabeprazole, pometrexed, olmesartan, tadalafil, pantoprazole, candosartan, omeprazole, sunitinib, pemetrexed, alectinib, dacarbazine, semaxanib, dacinostat, dovitinib, mebendazole, and pimobendan. Examples of drugs also include the following compounds:

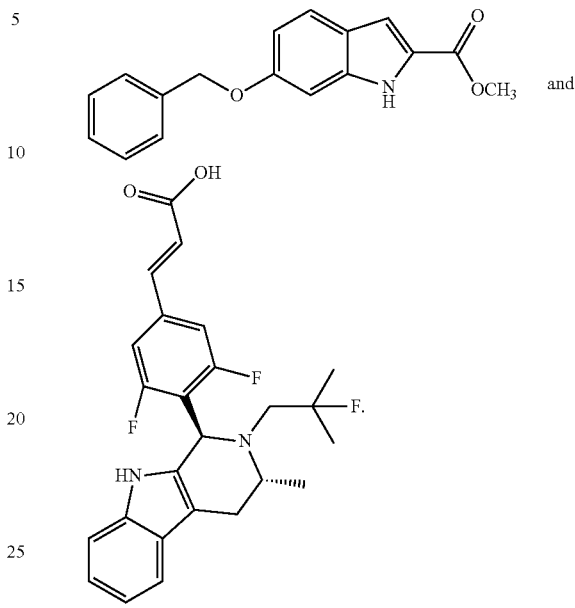

Additionally, a person of ordinary skill in the art would recognize that many more examples of biologically active molecules comprising a nitrogen-containing heteroaryl exist that have not received formal names, but still have undergone testing which would place said molecules in the category as defined herein.

The subject matter described herein also includes pharmaceutically acceptable salts of antibody-drug conjugates of Formula I.

If the antibody-drug conjugate of Formula I is cationic, or has a functional group which may be cationic (e.g. $NH_2$ may be $NH_3^+$), the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the antibody-drug conjugate of Formula I is anionic, or has a functional group which may be anionic (e.g. —COOH may be —COO⁻), the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

Illustrative examples of other suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The following examples are offered by way of illustration and not by way of limitation.

EXAMPLES

Example 1. Analytical LCMS Conditions

Condition A

Experiments were performed on a SHIMADZU 20A HPLC (with a PDA detector) with a SHIMADZU 2010EV MSD mass spectrometer using ESI as the ionization source. The LC separation was conducted using a MK RP18e 25-2 mm column with a 1.5 mL/min flow rate. Solvent A was 1.5 mL TFA per 4 L water and solvent B was 0.75 mL TFA per 4 L acetonitrile. The gradient consisted of 5-95% solvent B over 0.7 min followed by holding at 95% B for 0.4 min, followed by equilibration for 0.4 min. LC column temperature was 50° C. UV absorbance was monitored at 220 nm and 254 nm, and mass spec full scan was applied to all experiments.

Condition B

Experiments were performed on an Agilent 1290 UHPLC coupled with an Agilent MSD (6140) mass spectrometer using ESI as the ionization source. The LC separation was conducted using a Phenomenex XB-C18, 1.7 um, 50×2.1 mm column with a 0.4 mL/min flow rate. Solvent A was water with 0.1% formic acid and solvent B was acetonitrile with 0.1% formic acid. The gradient consisted of 2-98% solvent B over 7 min followed by holding at 98% B for 1.5 min, followed by equilibration for 1.5 min. LC column temperature was 40° C. UV absorbance was monitored at 220 nm and 254 nm, and mass spec full scan was applied to all experiments.

Condition C

Experiments were performed on a Waters Acquity UPLC with a Waters LCT Premier XE mass spectrometer using ESI ionization. The LC separation was conducted using an Acquity UPLC BEH C18, 1.7 um, 2.1×50 mm column and a 0.6 mL/min flow rate. Solvent A was water with 0.05% TFA and solvent B was acetonitrile with 0.05% TFA. The gradient consisted of 2-98% solvent B over 5 min followed by holding at 98% B for 0.5 min followed by equilibration for 0.5 min. LC column temperature was 40° C. UV absorbance was monitored at 220 nm and 254 nm, and mass spec full scan was applied to all experiments.

Example 2. Synthesis of (E)-3-(3,5-difluoro-4-((1R, 3R)-2-(2-fluoro-2-methylpropyl)-3-methyl-9-(((R)-2-((5-nitropyridin-2-yl)disulfaneyl)propoxy)carbonyl)-2,3,4,9-tetrahydro-1H-pyrido[3,4-b]indol-1-yl)phenyl)acrylic acid (Compound 8)

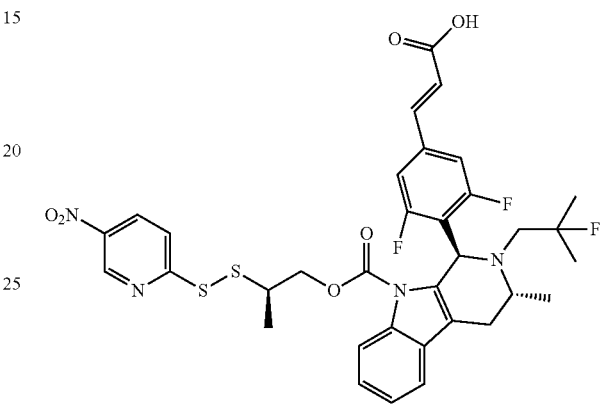

8

Step 1: (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid

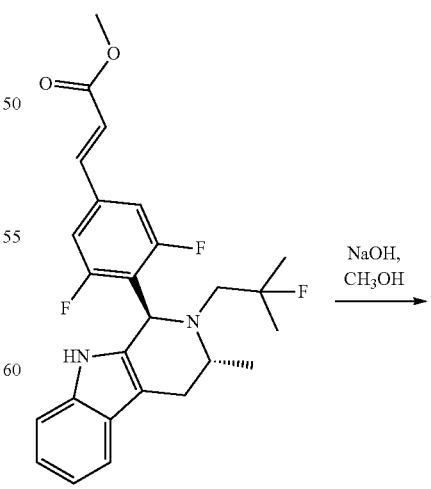

1

NaOH, CH₃OH

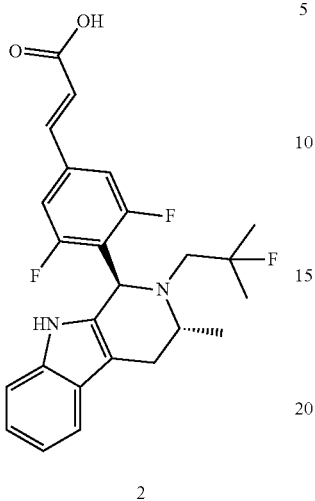

2

To a solution of compound 1 (prepared according to: *J. Med. Chem.* 2015, 58, 8128; 500 mg, 1.1 mmol) in MeOH (100 mL)/water (25 mL) was added a NaOH solution in water (3.0 M, 9.0 mL, 27 mmol). After the mixture was stirred at 25° C. for 18 h, it was concentrated to about 5.0 mL, poured into 1.0 M HCl (10 mL), and extracted with EtOAc (3×50.0 mL). The combined organic layers were dried over Na₂SO₄ and concentrated to give the crude 2 (400 mg, 83%) as a yellow solid. This material was used directly in the next step.

Step 2: tert-butyl (E)-3-(3,5-difluoro-4-((1R,3R)-2-(2-fluoro-2-methylpropyl)-3-methyl-2,3,4,9-tetra-hydro-1H-pyrido[3,4-b]indol-1-yl)phenyl)acrylate

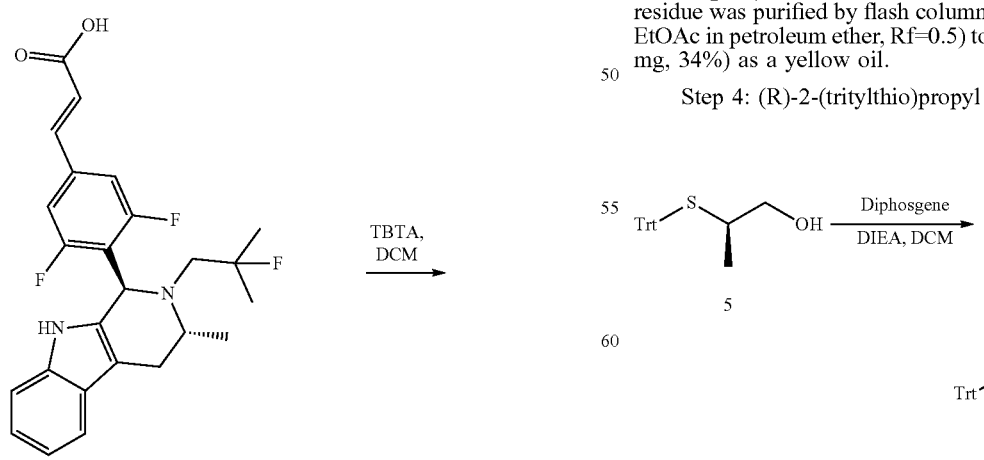

2

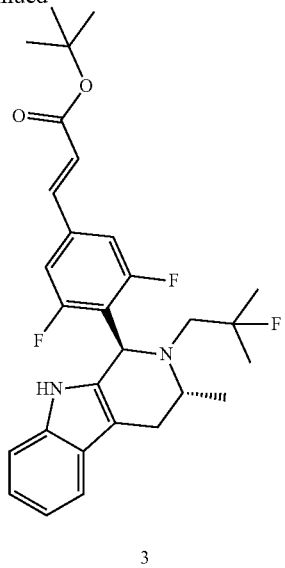

3

To a solution of compound 2 (400.0 mg, 0.90 mmol) in DCM (5.0 mL) was added tert-butyl 2,2,2-trichloroacetimidate (15 mL, 83.89 mmol). The mixture was stirred at 25° C. for 60 h, washed with water (3×50.0 mL), brine (50.0 mL), and dried over Na₂SO₄. The organic layer was concentrated and purified by column chromatography (10% EtOAc in petroleum ether) to give 3 (310 mg, 69%) as a yellow solid.

Step 3: (R)-2-(tritylthio)propan-1-ol

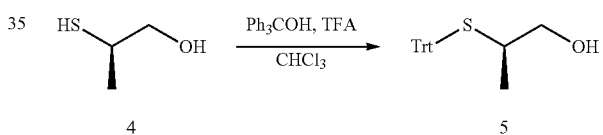

TFA (0.40 mL, 5.23 mmol) was added to a solution of compound 4 (prepared as described in: WO 2013055987; 482.0 mg, 5.23 mmol) and triphenylmethanol (953 mg, 3.66 mmol) in CHCl₃ (25 mL). The mixture was stirred at 25° C. for 5 h and then diluted with DCM (25 mL). The resulting solution was washed with sat. NaHCO₃ (50.0 mL), dried over Na₂SO₄, and concentrated under reduced pressure. The residue was purified by flash column chromatography (20% EtOAc in petroleum ether, Rf=0.5) to give compound 5 (600 mg, 34%) as a yellow oil.

Step 4: (R)-2-(tritylthio)propyl carbonochloridate

To a solution of compound 5 (600 mg, 1.79 mmol) in DCM (5.0 mL) was added diphosgene (497 mg, 2.51 mmol) over 2 min at 0° C. DIEA (232 mg, 1.79 mmol) was then added over 1 min. The mixture was stirred at 0° C. for 1 h and then at 25° C. for 2.0 h. The reaction mixture was concentrated and dissolved in THF (1.0 mL). Heptanes were then added until a white solid appeared. This solid was removed by filtration through celite. The filtrate was concentrated under reduced pressure to give compound 6 (710 mg, 99.7%) as a white solid. This material was used directly in next step.

Step 5: (R)-2-(tritylthio)propyl (1R,3R)-1-(4-((E)-3-(tert-butoxy)-3-oxoprop-1-en-1-yl)-2,6-difluorophenyl)-2-(2-fluoro-2-methylpropyl)-3-methyl-1,2,3,4-tetrahydro-9H-pyrido[3,4-b]indole-9-carboxylate

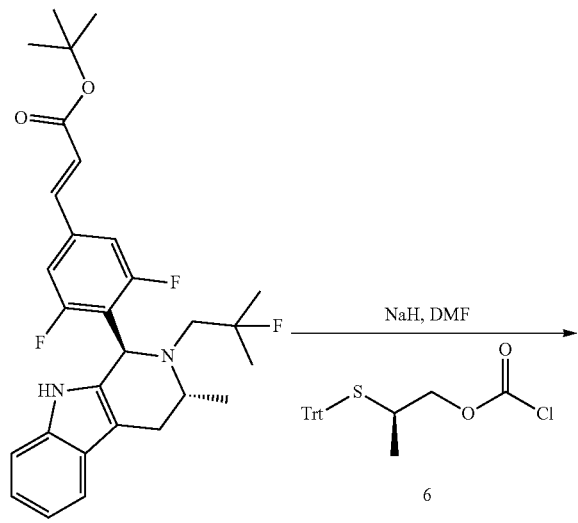

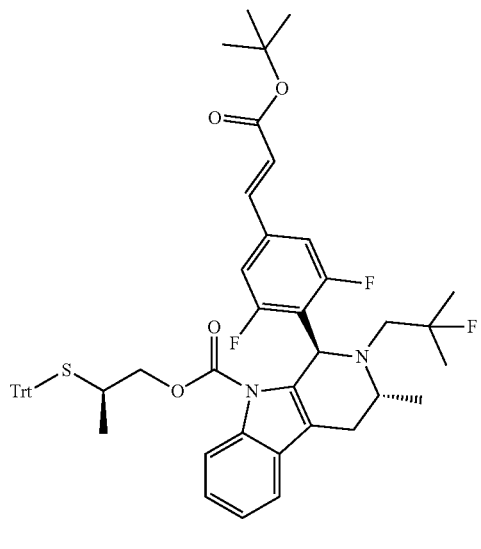

To a solution of compound 3 (140.0 mg, 0.280 mmol) in DMF (2.0 mL) was added sodium hydride (60%, 7.41 mg, 0.310 mmol) at 0° C. The resulting mixture was stirred at 25° C. for 30 min and a solution of compound 6 (111 mg, 0.280 mmol) in DMF (1.0 mL) was then added. After the mixture was stirred at 25° C. for 1.0 h, it was concentrated under reduced pressure and the residue purified by column chromatography (10% EtOAc in petroleum ether, Rf=0.6) to afford compound 7 (92 mg, 38%). LCMS (Condition A): $R_T$=1.12 min, m/z=859.3 [M+H]$^+$.

Step 6: (E)-3-(3,5-difluoro-4-((1R,3R)-2-(2-fluoro-2-methylpropyl)-3-methyl-9-(((R)-2-((5-nitropyridin-2-yl)disulfaneyl)propoxy)carbonyl)-2,3,4,9-tetrahydro-1H-pyrido[3,4-b]indol-1-yl)phenyl)acrylic acid

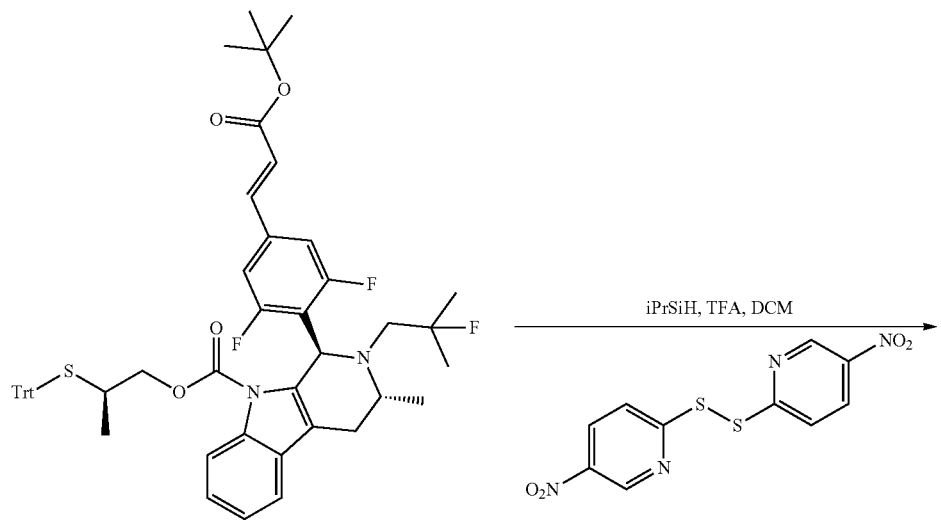

-continued

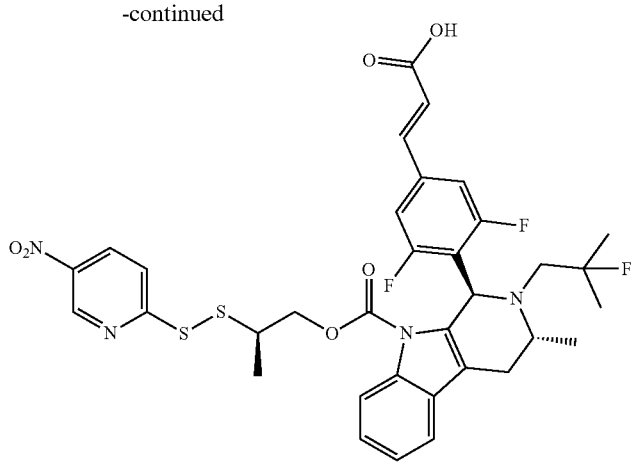

8

TFA (0.30 mL) was added to a solution of compound 7 (80.0 mg, 0.090 mmol), triisopropylsilane (16.2 mg, 0.10 mmol), and 2,2'-dithiobis(5-nitropyridine) (86.7 mg, 0.280 mmol) in DCM (1.0 mL). After the mixture was stirred at 25° C. for 18 h, toluene (40.0 mL) was added. The mixture was concentrated and the residue purified by column chromatography (50% EtOAc in petroleum ether) to afford compound 8 (27.2 mg, 37%) as a yellow solid. LCMS (Condition A): $R_T$=0.92 min, m/z=715.0 [M+Na]$^+$; $^1$H NMR (400 MHz, CDCl$_3$) δ 9.12 (s, 1H), 8.10-8.04 (m, 2H), 7.70-7.68 (d, J=8.8 Hz, 1H), 7.51-7.42 (m, 2H), 7.24-7.23 (m, 3H), 7.12-6.89 (m, 1H), 6.32-6.28 (d, J=15.9 Hz, 1H), 5.76 (br, 1H), 4.22-4.18 (m, 2H), 3.27-3.15 (m, 1H), 2.67-2.45 (m, 4H), 2.22-2.11 (m, 1H), 1.41-1.36 (m, 3H), 1.19-1.07 (m, 3H), 0.89-0.81 (m, 3H).

Example 3. Synthesis of (E)-3-(3,5-difluoro-4-((1R, 3R)-2-(2-fluoro-2-methylpropyl)-3-methyl-9-((2-((5-nitropyridin-2-yl)disulfaneyl)ethoxy)carbonyl)-2,3,4, 9-tetrahydro-1H-pyrido[3,4-b]indol-1-yl)phenyl) acrylic acid (Compound 13)

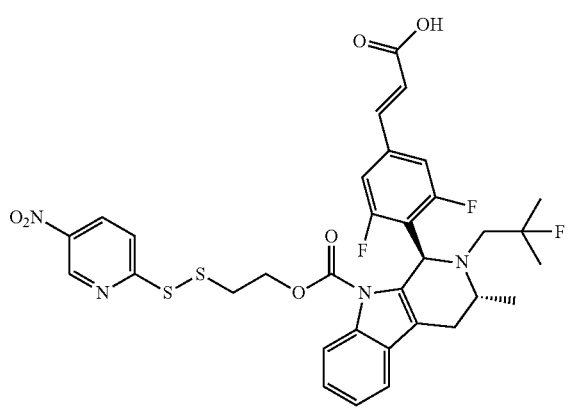

13

Step 1: 2-(tritylthio)ethan-1-ol

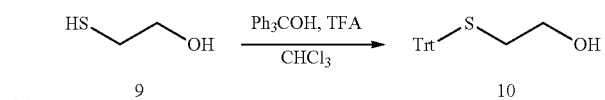

TFA (2.2 mL, 28 mmol) was added to a solution of compound 9 (2.0 mL, 28.5 mmol) and triphenylmethanol (5.2 g, 20 mmol) in CHCl$_3$ (100 mL). The mixture was stirred at 25° C. for 4 h and then diluted with DCM (75 mL). The resulting solution was washed with sat. NaHCO$_3$ (200 mL), dried over MgSO$_4$, filtered, and concentrated under reduced pressure. The residue was purified by flash column chromatography (0-40% iPrOAc in heptanes) to give compound 10 (2.1 g, 33%) as a white solid. $^1$H NMR (400 MHz, CDCl$_3$) δ 7.47-7.38 (m, 5H), 7.32-7.15 (m, 10H), 3.41 (q, J=6.2 Hz, 2H), 2.48 (t, J=6.2 Hz, 2H), 1.48 (t, J=6.1 Hz, 1H).

Step 2: 2-(tritylthio)ethyl carbonochloridate

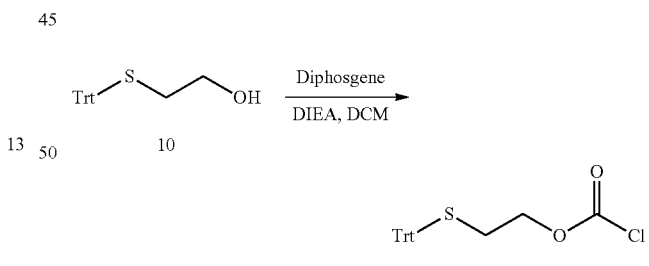

To a solution of compound 10 (1.5 mg, 4.7 mmol) in DCM (30 mL) was added diphosgene (1.3 g, 6.6 mmol) over 2 min at 0° C. DIEA (0.82 mL, 4.7 mmol) was then added over 1 min. The mixture was stirred at 0° C. for 1 h and then at 25° C. for 3 h. The reaction mixture was concentrated and redissolved in THF (10 mL). Heptanes were added until a white solid appeared (approximately 30 mL). This solid was removed by filtration through celite. The filtrate was concentrated under reduced pressure to give crude compound 11 as a yellow oil. This material was used directly in the next step.

Step 3: 2-(tritylthio)ethyl (1R,3R)-1-(4-((E)-3-(tert-butoxy)-3-oxoprop-1-en-1-yl)-2,6-difluorophenyl)-2-(2-fluoro-2-methylpropyl)-3-methyl-1,2,3,4-tetrahydro-9H-pyrido[3,4-b]indole-9-carboxylate

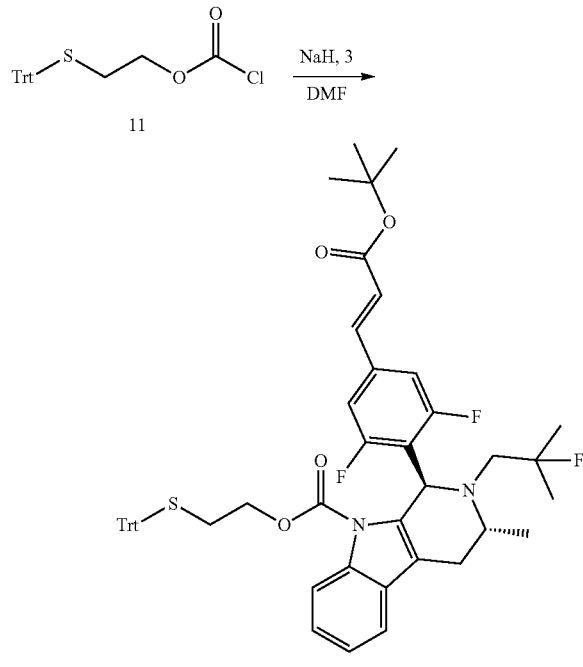

Sodium hydride (60%, 61 mg, 1.53 mmol) was added to a solution of compound 3 (693 mg, 1.39 mmol) in DMF (25 mL) at 0° C. The resulting mixture was stirred at 25° C. for 30 min and a solution of compound 11 (532 mg, 1.39 mmol) in DMF (5.0 mL) was then added. After the mixture was stirred at 25° C. for 10 min, the volatiles were removed under reduced pressure. The residue was partitioned between iPrOAc (2×150 mL) and 0.5 M HCl (150 mL). The combined organic layers were dried over MgSO$_4$, filtered, and concentrated under reduced pressure. The residue was purified by column chromatography (0-20% iPrOAc in heptanes) to afford compound 12 (189 mg, 16%) as a white foam. $^1$H NMR (400 MHz, CDCl$_3$) δ 8.14 (d, J=7.5 Hz, 1H), 7.49-7.13 (m, 11H), 6.79 (d, J=10.5 Hz, 2H), 6.23 (d, J=15.9 Hz, 1H), 5.74-5.70 (m, 1H), 4.99 (hept, J=6.3 Hz, 1H), 3.86 (t, J=7.0 Hz, 1H), 3.84-3.76 (m, 1H), 3.72-3.62 (m, 1H), 3.36-3.24 (m, 1H), 2.68 (dd, J=16.7, 4.6 Hz, 1H), 2.63-2.42 (m, 6H), 2.36-2.27 (m, 1H), 1.54 (s, 3H), 1.53 (s, 9H), 1.44 (d, J=21.7 Hz, 3H), 1.27 (d, J=21.1 Hz, 3H), 1.12 (d, J=6.7 Hz, 3H).

Step 4: (E)-3-(3,5-difluoro-4-((1R,3R)-2-(2-fluoro-2-methylpropyl)-3-methyl-9-((2-((5-nitropyridin-2-yl)disulfaneyl)ethoxy)carbonyl)-2,3,4,9-tetrahydro-1H-pyrido[3,4-b]indol-1-yl)phenyl)acrylic acid

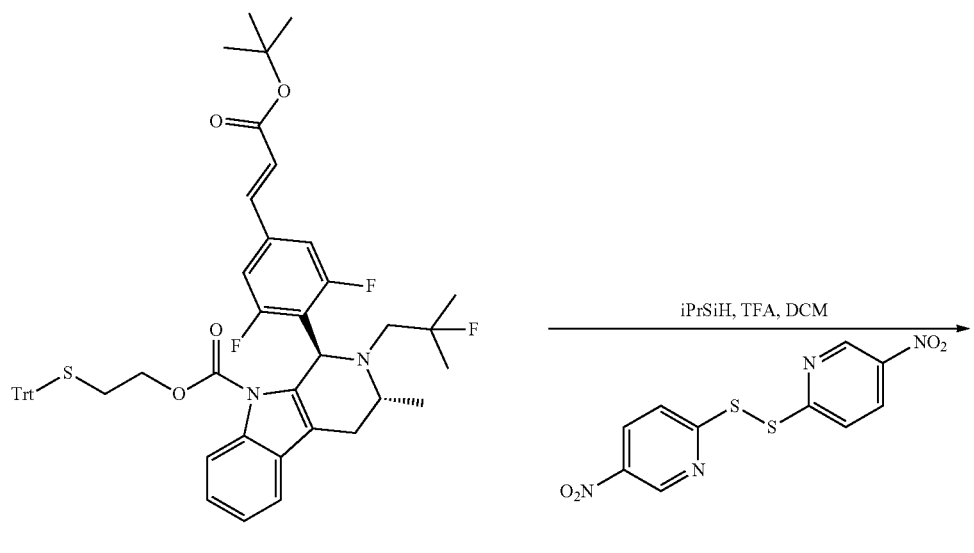

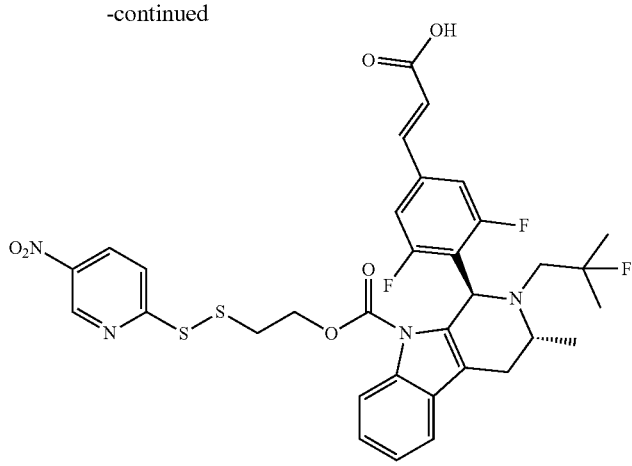

13

TFA (0.30 mL) was added to a solution of compound 12 (18 mg, 0.021 mmol), triisopropylsilane (16.2 mg, 0.10 mmol), and 2,2'-dithiobis(5-nitropyridine) (20 mg, 0.064 mmol) in DCM (1.0 mL). After the mixture was stirred at 25° C. for 16 h, toluene (40.0 mL) was added. The mixture was concentrated and the residue purified by reverse phase HPLC (Column=Gemini-NX C18 5um, 110A, 50×30 mm, temp=25° C.; Eluents: A=0.1% formic acid in water, B=acetonitrile; 50-90% B over 10 min, flow=60 mL/min; detection=270 nM) to afford compound 13 (7.0 mg, 50%) as an off-white solid. LCMS (Condition B): $R_T$=7.24 min, m/z=701.2 [M+H]$^+$; $^1$H NMR (400 MHz, DMSO-d$_6$) δ 9.13 (d, J=2.6 Hz, 1H), 8.36 (dd, J=8.8, 2.7 Hz, 1H), 8.09-7.99 (m, 1H), 7.91 (d, J=8.9 Hz, 1H), 7.59-7.50 (m, 1H), 7.43 (d, J=16.0 Hz, 1H), 7.33-7.25 (m, 3H), 6.58 (d, J=16.0 Hz, 1H), 5.75 (s, 1H), 4.50-4.35 (m, 2H), 3.23-3.03 (m, 5H), 2.80-2.52 (m, 4H), 1.39 (d, J=21.5 Hz, 3H), 1.26 (d, J=21.1 Hz, 3H), 1.10 (d, J=6.7 Hz, 3H).

Example 4. Synthesis of 1-(4-((S)-2-((S)-2-((tert-butoxycarbonyl)amino)-3-methylbutanamido)-5-ureidopentanamido)benzyl) 2-methyl 6-(benzyloxy)-1H-indole-1,2-dicarboxylate (Compound 17)

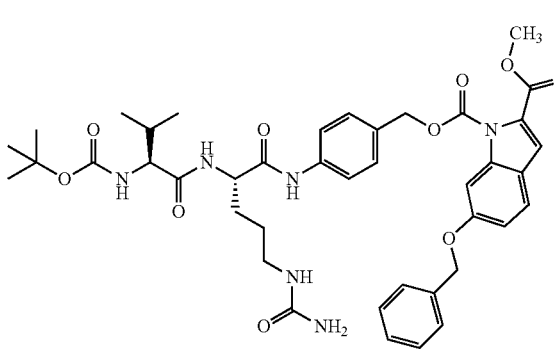

17

Step 1: 2-methyl 1-(4-nitrophenyl) 6-(benzyloxy)-1H-indole-1,2-dicarboxylate

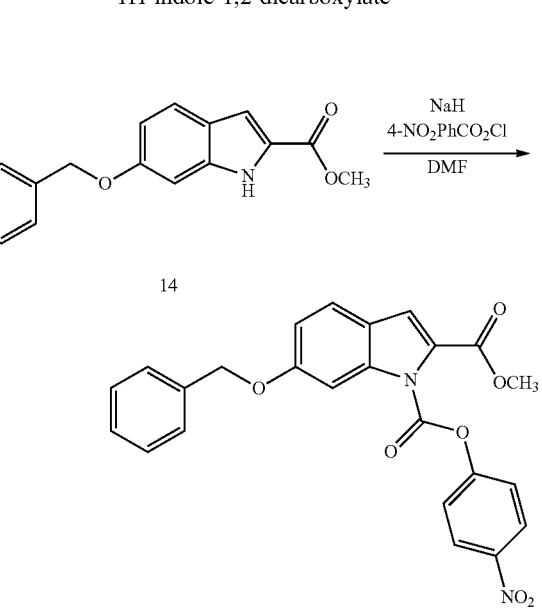

Sodium hydride (60%, 235 mg, 5.88 mmol) was added to a solution of compound 14 (1.74 g, 6.19 mmol) in THF (50 mL) at 0° C. The resulting mixture was stirred at 25° C. for 2.5 h and a solution of 4-nitro-phenylchloroformate (1.22 g, 5.88 mmol) in THF (15 mL) was added. After the mixture was stirred at 25° C. for 4.0 h, it was filtered through Celite. The filtrate was concentrated under reduced pressure to afford a yellow oil. This material was dissolved in a mixture of Et$_2$O (100 mL) and heptanes (40 mL) and the resulting solution was concentrated under reduced pressure until a solid appeared (approximately 80 mL volume). The solid was collected by vacuum filtration and air-dried overnight to give crude 15 (1.22 g) that was contaminated with a significant amount (ca. 33%) of an unknown impurity. This material was used in the next step without further purification.

Step 2: 1-(4-((S)-2-((S)-2-((tert-butoxycarbonyl)amino)-3-methylbutanamido)-5-ureidopentanamido)benzyl) 2-methyl 6-(benzyloxy)-1H-indole-1,2-dicarboxylate

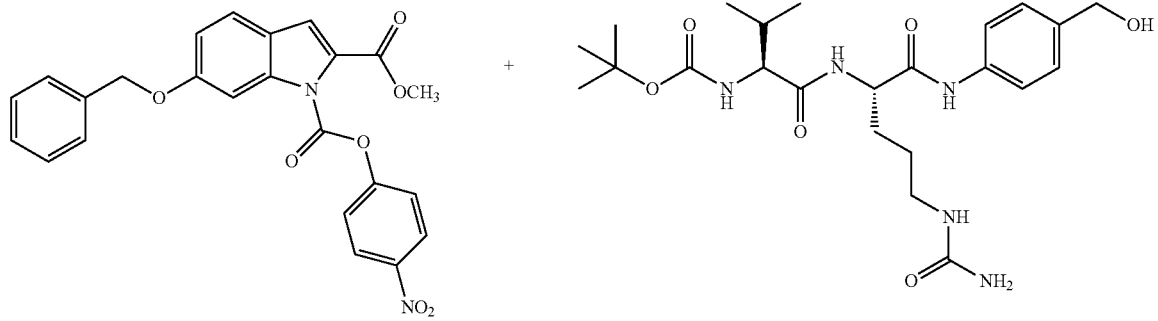

15       16

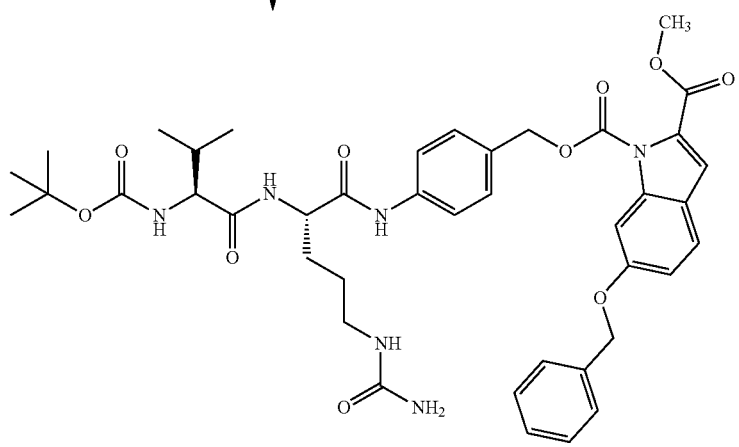

17

A solution of crude compound 15 (135 mg, approx 0.252 mmol), di-peptide 16 (prepared as described in: WO 2015162293 and WO 2015162293; 0.028 g, 0.036 mmol), and DMAP (0.030 g, 0.246 mmol) in DMF (10 mL) was stirred at 25° C. for 5 days. The volatiles were then removed under reduced pressure and the residue purified by preparative HPLC (Column=Gemini-NX C18 5 um, 110A, 50×30 mm, temp=25° C.; Eluents: A=0.1% ammonium hydroxide in water, B=acetonitrile; 40-80% B over 10 min, flow=60 mL/min; detection=254 nM) to give compound 17 (0.028 g, 14%) as an off-white solid. LCMS (Condition B): $R_T$=6.22 min, m/z=787.4 [M+H]$^+$; $^1$H NMR (400 MHz, DMSO-d) δ 10.13 (s, 1H), 7.99 (d, 0.1=7.7 Hz, 1H), 7.69-7.59 (m, 3H), 7.54 (d, J=2.3 Hz, 1H), 7.48-7.30 (m, 7H), 7.28 (d, J=0.8 Hz, 1H), 7.04 (dd, J=8.7, 2.3 Hz, 1H), 6.74 (d, J=8.9 Hz, 1H), 5.95 (t, J=5.9 Hz, 1H), 5.40 (br s, 2H), 5.36 (s, 2H), 5.09 (s, 2H), 4.50-4.41 (m, 1H), 3.87-3.81 (m, 1H), 3.71 (s, 3H), 3.07-2.88 (m, 2H), 2.01-1.90 (m, 1H), 1.73-1.52 (m, 2H), 1.38 (s, 9H), 0.86 (d, J=6.8 Hz, 3H), 0.81 (d, J=6.8 Hz, 3H).

Example 5. Synthesis of 2-methyl 1-(2-(tritylthio)ethyl) 6-(benzyloxy)-1H-indole-1,2-dicarboxylate (Compound 18)

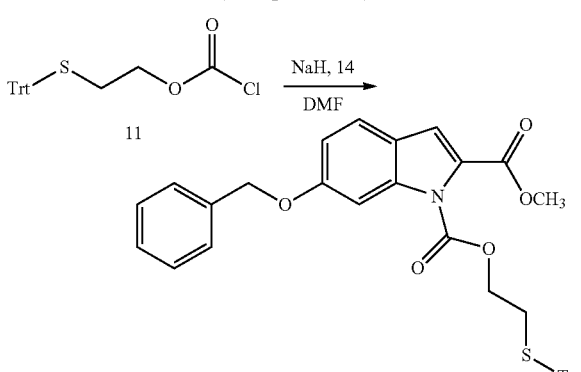

18

Sodium hydride (60%, 78 mg, 1.96 mmol) was added to a solution of compound 14 (500 mg, 1.78 mmol) in DMF (15 mL) at 0° C. The resulting mixture was stirred at 25° C. for 45 min and a solution of compound 11 (681 mg, 1.78 mmol) in DMF (5.0 mL) was then added. After the mixture was stirred at 25° C. for 1.0 h, it was partitioned between iPrOAc (2×150 mL) and 0.5 M HCl (150 mL). The combined organic layers were dried over $MgSO_4$, filtered, and concentrated under reduced pressure. The residue was purified by column chromatography (0-30% iPrOAc in heptanes) to afford compound 18 (440 mg, 39%) as a white foam. LCMS (Condition C): $R_T$=5.26 min, m/z=628.1 [M+H]$^+$; $^1$H NMR (400 MHz, DMSO-$d_6$) δ 7.63 (dd, J=8.7, 0.4 Hz, 1H), 7.56 (dt, J=2.2, 0.6 Hz, 1H), 7.44-7.20 (m, 21H), 7.05 (dd, J=8.7, 2.3 Hz, 1H), 5.15 (s, 2H), 4.13 (t, J=6.3 Hz, 2H), 3.75 (s, 3H), 2.57 (t, J=6.3 Hz, 2H).

Example 6. Synthesis of Antibody-Drug Conjugates

Anti-HER2 7C2 LC K149C and anti-B7H4 1D11 LC K149C were conjugated to compound 8 or compound 13 via the engineered LC K149C cysteine residues. Solutions of a given antibody at 10 mg/mL in 50 mM Tris pH 8.5 were reduced with 50 molar excess of DTT at ambient temperature for 16-18 hours. The reduced antibody was purified using SP HP cationic exchange chromatography. The purified antibody in 50 mM Tris pH 8 was re-oxidized using 15 molar excess of DHAA dissolved in DMA at ambient temperature for 2-3 hours. The antibody was again purified using SP HP cationic exchange column to remove DHAA and aggregates. Three to five-fold molar equivalents of compound 8 or 13 in DMF were added to a 5 to 10 mg/mL solution of the purified antibody in 100 mM Tris pH 8.5-9.0 followed by additional DMF for a final concentration of 10% DMF. The coupling reaction was then incubated at ambient temperature for 3 to 4 hours. The conjugated antibody was purified using either of the following methods: cationic exchange chromatography using HiTrap SP HP resin or by Zeba spin 7 kDa MWCO desalting resin followed by removal of excess free drug using dextran coated charcoal. The resulting purified conjugate was formulated using dialysis with 10 kDa MWCO Slide-a-Lyzer dialysis cassette into 20 mM histidine acetate pH 5.5, 240 mM sucrose, 0.02% polysorbate-20.

Conjugates produced using the conjugation reaction conditions and either of the purification schemes typically afforded protein yields of 50 to 80%. All of the conjugates were characterized in regards to aggregation (SEC HPLC), drug to antibody ratio (LC/MS), percent of nitro-pyridyl disulfide (nitroPDS) species conjugated (LC/MS) and amount of free drug (LC/MS) present in the final conjugates. In all of the conjugates, <5% of the conjugated species to the antibody were nitroPDS resulting from conjugation to the nitroPDS sulfur rather than the sulfur on the drug side of the disulfide bond. Detailed characterization data for each conjugate are provided in Table 13 below.

TABLE 13

| CNJ lot | Antibody | Linker Drug | DAR | nitroPDS | Aggregation | Free drug content | Yield |
|---|---|---|---|---|---|---|---|
| CNJ-1 | Anti-HER2 7C2 LC K149C | Compound 13 | 1.9 | 4.9% | 1.5% | <5% | 55% |
| CNJ-2 | Anti-B7H4 1D11v1.9 varD LC K149C | Compound 13 | 1.9 | 1.9% | 3.9% | <5% | 52% |
| CNJ-3 | Anti-HER2 7C2 LC K149C | Compound 8 | 2.0 | 0.5% | 0.5% | <2% | 70% |
| CNJ-4 | Anti-B7H4 1D11v1.9 varD LC K149C | Compound 8 | 2.0 | 0.6% | 0.6% | <2% | 77% |

Example 7. Biological Assays

Whole Blood Sample Preparation

Stability samples were generated in mouse (CB17 SCID), rat (Sprague-Dawley), cynomologus monkey and human whole blood plasma as well as buffer (0 and 24 h time-points). Blood was collected by bioreclamation, then shipped cold overnight, and samples were created immediately on arrival. To create stability samples, initial dilutions of the source conjugates were made in buffer (1×PBS, 0.5% BSA, 15 ppm proclin) so that all molecules were 1 mg/mL in concentration. Then a 1:10× dilution (36 uL of 1 mg/mL initial dilution+324 uL blood or buffer) was performed to generate the stability samples with a final compound concentration of 100 ug/mL. Once mixed, 150 μL of the whole blood/buffer stability samples was aliquoted into two separate sets of tubes for the two different time points. The 0 h time points were then placed in a −80° C. freezer, while the 24 h time points were placed on a shaker in a 37° C. incubator. When the 24 h samples reached the given time point they were also placed in the −80° C. freezer.

Affinity-Capture LC-MS Assays for Stability Determination of Whole Blood Samples The whole blood stability samples were evaluated using an affinity-capture LC-MS assay. First, streptavidin-coated magnetic beads (Life Technologies Corporation, Grand Island, N.Y.) were washed 2× with HBS-EP buffer (GE Healthcare, Sunnyvale, Calif.), then mixed with biotinylated HER2 anti-idiotypic antibody using the KingFisher Flex (Thermo Fisher Scientific, Waltham, Mass.) and incubated for 2 h at room temperature with gentle agitation. After 2 h, the SA-bead/biotin-xId Ab complex was washed 2× with HBS-EP buffer, mixed with the diluted whole blood stability samples and then incubated for 2 h at room temperature with gentle agitation. After 2 h, the SA-bead/biotin-xId Ab/sample complex was washed 2× with HBS-EP buffer, mixed with the deglycosylation enzyme PNGase F (New England BioLabs, Ipswich, Mass.) and incubated overnight at 37° C. with gentle agitation. After the overnight incubation, the deglycosylated SA-bead/biotin-xId Ab/sample complex was washed 2× with HBS-EP buffer, followed by 2× washes with water (Optima $H_2O$, Fisher Scientific, Pittsburgh, Pa.) and finally a 1× wash with 10% acetonitrile. The beads were placed in 300% acetonitrile/0.1% formic acid for elution where they were incubated for 30 min at room temperature with gentle agitation before the beads were collected. The eluted samples were injected and loaded onto a Thermo Scientific PepSwift RP monolithic column (500 μm×5 cm) maintained at 65° C. The samples were separated on the column using a Waters Acquity UPLC system at a flow rate of 20 μL/min with the following gradient: 20% B (95% acetonitrile+0.1% formic acid) at 0-2 min; 35% B at 2.5 min; 65% B at 5 min; 95% B at 5.5 min; 5% B at 6 min. The column was directly coupled for online detection with a Waters Synapt G2-S Q-ToF mass spectrometry operated in positive ESI with an acquisition mass range from 500 to 5000 Th (m/z).

Breast Cancer Cell ERα High Content Fluorescence Imaging Assay (F10)

MCF7-neo/HER2 breast cancer cells were seeded on day 1 at a density of 10,000 cells per well in 384 well poly-lysine coated tissue culture plate (Greiner #T-3101-4), in 50 uL/well RPMI (phenol red free), 10% FBS (Charcoal stripped), containing L-glutamine. On day-2, Antibody Conjugates were thawed at RT and were each diluted to 60 ug/mL in 37° C. growth media, followed by a 20-point 2× serial dilution across a 384 well plate (Ref: 781091). 10 uL of each sample from the serial dilution was transferred to the wells of the cell plates. The highest working concentration of the ADCs was 10 ug/mL. Cell plate columns 1, 2, 23 and 24 were left untreated for data normalization while Columns 3-22 contained the ADC dilutions. After compound treatment, cell plates were stored in a 37° C. incubator for 72 h. Fixation and permeabilization were carried out using a Biotek EL406 plate washer and dispenser on day-5 as follows. Cells were fixed by addition of 15 uL of 16% paraformaldehyde (Electron Microscopy Sciences #15710-S) directly to the 50 uL cell culture medium in each well using the peristaltic pump 5 uL cassette on a Biotek EL406 (final concentration of formaldehyde was 3.7%/c w/v). Samples were incubated 30 minutes. Well contents were aspirated and 50 uL/well of Phosphate Buffered Saline (PBS) containing 0.5% w/v bovine serum albumen and 0.5% v/v Triton X-100 (Antibody Dilution Buffer) were added to each well. Samples were incubated for 30 minutes. The well contents were aspirated and washed 3 times with 100 uL/well of PBS. Immunofluorescence staining of estrogen receptor alpha (ESR1) was carried out using a Biotek EL406 plate washer and dispenser as follows. The well supernatant was aspirated from the wells and 25 uL/well of anti-ESR1 mAb (F10) (Santa Cruz sc-8002) diluted 1:1000 in Antibody Dilution Buffer was dispensed. Samples were incubated for 2 hours at room temperature and then washed 4 times with 100 uL/well of PBS. 25 uL/well of secondary antibody solution (Alexafluor 488 conjugate anti-mouse IgG (LifeTechnologies #A21202) diluted 1:1000 and Hoechst 33342 1 ug/mL diluted in Antibody Dilution Buffer) were dispensed into each well. The samples were incubated for 2 hours at room temperature and then washed 3 times with 100 uL/well of PBS using a Biotek EL406. Quantitative fluorescence imaging of ESR1 was carried out using a Cellomics Arrayscan V (Thermo). Fluorescence images of the samples [Channel 1: XF53 Hoechst (DNA stain); Channel 2: XF53 FITC (ESR1 stain)] were acquired using a Cellomics VTI Arrayscan using the Bioapplication "Compartmental Analysis" using the auto-exposure (based on DMSO control wells) setting "peak target percentile" set to 25% target saturation for both channels. Channel 1 (DNA stain) was used to define the nuclear region (Circ). Measurements of "Mean_CircAvgIntCh2", which is the Alexafluor 488 fluorescence intensity (ESR1) within the nuclear region, was measured on a per cell basis and averaged over all the measured cells. Data analysis was carried out using GraphPad Prism 6, with DMSO and no primary antibody control treated samples being used to define the 0% and 100% changes in ESR1. The dose-response log(inhibitor) vs. response was used to define the inflexion point of curve ($EC_{50}$) and the plateau of the maximal effect.

In Vivo Modulation of ERα Levels in MCF7-Neo/HER2 Derived Tumors

Human breast cancer MCF7 cells were originally obtained from American Type Culture Collection (Rockville, Md.) and were engineered at Genentech to overexpress HER2 to generate MCF7-neo/HER2. Four days prior to tumor cell implantation, 55 female NCR nude mice (Taconic) were put on ad libitum estrogen fortified water containing 0.8 ug/mL 17β-estradiol (Sigma; St. Louis, Mo.) in 0.003% ethanol. MCF7-neo/HER2 cells, resuspended in 50% phenol red-free Matrigel (Becton Dickinson Bioscience; San Jose, Calif.) and Hank's Balanced Salt Solution, were inoculated subcutaneously in the number ⅔ mammary fat pad. Each mouse was injected with 5×10⁶ cells. Tumors were monitored until they reached an approximate tumor volume of 400 mm³. Seventeen days after tumor implantation (four days prior to dosing conjugates), mice were distributed into five groups of 4 mice per group and estrogen fortified water was removed and replaced with ad libitum regular drinking water. Twenty-one days after tumor implantation, designated as Day 1 of the study, mice were administered a single intravenous injection of vehicle (20 mM histidine acetate pH 5.5, 240 mM sucrose, 0.02% polysorbate 20), CNJ-1 (HER2) at 2, 10, or 25 mg/kg or CNJ-2 (B7H4) at 25 mg/kg in a volume of 200 uL. Twenty-four hours post-dose blood was collected via retro-orbital bleeds and processed for serum. On Day 4, all mice were euthanized and tumors and blood were collected. Tumors were flash frozen at −80° C. and blood was processed for serum.

For protein extraction, each frozen tumor was transferred to a tissueTUBE (Covaris) and cryofractured using a cryoPREP Impactor set to impact level 5 (Covaris). Half of the pulverized tumor samples were resuspended in 300 uL cell extraction buffer (FNN0011, Life Technologies) supplemented with protease inhibitor cocktail (Roche), phosphatase inhibitor cocktail (Sigma) and containing one ⅛" Coneball (Glenmills) and two 3 mm Zirconia beads (Glenmills). The samples were homogenized in a Geno Grinder (SPEX Sample Prep) for 1.5 min at 1,500 rpm, and the extracts were cleared twice by centrifugation (14,000 rpm at 4° C. for 10 min). Protein concentrations were determined by BCA assay (Thermo Fisher Scientific). For each tumor sample, 26 μg of total protein was separated on a 4-12% NuPAGE Bis-Tris gel using MOPS buffer (Thermo Fisher Scientific) and transferred to a nitrocellulose membrane. The membranes were blocked for 1 h in Odyssey blocking buffer (LI-COR, cat #927-40000) and incubated overnight with primary antibodies directed against ERα (dilution 1:1000, Novus Biologicals, cat. #NBP2-26481) and β-tubulin (dilution 1:1000, LI-COR, cat. #926-42212). Following three 15 min washes in PBS-tween, the membranes were incubated with the secondary antibodies IR Dye 800 CW Donkey anti Rabbit (dilution 1:10,000, LI-COR, cat #926-32213) and IR Dye 680 RD Donkey anti Mouse (dilution 1:10,000, LI-COR, cat #926-68072) for 45 min. After three 15 min washes in PBS-tween, the membranes were scanned using an Odyssey CLx instrument (LI-COR) and the ERα and tubulin levels quantified. The ERα/tubulin ratio and standard error of the mean (SEM) were calculated using Excel and plotted using Prism6 (Graphpad).

Efforts have been made to ensure accuracy with respect to numbers used (e.g. amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for preparing an antibody-drug conjugate of Formula I:

Ab-(L1-D)p                        I or a pharmaceutically acceptable salt thereof, wherein
Ab is an antibody;
L1 is a linking moiety with the structure

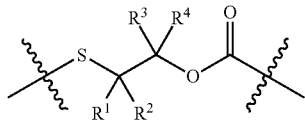

wherein,
$R^1$, $R^2$, $R^3$, and $R^4$ are independently selected from the group consisting of H, optionally substituted branched or linear $C_1$-$C_5$ alkyl, and optionally substituted $C_3$-$C_6$ cycloalkyl, or $R^3$ and $R^4$ taken together with the carbon atom to which they are bound form a $C_3$-$C_6$ cycloalkyl wherein said optionally substituted alkyl or cycloalkyl may be substituted with alkyl, cycloalkyl, aryl, heteroaryl, hydroxyl, nitrile, halo, alkoxy, haloalkoxy, arylalkoxy, acyloxy, alkylthio, sulfonate, amino, alkylamino, acylamino, carbamoyl, alkylcarbamoyl, or nitro;

D is

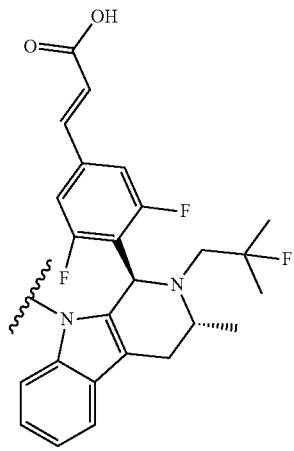

wherein L1 is covalently bonded to the secondary nitrogen; and p is 1, 2, 3, 4, 5, 6, 7, 8, 9, or 10;

the method comprising:

i. contacting a compound of Formula II

T-L1-D    II with an antibody, wherein,

L1 and D are as described above,

T is a leaving group having the structure $R^5$—S, wherein $R^5$ is an optionally substituted pyridine, wherein an antibody-drug conjugate of Formula I is prepared.

2. The method of claim 1, wherein T-L1-D has the following formula:

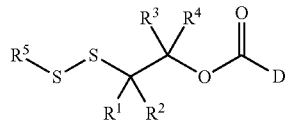

wherein, $R^5$ is selected from the group consisting of unsubstituted pyridine and nitropyridine.

3. The method of claim 1, wherein said antibody-drug conjugate of Formula I has the structure:

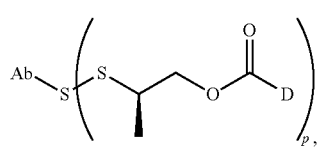

wherein p is 1, 2, 3, 4, 5, 6, 7, 8, 9, or 10.

4. The method of claim 1, wherein said antibody-drug conjugate of Formula I has the structure:

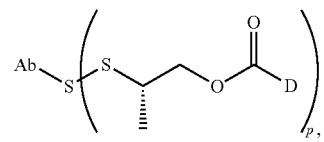

wherein p is 1, 2, 3, 4, 5, 6, 7, 8, 9, or 10.

5. The method of claim 1, wherein the antibody-drug conjugate of Formula I is selected from the group consisting of:

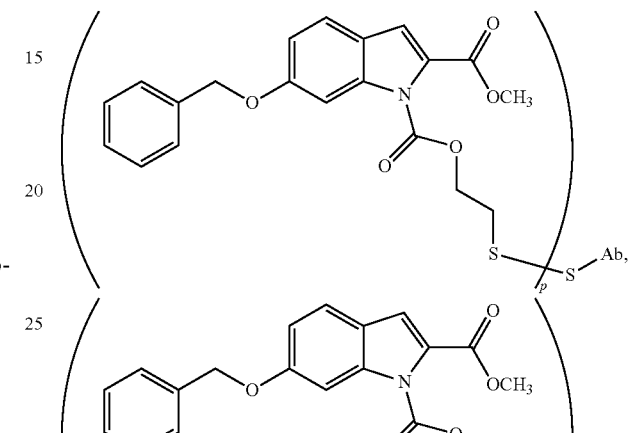

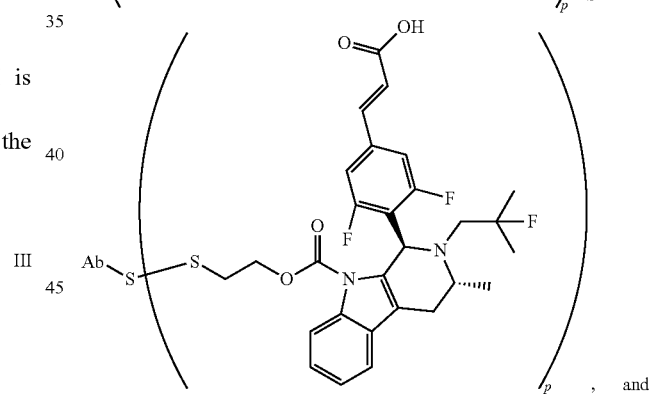

, and

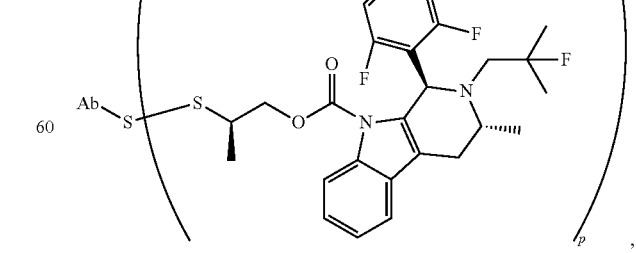

wherein p is 1, 2, 3, 4, 5, 6, 7, 8, 9, or 10.

6. A method for preparing a compound of Formula III:

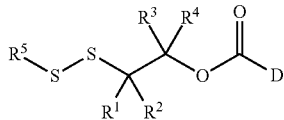

wherein, $R^1$, $R^2$, $R^3$, and $R^4$ are independently selected from the group consisting of H, optionally substituted branched or linear $C_1$-$C_5$ alkyl, and optionally substituted $C_3$-$C_6$ cycloalkyl, or $R^3$ and $R^4$ taken together with the carbon atom to which they are bound form a $C_3$-$C_6$ cycloalkyl ring wherein said optionally substituted alkyl or cycloalkyl may be substituted with alkyl, cycloalkyl, aryl, heteroaryl, hydroxyl, nitrile, halo, alkoxy, haloalkoxy, arylalkoxy, acyloxy, alkylthio, sulfonate, amino, alkylamino, acylamino, carbamoyl, alkylcarbamoyl, or nitro; and D is

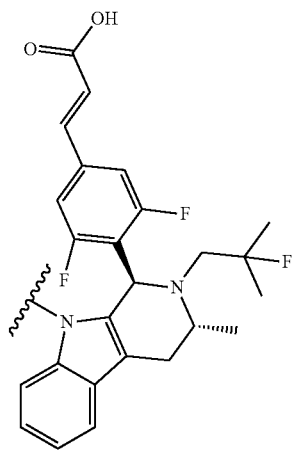 [SMILES: *n1c2c(c3ccccc31)C[C@@H](C)N(CC(C)(C)F)[C@@H]2c1c(F)cc(/C=C/C(=O)O)cc1F]

wherein the carbonyl in Formula III is covalently bonded to the secondary nitrogen in D;

$R^5$ is selected from the group consisting of optionally substituted pyridine and nitropyridine;

the method comprising:

i. contacting a compound of Formula V:

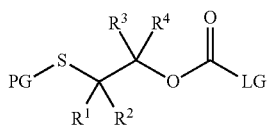

wherein LG is a leaving group and PG is a protecting group, with a compound, D, to prepare a compound of Formula VI:

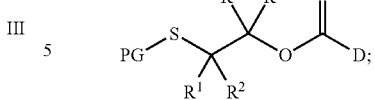

and, ii. deprotecting the compound of Formula VI under acidic conditions to prepare a compound of Formula III:

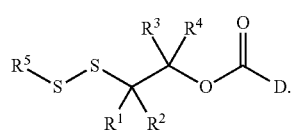

7. A compound of Formula III:

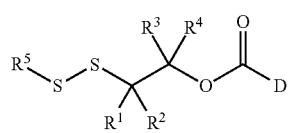

wherein, $R^1$, $R^2$, $R^3$, and $R^4$ are independently selected from the group consisting of H, optionally substituted branched or linear $C_1$-$C_5$ alkyl, and optionally substituted $C_3$-$C_6$ cycloalkyl, or $R^3$ and $R^4$ taken together with the carbon atom to which they are bound form a $C_3$-$C_6$ cycloalkyl ring wherein said optionally substituted alkyl or cycloalkyl may be substituted with alkyl, cycloalkyl, aryl, heteroaryl, hydroxyl, nitrile, halo, alkoxy, haloalkoxy, arylalkoxy, acyloxy, alkylthio, sulfonate, amino, alkylamino, acylamino, carbamoyl, alkylcarbamoyl, or nitro;

$R^5$ is selected from the group consisting of optionally substituted pyridine and nitropyridine;

and

D is

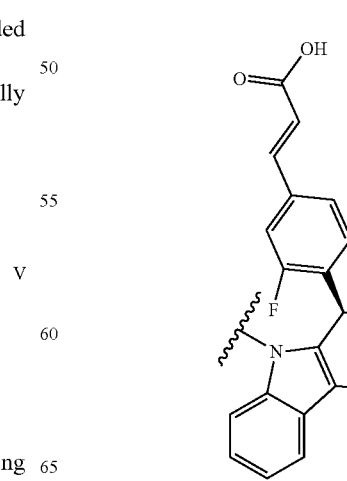

wherein the carbonyl in Formula III is covalently bonded to the secondary nitrogen in D.

8. The method of claim 1 for preparing an antibody-drug conjugate of Formula IV:

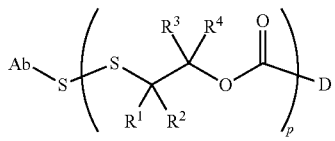

IV or a pharmaceutically acceptable salt thereof, wherein
Ab is an antibody;
$R^1$, $R^2$, $R^3$, and $R^4$ are independently selected from the group consisting of H, optionally substituted branched or linear $C_1$-$C_5$ alkyl, and optionally substituted $C_3$-$C_6$ cycloalkyl, or $R^3$ and $R^4$ taken together with the carbon atom to which they are bound form a $C_3$-$C_6$ cycloalkyl ring,
wherein said optionally substituted alkyl or cycloalkyl may be substituted with alkyl, cycloalkyl, aryl, heteroaryl, hydroxyl, nitrile, halo, alkoxy, haloalkoxy, arylalkoxy, acyloxy, alkylthio, sulfonate, amino, alkylamino, acylamino, carbamoyl, alkylcarbamoyl, or nitro;
D is

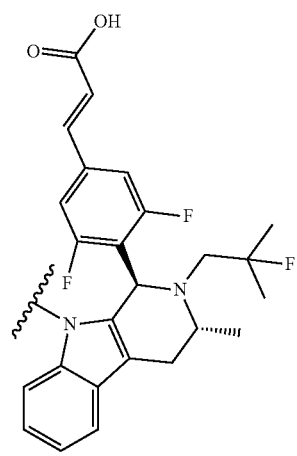 [SMILES: *n1c2c(c3ccccc31)C[C@@H](C)N(CC(C)(C)F)[C@@H]2c1c(F)cc(/C=C/C(=O)O)cc1F]

wherein the carbonyl in Formula IV is covalently bonded to the secondary nitrogen in D; and
p is 1, 2, 3, 4, 5, 6, 7, 8, 9, or 10;
the method comprising:
i. contacting a compound of Formula V:

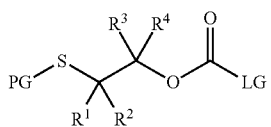

V with a compound D, wherein LG is a leaving group and PG is a protecting group, to prepare a compound of Formula VI:

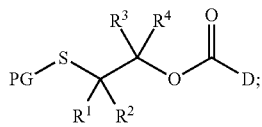

VI ii. contacting the compound of Formula VI with a disulfide $R^5$—S—S—$R^5$ under acidic conditions to prepare a compound of Formula III:

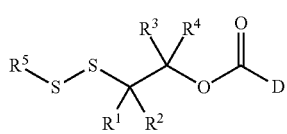

III wherein $R^5$ is an optionally substituted pyridine; and
iii. contacting a compound of Formula III with an antibody to prepare an antibody-drug conjugate of Formula IV.

9. The method of claim 2 wherein the compound of Formula III is selected from:

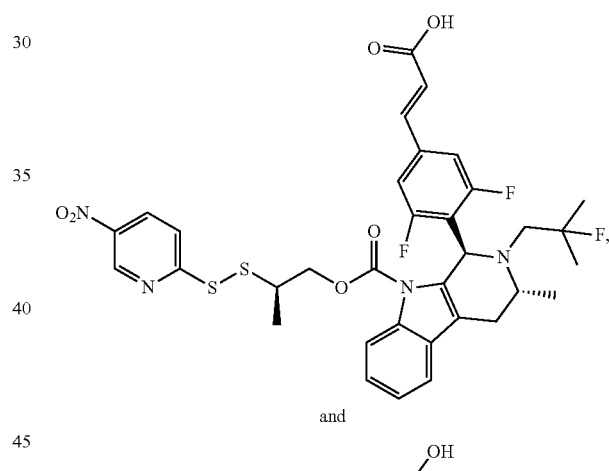

and

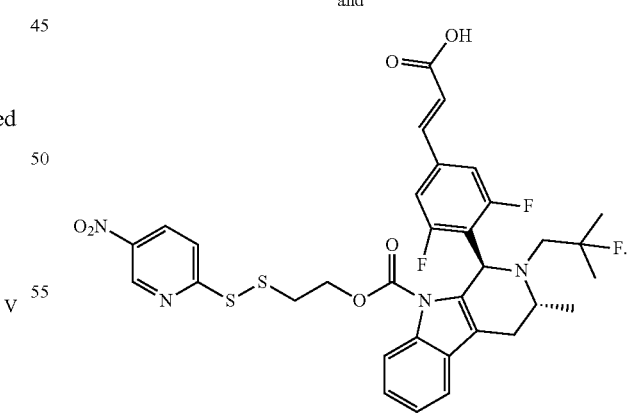

10. The method of claim 1 wherein the antibody is Anti-HER2 or Anti-B7H4.

* * * * *

UNITED STATES PATENT AND TRADEMARK OFFICE
CERTIFICATE OF CORRECTION

PATENT NO. : 11,547,762 B2
APPLICATION NO. : 16/354905
DATED : January 10, 2023
INVENTOR(S) : Thomas Pillow and Peter Scott Dragovich Page 1 of 1

It is certified that error appears in the above-identified patent and that said Letters Patent is hereby corrected as shown below:

In the Claims

Column 185, Lines 5-13, Claim 8, please delete

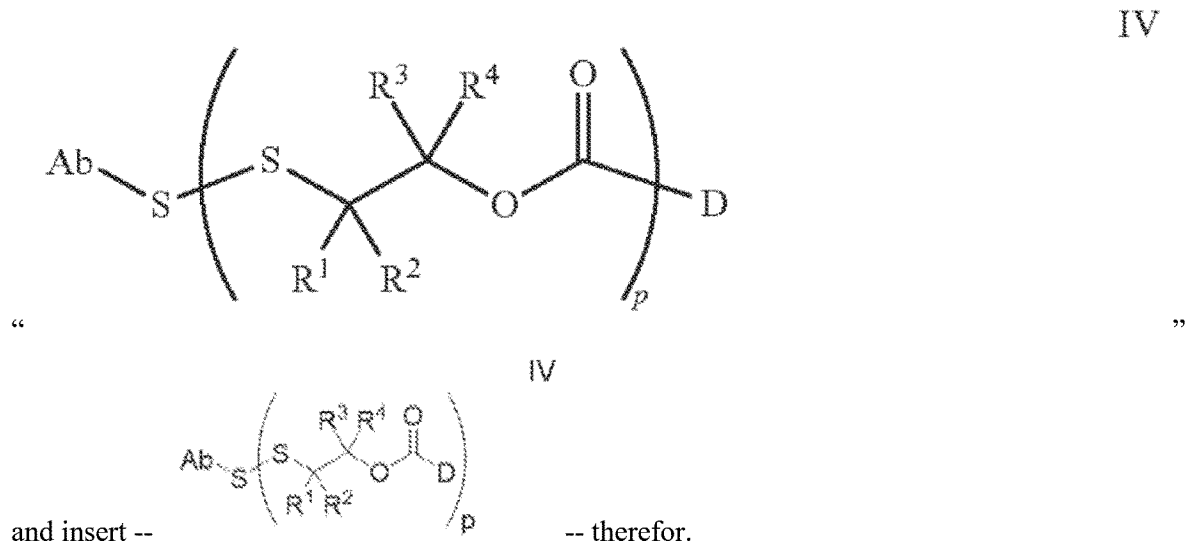

" and insert -- -- therefor.

Signed and Sealed this
Sixteenth Day of May, 2023

Katherine Kelly Vidal
*Director of the United States Patent and Trademark Office*

SEQUENCE LISTING

```
<160> NUMBER OF SEQ ID NOS: 98

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7
<211> LENGTH: 107
```

```
<212> TYPE: PRT
<213> ORGANISM: homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys
            100                 105

<210> SEQ ID NO 8
<211> LENGTH: 120
<212> TYPE: PRT
<213> ORGANISM: homo sapiens

<400> SEQUENCE: 8

Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser
        115                 120

<210> SEQ ID NO 9
<211> LENGTH: 11
<212> TYPE: PRT
<213> ORGANISM: homo sapiens

<400> SEQUENCE: 9

Ser Ala Ser Gln Gly Ile Ser Asn Tyr Leu Asn
1               5                   10

<210> SEQ ID NO 10
<211> LENGTH: 7
<212> TYPE: PRT
<213> ORGANISM: homo sapiens

<400> SEQUENCE: 10

Tyr Thr Ser Asn Leu His Ser
1               5
```

<210> SEQ ID NO 11
<211> LENGTH: 9
<212> TYPE: PRT
<213> ORGANISM: homo sapiens

<400> SEQUENCE: 11

Gln Gln Tyr Ser Glu Leu Pro Trp Thr
1               5

<210> SEQ ID NO 12
<211> LENGTH: 10
<212> TYPE: PRT
<213> ORGANISM: homo sapiens

<400> SEQUENCE: 12

Gly Phe Ser Leu Thr Gly Tyr Ser Val Asn
1               5                   10

<210> SEQ ID NO 13
<211> LENGTH: 16
<212> TYPE: PRT
<213> ORGANISM: homo sapiens

<400> SEQUENCE: 13

Met Ile Trp Gly Asp Gly Ser Thr Asp Tyr Asn Ser Ala Leu Lys Ser
1               5                   10                  15

<210> SEQ ID NO 14
<211> LENGTH: 12
<212> TYPE: PRT
<213> ORGANISM: homo sapiens

<400> SEQUENCE: 14

Asp Tyr Tyr Val Asn Tyr Ala Ser Trp Phe Ala Tyr
1               5                   10

<210> SEQ ID NO 15
<211> LENGTH: 214
<212> TYPE: PRT
<213> ORGANISM: homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

```
Lys Val Gln Trp Cys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 16
<211> LENGTH: 450
<212> TYPE: PRT
<213> ORGANISM: homo sapiens

<400> SEQUENCE: 16

Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
                290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 17
<211> LENGTH: 112
<212> TYPE: PRT
<213> ORGANISM: homo sapiens

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
                20                  25                  30

Arg Phe Thr Tyr Met His Trp Tyr Gln Gln Lys Pro Gly Gln Pro Pro
                35                  40                  45

Lys Leu Leu Ile Lys Tyr Ala Ser Ile Leu Glu Ser Gly Val Pro Asp
                50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
                100                 105                 110

<210> SEQ ID NO 18
<211> LENGTH: 118
<212> TYPE: PRT
<213> ORGANISM: homo sapiens

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Trp Met Asn Trp Val Arg Gln Ala Pro Gly Gln Gly Leu Glu Trp Ile
                35                  40                  45

Gly Met Ile His Pro Leu Asp Ala Glu Ile Arg Ala Asn Gln Lys Phe
```

```
                  50                  55                  60
Arg Asp Arg Val Thr Ile Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Gly Thr Tyr Asp Gly Gly Phe Glu Tyr Trp Gly Gln Gly Thr
            100                 105                 110

Leu Val Thr Val Ser Ser
        115
```

<210> SEQ ID NO 19
<211> LENGTH: 15
<212> TYPE: PRT
<213> ORGANISM: homo sapiens

<400> SEQUENCE: 19

```
Arg Ala Ser Gln Ser Val Ser Gly Ser Arg Phe Thr Tyr Met His
 1               5                  10                  15
```

<210> SEQ ID NO 20
<211> LENGTH: 7
<212> TYPE: PRT
<213> ORGANISM: homo sapiens

<400> SEQUENCE: 20

```
Tyr Ala Ser Ile Leu Glu Ser
 1               5
```

<210> SEQ ID NO 21
<211> LENGTH: 10
<212> TYPE: PRT
<213> ORGANISM: homo sapiens

<400> SEQUENCE: 21

```
Gln His Ser Trp Glu Ile Pro Pro Trp Thr
 1               5                  10
```

<210> SEQ ID NO 22
<211> LENGTH: 5
<212> TYPE: PRT
<213> ORGANISM: homo sapiens

<400> SEQUENCE: 22

```
Gly Tyr Trp Met Asn
 1               5
```

<210> SEQ ID NO 23
<211> LENGTH: 17
<212> TYPE: PRT
<213> ORGANISM: homo sapiens

<400> SEQUENCE: 23

```
Met Ile His Pro Leu Asp Ala Glu Ile Arg Ala Asn Gln Lys Phe Arg
 1               5                  10                  15

Asp
```

<210> SEQ ID NO 24
<211> LENGTH: 9
<212> TYPE: PRT
<213> ORGANISM: homo sapiens

<400> SEQUENCE: 24

Gly Thr Tyr Asp Gly Gly Phe Glu Tyr
1               5

<210> SEQ ID NO 25
<211> LENGTH: 219
<212> TYPE: PRT
<213> ORGANISM: homo sapiens

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 26
<211> LENGTH: 448
<212> TYPE: PRT
<213> ORGANISM: homo sapiens

<400> SEQUENCE: 26

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 27
<211> LENGTH: 17
<212> TYPE: PRT
<213> ORGANISM: homo sapiens

<400> SEQUENCE: 27

Met Ile His Pro Met Asp Ser Glu Ile Arg Ala Asn Gln Lys Phe Arg
1               5                   10                  15

Asp

<210> SEQ ID NO 28
<211> LENGTH: 17
<212> TYPE: PRT
<213> ORGANISM: homo sapiens

<400> SEQUENCE: 28

Met Ile His Pro Leu Asp Ser Glu Ile Arg Ala Asn Gln Lys Phe Arg
1               5                   10                  15

Asp

<210> SEQ ID NO 29
<211> LENGTH: 9
<212> TYPE: PRT
<213> ORGANISM: homo sapiens

<400> SEQUENCE: 29

Gly Thr Tyr Asp Gly Gly Phe Lys Tyr
1               5

<210> SEQ ID NO 30
<211> LENGTH: 219
<212> TYPE: PRT
<213> ORGANISM: homo sapiens

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Cys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 448
<212> TYPE: PRT
<213> ORGANISM: homo sapiens

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser Cys Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser

```
                    405                 410                 415
Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445

<210> SEQ ID NO 32
<211> LENGTH: 11
<212> TYPE: PRT
<213> ORGANISM: homo sapiens

<400> SEQUENCE: 32

Lys Ala Ser Asp Leu Ile His Asn Trp Leu Ala
1               5                   10

<210> SEQ ID NO 33
<211> LENGTH: 8
<212> TYPE: PRT
<213> ORGANISM: homo sapiens

<400> SEQUENCE: 33

Tyr Gly Ala Thr Ser Leu Glu Thr
1               5

<210> SEQ ID NO 34
<211> LENGTH: 9
<212> TYPE: PRT
<213> ORGANISM: homo sapiens

<400> SEQUENCE: 34

Gln Gln Tyr Trp Thr Thr Pro Phe Thr
1               5

<210> SEQ ID NO 35
<211> LENGTH: 11
<212> TYPE: PRT
<213> ORGANISM: homo sapiens

<400> SEQUENCE: 35

Gly Tyr Ser Ile Thr Asn Asp Tyr Ala Trp Asn
1               5                   10

<210> SEQ ID NO 36
<211> LENGTH: 17
<212> TYPE: PRT
<213> ORGANISM: homo sapiens

<400> SEQUENCE: 36

Gly Tyr Ile Ser Tyr Ser Gly Tyr Thr Thr Tyr Asn Pro Ser Leu Lys
1               5                   10                  15

Ser

<210> SEQ ID NO 37
<211> LENGTH: 9
<212> TYPE: PRT
<213> ORGANISM: homo sapiens

<400> SEQUENCE: 37

Ala Arg Trp Ala Ser Gly Leu Asp Tyr
1               5

<210> SEQ ID NO 38
<211> LENGTH: 108
```

-continued

```
<212> TYPE: PRT
<213> ORGANISM: homo sapiens

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg
            100                 105

<210> SEQ ID NO 39
<211> LENGTH: 116
<212> TYPE: PRT
<213> ORGANISM: homo sapiens

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ala Ser Gly Leu Asp Tyr Trp Gly Gln Gly Thr Leu Val
            100                 105                 110

Thr Val Ser Ser
        115

<210> SEQ ID NO 40
<211> LENGTH: 11
<212> TYPE: PRT
<213> ORGANISM: homo sapiens

<400> SEQUENCE: 40

Gly Tyr Ser Ile Thr Ser Asp Tyr Ala Trp Asn
1               5                   10

<210> SEQ ID NO 41
<211> LENGTH: 17
<212> TYPE: PRT
<213> ORGANISM: homo sapiens

<400> SEQUENCE: 41

Gly Tyr Ile Ser Asn Ser Gly Ser Thr Ser Tyr Asn Pro Ser Leu Lys
1               5                   10                  15
```

Ser

<210> SEQ ID NO 42
<211> LENGTH: 15
<212> TYPE: PRT
<213> ORGANISM: homo sapiens

<400> SEQUENCE: 42

Glu Arg Asn Tyr Asp Tyr Asp Asp Tyr Tyr Ala Met Asp Tyr
1               5                   10                  15

<210> SEQ ID NO 43
<211> LENGTH: 17
<212> TYPE: PRT
<213> ORGANISM: homo sapiens

<400> SEQUENCE: 43

Lys Ser Ser Gln Ser Leu Leu Tyr Arg Ser Asn Gln Lys Asn Tyr Leu
1               5                   10                  15

Ala

<210> SEQ ID NO 44
<211> LENGTH: 7
<212> TYPE: PRT
<213> ORGANISM: homo sapiens

<400> SEQUENCE: 44

Trp Ala Ser Thr Arg Glu Ser
1               5

<210> SEQ ID NO 45
<211> LENGTH: 9
<212> TYPE: PRT
<213> ORGANISM: homo sapiens

<400> SEQUENCE: 45

Gln Gln Tyr Tyr Asn Tyr Pro Arg Thr
1               5

<210> SEQ ID NO 46
<211> LENGTH: 124
<212> TYPE: PRT
<213> ORGANISM: homo sapiens

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Asn Tyr Asp Tyr Asp Asp Tyr Tyr Ala Met Asp
            100                 105                 110

Tyr Trp Gly Gln Gly Thr Leu Val Thr Val Ser Ser

```
                115                 120
```

<210> SEQ ID NO 47
<211> LENGTH: 113
<212> TYPE: PRT
<213> ORGANISM: homo sapiens

<400> SEQUENCE: 47

Asp Ile Gln Met Thr Gln Ser Pro Ser Leu Ser Ala Ser Val Gly
1               5                   10                  15

Asp Arg Val Thr Ile Thr Cys Lys Ser Gln Ser Leu Leu Tyr Arg
            20                  25                  30

Ser Asn Gln Lys Asn Tyr Leu Ala Trp Tyr Gln Leu Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys Val Glu Ile
                100                 105                 110

Lys

<210> SEQ ID NO 48
<211> LENGTH: 10
<212> TYPE: PRT
<213> ORGANISM: homo sapiens

<400> SEQUENCE: 48

Gly Phe Ser Phe Ser Asp Phe Ala Met Ser
1               5                   10

<210> SEQ ID NO 49
<211> LENGTH: 18
<212> TYPE: PRT
<213> ORGANISM: homo sapiens

<400> SEQUENCE: 49

Ala Thr Ile Gly Arg Val Ala Phe His Thr Tyr Tyr Pro Asp Ser Met
1               5                   10                  15

Lys Gly

<210> SEQ ID NO 50
<211> LENGTH: 13
<212> TYPE: PRT
<213> ORGANISM: homo sapiens

<400> SEQUENCE: 50

Ala Arg His Arg Gly Phe Asp Val Gly His Phe Asp Phe
1               5                   10

<210> SEQ ID NO 51
<211> LENGTH: 16
<212> TYPE: PRT
<213> ORGANISM: homo sapiens

<400> SEQUENCE: 51

Arg Ser Ser Glu Thr Leu Val His Ser Ser Gly Asn Thr Tyr Leu Glu
1               5                   10                  15

-continued

<210> SEQ ID NO 52
<211> LENGTH: 7
<212> TYPE: PRT
<213> ORGANISM: homo sapiens

<400> SEQUENCE: 52

Arg Val Ser Asn Arg Phe Ser
1               5

<210> SEQ ID NO 53
<211> LENGTH: 9
<212> TYPE: PRT
<213> ORGANISM: homo sapiens

<400> SEQUENCE: 53

Phe Gln Gly Ser Phe Asn Pro Leu Thr
1               5

<210> SEQ ID NO 54
<211> LENGTH: 120
<212> TYPE: PRT
<213> ORGANISM: homo sapiens

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser
        115                 120

<210> SEQ ID NO 55
<211> LENGTH: 113
<212> TYPE: PRT
<213> ORGANISM: homo sapiens

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

```
Ser Phe Asn Pro Leu Thr Phe Gly Gln Gly Thr Lys Val Glu Ile Lys
                100                 105                 110
Arg
```

<210> SEQ ID NO 56
<211> LENGTH: 117
<212> TYPE: PRT
<213> ORGANISM: homo sapiens

<400> SEQUENCE: 56

```
Glu Val Gln Leu Val Glu Ser Gly Gly Leu Val Gln Pro Gly Gly
1               5                   10                  15

Ser Leu Arg Leu Ser Cys Ala Ala Ser Gly Tyr Thr Phe Ser Ser Tyr
                20                  25                  30

Trp Ile Glu Trp Val Arg Gln Ala Pro Gly Lys Gly Leu Glu Trp Ile
                35                  40                  45

Gly Glu Ile Leu Pro Gly Gly Asp Thr Asn Tyr Asn Glu Ile Phe
            50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
                100                 105                 110

Val Thr Val Ser Ser
            115
```

<210> SEQ ID NO 57
<211> LENGTH: 112
<212> TYPE: PRT
<213> ORGANISM: homo sapiens

<400> SEQUENCE: 57

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
                20                  25                  30

Gly Asp Ser Phe Leu Asn Trp Tyr Gln Gln Lys Pro Gly Lys Ala Pro
                35                  40                  45

Lys Leu Leu Ile Tyr Ala Ala Ser Asn Leu Glu Ser Gly Val Pro Ser
            50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
                100                 105                 110
```

<210> SEQ ID NO 58
<211> LENGTH: 10
<212> TYPE: PRT
<213> ORGANISM: homo sapiens

<400> SEQUENCE: 58

```
Gly Tyr Thr Phe Ser Ser Tyr Trp Ile Glu
1               5                   10
```

-continued

```
<210> SEQ ID NO 59
<211> LENGTH: 18
<212> TYPE: PRT
<213> ORGANISM: homo sapiens

<400> SEQUENCE: 59

Gly Glu Ile Leu Pro Gly Gly Gly Asp Thr Asn Tyr Asn Glu Ile Phe
1               5                   10                  15

Lys Gly

<210> SEQ ID NO 60
<211> LENGTH: 10
<212> TYPE: PRT
<213> ORGANISM: homo sapiens

<400> SEQUENCE: 60

Thr Arg Arg Val Pro Ile Arg Leu Asp Tyr
1               5                   10

<210> SEQ ID NO 61
<211> LENGTH: 15
<212> TYPE: PRT
<213> ORGANISM: homo sapiens

<400> SEQUENCE: 61

Lys Ala Ser Gln Ser Val Asp Tyr Glu Gly Asp Ser Phe Leu Asn
1               5                   10                  15

<210> SEQ ID NO 62
<211> LENGTH: 7
<212> TYPE: PRT
<213> ORGANISM: homo sapiens

<400> SEQUENCE: 62

Ala Ala Ser Asn Leu Glu Ser
1               5

<210> SEQ ID NO 63
<211> LENGTH: 9
<212> TYPE: PRT
<213> ORGANISM: homo sapiens

<400> SEQUENCE: 63

Gln Gln Ser Asn Glu Asp Pro Leu Thr
1               5

<210> SEQ ID NO 64
<211> LENGTH: 219
<212> TYPE: PRT
<213> ORGANISM: homo sapiens

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
                20                  25                  30

Ser Gly Asn Thr Tyr Leu Glu Trp Tyr Gln Gln Lys Pro Gly Lys Ala
            35                  40                  45

Pro Lys Leu Leu Ile Tyr Arg Val Ser Asn Arg Phe Ser Gly Val Pro
        50                  55                  60

Ser Arg Phe Ser Gly Ser Gly Ser Gly Thr Asp Phe Thr Leu Thr Ile
65                  70                  75                  80
```

```
Ser Ser Leu Gln Pro Glu Asp Phe Ala Thr Tyr Tyr Cys Phe Gln Gly
            85                  90                  95

Ser Phe Asn Pro Leu Thr Phe Gly Gln Gly Thr Lys Val Glu Ile Lys
        100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 65
<211> LENGTH: 450
<212> TYPE: PRT
<213> ORGANISM: homo sapiens

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg His Arg Gly Phe Asp Val Gly His Phe Asp Phe Trp Gly Gln
            100                 105                 110

Gly Thr Leu Val Thr Val Ser Ser Cys Ser Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 66
<211> LENGTH: 16
<212> TYPE: PRT
<213> ORGANISM: homo sapiens

<400> SEQUENCE: 66

Arg Ser Ser Gln Ser Ile Val His Ser Val Gly Asn Thr Phe Leu Glu
1               5                   10                  15

<210> SEQ ID NO 67
<211> LENGTH: 7
<212> TYPE: PRT
<213> ORGANISM: homo sapiens

<400> SEQUENCE: 67

Lys Val Ser Asn Arg Phe Ser
1               5

<210> SEQ ID NO 68
<211> LENGTH: 9
<212> TYPE: PRT
<213> ORGANISM: homo sapiens

<400> SEQUENCE: 68

Phe Gln Gly Ser Gln Phe Pro Tyr Thr
1               5

<210> SEQ ID NO 69
<211> LENGTH: 10
```

```
<212> TYPE: PRT
<213> ORGANISM: homo sapiens

<400> SEQUENCE: 69

Gly Tyr Glu Phe Ser Arg Ser Trp Met Asn
1               5                   10

<210> SEQ ID NO 70
<211> LENGTH: 17
<212> TYPE: PRT
<213> ORGANISM: homo sapiens

<400> SEQUENCE: 70

Arg Ile Tyr Pro Gly Asp Gly Asp Thr Asn Tyr Ser Gly Lys Phe Lys
1               5                   10                  15

Gly

<210> SEQ ID NO 71
<211> LENGTH: 11
<212> TYPE: PRT
<213> ORGANISM: homo sapiens

<400> SEQUENCE: 71

Asp Gly Ser Ser Trp Asp Trp Tyr Phe Asp Val
1               5                   10

<210> SEQ ID NO 72
<211> LENGTH: 113
<212> TYPE: PRT
<213> ORGANISM: homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
                20                  25                  30

Val Gly Asn Thr Phe Leu Glu Trp Tyr Gln Gln Lys Pro Gly Lys Ala
            35                  40                  45

Pro Lys Leu Leu Ile Tyr Lys Val Ser Asn Arg Phe Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Gln Phe Pro Tyr Thr Phe Gly Gln Gly Thr Lys Val Glu Ile Lys
            100                 105                 110

Arg

<210> SEQ ID NO 73
<211> LENGTH: 120
<212> TYPE: PRT
<213> ORGANISM: homo sapiens

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Glu Phe Ser Arg Ser
                20                  25                  30

Trp Met Asn Trp Val Arg Gln Ala Pro Gly Lys Gly Leu Glu Trp Val
            35                  40                  45
```

```
Gly Arg Ile Tyr Pro Gly Asp Gly Asp Thr Asn Tyr Ser Gly Lys Phe
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ser Ser Trp Asp Trp Tyr Phe Asp Val Trp Gly Gln
            100                 105                 110

Gly Thr Leu Val Thr Val Ser Ser
            115                 120

<210> SEQ ID NO 74
<211> LENGTH: 219
<212> TYPE: PRT
<213> ORGANISM: homo sapiens

<400> SEQUENCE: 74

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Val His Ser
            20                  25                  30

Val Gly Asn Thr Phe Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Gly
                 85                  90                  95

Ser Gln Phe Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Cys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 75
<211> LENGTH: 450
<212> TYPE: PRT
<213> ORGANISM: homo sapiens

<400> SEQUENCE: 75

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Glu Phe Ser Arg Ser
            20                  25                  30
```

```
Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Ser Gly Lys Phe
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ser Ser Trp Asp Trp Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

```
Gly Lys
    450

<210> SEQ ID NO 76
<211> LENGTH: 16
<212> TYPE: PRT
<213> ORGANISM: homo sapiens

<400> SEQUENCE: 76

Arg Ser Ser Gln Ser Leu Leu His Ser Asn Gly Tyr Asn Tyr Leu Asp
1               5                   10                  15

<210> SEQ ID NO 77
<211> LENGTH: 7
<212> TYPE: PRT
<213> ORGANISM: homo sapiens

<400> SEQUENCE: 77

Leu Gly Val Asn Ser Val Ser
1               5

<210> SEQ ID NO 78
<211> LENGTH: 9
<212> TYPE: PRT
<213> ORGANISM: homo sapiens

<400> SEQUENCE: 78

Met Gln Ala Leu Gln Thr Pro Trp Thr
1               5

<210> SEQ ID NO 79
<211> LENGTH: 5
<212> TYPE: PRT
<213> ORGANISM: homo sapiens

<400> SEQUENCE: 79

Asn His Ala Ile Ser
1               5

<210> SEQ ID NO 80
<211> LENGTH: 17
<212> TYPE: PRT
<213> ORGANISM: homo sapiens

<400> SEQUENCE: 80

Gly Ile Ile Pro Ile Phe Gly Thr Ala Asn Tyr Ala Gln Lys Phe Gln
1               5                   10                  15

Gly

<210> SEQ ID NO 81
<211> LENGTH: 8
<212> TYPE: PRT
<213> ORGANISM: homo sapiens

<400> SEQUENCE: 81

Glu Trp Ala Asp Val Phe Asp Ile
1               5

<210> SEQ ID NO 82
<211> LENGTH: 112
<212> TYPE: PRT
<213> ORGANISM: homo sapiens

<400> SEQUENCE: 82
```

```
Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Val Asn Ser Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 83
<211> LENGTH: 117
<212> TYPE: PRT
<213> ORGANISM: homo sapiens

<400> SEQUENCE: 83

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115
```

<210> SEQ ID NO 84
<211> LENGTH: 11
<212> TYPE: PRT
<213> ORGANISM: homo sapiens

<400> SEQUENCE: 84

```
Arg Ala Ser Gln Gly Ile Arg Asn Asp Leu Gly
1               5                   10
```

<210> SEQ ID NO 85
<211> LENGTH: 7
<212> TYPE: PRT
<213> ORGANISM: homo sapiens

<400> SEQUENCE: 85

```
Ala Ala Ser Ser Leu Gln Ser
1               5
```

<210> SEQ ID NO 86
<211> LENGTH: 9
<212> TYPE: PRT

<213> ORGANISM: homo sapiens

<400> SEQUENCE: 86

Leu Gln His Asn Ser Tyr Pro Trp Thr
1               5

<210> SEQ ID NO 87
<211> LENGTH: 5
<212> TYPE: PRT
<213> ORGANISM: homo sapiens

<400> SEQUENCE: 87

Gly Asn Tyr Met Ser
1               5

<210> SEQ ID NO 88
<211> LENGTH: 16
<212> TYPE: PRT
<213> ORGANISM: homo sapiens

<400> SEQUENCE: 88

Leu Ile Tyr Ser Gly Asp Ser Thr Tyr Tyr Ala Asp Ser Val Lys Gly
1               5                   10                  15

<210> SEQ ID NO 89
<211> LENGTH: 10
<212> TYPE: PRT
<213> ORGANISM: homo sapiens

<400> SEQUENCE: 89

Asp Gly Tyr Tyr Val Ser Asp Met Val Val
1               5                   10

<210> SEQ ID NO 90
<211> LENGTH: 107
<212> TYPE: PRT
<213> ORGANISM: homo sapiens

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 91
<211> LENGTH: 118
<212> TYPE: PRT
<213> ORGANISM: homo sapiens

<400> SEQUENCE: 91

Glu Val Gln Leu Val Glu Ser Gly Gly Ala Leu Ile Gln Pro Gly Gly
1               5                   10                  15

```
Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
            35                  40                  45

Ser Leu Ile Tyr Ser Gly Asp Ser Thr Tyr Tyr Ala Asp Ser Val Lys
 50                  55                  60

Gly Arg Phe Asn Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
            115

<210> SEQ ID NO 92
<211> LENGTH: 107
<212> TYPE: PRT
<213> ORGANISM: homo sapiens

<400> SEQUENCE: 92

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 93
<211> LENGTH: 118
<212> TYPE: PRT
<213> ORGANISM: homo sapiens

<400> SEQUENCE: 93

Glu Val Gln Leu Val Glu Ser Gly Gly Ala Leu Ile Gln Pro Gly Gly
 1               5                  10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
            35                  40                  45

Ser Leu Ile Tyr Ser Gly Asp Ser Thr Tyr Tyr Ala Asp Ser Val Lys
 50                  55                  60

Gly Arg Phe Thr Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110
```

Thr Val Thr Val Ser Ser
        115

<210> SEQ ID NO 94
<211> LENGTH: 107
<212> TYPE: PRT
<213> ORGANISM: homo sapiens

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 95
<211> LENGTH: 118
<212> TYPE: PRT
<213> ORGANISM: homo sapiens

<400> SEQUENCE: 95

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Ser Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 96
<211> LENGTH: 107
<212> TYPE: PRT
<213> ORGANISM: homo sapiens

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

```
Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Leu Glu Ile Lys
                100                 105
```

<210> SEQ ID NO 97
<211> LENGTH: 118
<212> TYPE: PRT
<213> ORGANISM: homo sapiens

<400> SEQUENCE: 97

```
Glu Val Gln Leu Val Glu Ser Gly Gly Ala Leu Ile Gln Pro Gly Gly
 1               5                  10                  15

Ser Leu Arg Leu Ser Cys Val Ala Ser Gly Phe Thr Ile Ser Gly Asn
                20                  25                  30

Tyr Met Ser Trp Val Arg Gln Ala Pro Gly Lys Gly Leu Glu Trp Val
            35                  40                  45

Ser Leu Ile Tyr Ser Gly Asp Ser Thr Tyr Tyr Ala Asp Ser Val Lys
 50                  55                  60

Gly Arg Phe Ala Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
                 85                  90                  95

Arg Asp Gly Tyr Tyr Val Ser Asp Met Val Val Trp Gly Lys Gly Thr
                100                 105                 110

Thr Val Thr Val Ser Ser
            115
```

<210> SEQ ID NO 98
<211> LENGTH: 1255
<212> TYPE: PRT
<213> ORGANISM: homo sapiens

<400> SEQUENCE: 98

```
Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Asn Thr Thr Pro
            115                 120                 125
```

```
Val Thr Gly Ala Ser Pro Gly Gly Leu Arg Glu Leu Gln Leu Arg Ser
130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
        195                 200                 205
Ser Glu Asp Cys Gln Ser Leu Thr Arg Thr Val Cys Ala Gly Gly Cys
210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
        275                 280                 285
Tyr Thr Phe Gly Ala Ser Cys Val Thr Ala Cys Pro Tyr Asn Tyr Leu
290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
        355                 360                 365
Lys Ile Phe Gly Ser Leu Ala Phe Leu Pro Glu Ser Phe Asp Gly Asp
370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
530                 535                 540
Arg Val Leu Gln Gly Leu Pro Arg Glu Tyr Val Asn Ala Arg His Cys
```

```
           545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
                580                 585                 590
Pro Pro Phe Cys Val Ala Arg Cys Pro Ser Gly Val Lys Pro Asp Leu
                595                 600                 605
Ser Tyr Met Pro Ile Trp Lys Phe Pro Asp Glu Gly Ala Cys Gln
        610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Leu Gly Val Val Phe Gly
                660                 665                 670
Ile Leu Ile Lys Arg Arg Gln Gln Lys Ile Arg Lys Tyr Thr Met Arg
                675                 680                 685
Arg Leu Leu Gln Glu Thr Glu Leu Val Glu Pro Leu Thr Pro Ser Gly
        690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
                740                 745                 750
Lys Val Leu Arg Glu Asn Thr Ser Pro Lys Ala Asn Lys Glu Ile Leu
                755                 760                 765
Asp Glu Ala Tyr Val Met Ala Gly Val Gly Ser Pro Tyr Val Ser Arg
        770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
                820                 825                 830
Met Ser Tyr Leu Glu Asp Val Arg Leu Val His Arg Asp Leu Ala Ala
        835                 840                 845
Arg Asn Val Leu Val Lys Ser Pro Asn His Val Lys Ile Thr Asp Phe
850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
                900                 905                 910
Trp Glu Leu Met Thr Phe Gly Ala Lys Pro Tyr Asp Gly Ile Pro Ala
        915                 920                 925
Arg Glu Ile Pro Asp Leu Leu Glu Lys Gly Glu Arg Leu Pro Gln Pro
                930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
```

```
Ser Arg Met Ala Arg Asp Pro Gln Arg Phe Val Val Ile Gln Asn Glu
            980                 985                 990
Asp Leu Gly Pro Ala Ser Pro Leu Asp Ser Thr Phe Tyr Arg Ser Leu
        995                1000                1005
Leu Glu Asp Asp Met Gly Asp Leu Val Asp Ala Glu Glu Tyr
   1010            1015            1020
Leu Val Pro Gln Gln Gly Phe Phe Cys Pro Asp Pro Ala Pro Gly
   1025            1030            1035
Ala Gly Gly Met Val His His Arg His Arg Ser Ser Ser Thr Arg
   1040            1045            1050
Ser Gly Gly Gly Asp Leu Thr Leu Gly Leu Glu Pro Ser Glu Glu
   1055            1060            1065
Glu Ala Pro Arg Ser Pro Leu Ala Pro Ser Glu Gly Ala Gly Ser
   1070            1075            1080
Asp Val Phe Asp Gly Asp Leu Gly Met Gly Ala Ala Lys Gly Leu
   1085            1090            1095
Gln Ser Leu Pro Thr His Asp Pro Ser Pro Leu Gln Arg Tyr Ser
   1100            1105            1110
Glu Asp Pro Thr Val Pro Leu Pro Ser Glu Thr Asp Gly Tyr Val
   1115            1120            1125
Ala Pro Leu Thr Cys Ser Pro Gln Pro Glu Tyr Val Asn Gln Pro
   1130            1135            1140
Asp Val Arg Pro Gln Pro Pro Ser Pro Arg Glu Gly Pro Leu Pro
   1145            1150            1155
Ala Ala Arg Pro Ala Gly Ala Thr Leu Glu Arg Pro Lys Thr Leu
   1160            1165            1170
Ser Pro Gly Lys Asn Gly Val Val Lys Asp Val Phe Ala Phe Gly
   1175            1180            1185
Gly Ala Val Glu Asn Pro Glu Tyr Leu Thr Pro Gln Gly Gly Ala
   1190            1195            1200
Ala Pro Gln Pro His Pro Pro Pro Ala Phe Ser Pro Ala Phe Asp
   1205            1210            1215
Asn Leu Tyr Tyr Trp Asp Gln Asp Pro Pro Glu Arg Gly Ala Pro
   1220            1225            1230
Pro Ser Thr Phe Lys Gly Thr Pro Thr Ala Glu Asn Pro Glu Tyr
   1235            1240            1245
Leu Gly Leu Asp Val Pro Val
   1250            1255
```